(12) United States Patent
Hickman et al.

(10) Patent No.: US 9,489,474 B2
(45) Date of Patent: Nov. 8, 2016

(54) MODEL AND METHODS FOR IDENTIFYING POINTS OF ACTION IN ELECTRICALLY ACTIVE CELLS

(75) Inventors: James Hickman, Orlando, FL (US); Peter Molnar, Szombathely (HU); Frank Sommerhage, Casselberry, FL (US); Jonathan Ernest Hood, Charlotte, NC (US); Jerry Jenkins, Harvest, AL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 862 days.

(21) Appl. No.: 13/576,442

(22) PCT Filed: Feb. 7, 2011

(86) PCT No.: PCT/US2011/023921
§ 371 (c)(1),
(2), (4) Date: Dec. 21, 2012

(87) PCT Pub. No.: WO2011/097574
PCT Pub. Date: Aug. 11, 2011

(65) Prior Publication Data
US 2013/0096888 A1    Apr. 18, 2013

Related U.S. Application Data

(60) Provisional application No. 61/301,669, filed on Feb. 5, 2010.

(51) Int. Cl.
| G01N 33/48 | (2006.01) |
| G06F 17/50 | (2006.01) |
| G01N 33/50 | (2006.01) |
| G06F 19/12 | (2011.01) |
| G06G 7/58 | (2006.01) |

(52) U.S. Cl.
CPC ....... *G06F 17/5009* (2013.01); *G01N 33/5058* (2013.01); *G06F 19/12* (2013.01)

(58) Field of Classification Search
CPC .......................... G06F 19/12; G06F 17/5009
See application file for complete search history.

(56) References Cited

U.S. PATENT DOCUMENTS

| 5,442,510 A | 8/1995 | Schwartz |
| 5,948,621 A | 9/1999 | Turner |
| 6,866,383 B2 | 3/2005 | Naik |
| 6,916,541 B2 | 7/2005 | Pantano |
| 6,935,165 B2 | 8/2005 | Bashir |
| 7,384,786 B2 | 6/2008 | Freyman |
| 7,541,146 B2 | 6/2009 | Lewis |
| 7,579,189 B2 | 8/2009 | Freyman |
| 7,691,629 B2 | 4/2010 | Johe |
| 7,923,015 B2 | 4/2011 | Vazquez-Martinez |
| 7,927,671 B2 | 4/2011 | Kato |
| 8,071,319 B2 | 12/2011 | Metzger |
| 8,178,602 B2 | 5/2012 | Mao |
| 8,318,488 B1 | 11/2012 | Bohlen |
| 8,318,489 B2 | 11/2012 | Davidson |
| 8,318,951 B2 | 11/2012 | Olson |
| 2003/0065452 A1 | 4/2003 | Hickman |
| 2003/0144823 A1 | 7/2003 | Fox |
| 2003/0211542 A1 | 11/2003 | Lee |
| 2006/0105457 A1 | 5/2006 | Rameshwar |
| 2007/0015138 A1 | 1/2007 | Barlow |
| 2007/0117217 A1 | 5/2007 | Lal |
| 2007/0212723 A1 | 9/2007 | Dudley |
| 2008/0124789 A1 | 5/2008 | Hickman |
| 2008/0227137 A1 | 9/2008 | Zhang |
| 2009/0029463 A1 | 1/2009 | Collins |
| 2009/0239940 A1 | 9/2009 | Del Monte |
| 2009/0305319 A1 | 12/2009 | Baudenbacher |
| 2011/0250682 A1 | 10/2011 | Hickman |
| 2012/0122728 A1 | 5/2012 | Hickman |
| 2012/0128639 A1 | 5/2012 | Hickman et al. |

FOREIGN PATENT DOCUMENTS

| CA | 2788905 | 2/2011 |
| CA | 2798777 | 5/2011 |
| EP | 2434896 | 4/2012 |
| EP | 2435585 | 4/2012 |
| EP | 2531910 | 12/2012 |
| EP | 2585171 | 5/2013 |

(Continued)

OTHER PUBLICATIONS

U.S. Appl. No. 60/916,641, filed May 8, 2007, James J. Hickman.

(Continued)

*Primary Examiner* — Eric S Dejong
(74) *Attorney, Agent, or Firm* — Meunier Carlin & Curfman LLP

(57) ABSTRACT

The invention provides a model for generating predicted action potentials of an electrically active cell. The disclosed model includes three operatively coupled submodels. A first submodel contains Hodgkin-Huxley elements generating action potentials based on electrical equivalent circuits. A second submodel is based on reaction kinetics of cell metabolism and is operatively coupled with the first submodel. A third submodel is based on Boolean dynamics representing signaling and associated cellular processes and is operatively coupled with the first and second submodels. The invention includes storing a library of calculated action potentials and associated cellular parameters generated by the model, applying a stimulus to the electrically active cell in vitro so that the cell generates an action potential; and comparing the cell-generated action potential with those stored in the library, wherein a match is predictive of the cellular point of action of the applied stimulus according to the parameters stored.

17 Claims, 17 Drawing Sheets

(56) References Cited

FOREIGN PATENT DOCUMENTS

| WO | WO 2010/138679 | 12/2010 |
|---|---|---|
| WO | WO 2010/138782 | 12/2010 |
| WO | WO 2011/097574 | 8/2011 |
| WO | WO 2011/133985 | 10/2011 |
| WO | WO 2012/158923 | 11/2012 |
| WO | PCT/US2013/055617 | 8/2013 |

OTHER PUBLICATIONS

U.S. Appl. No. 60/945,952, filed Jun. 25, 2007, James J. Hickman.
U.S. Appl. No. 61/159,851, filed Mar. 13, 2009, James J. Hickman.
U.S. Appl. No. 61/259,715, filed Nov. 10, 2009, James J. Hickman.
U.S. Appl. No. 61/171,958, filed Apr. 23, 2009, James J. Hickman.
U.S. Appl. No. 61/331,999, filed May 6, 2010, James J. Hickman.
U.S. Appl. No. 61/332,003, filed May 6, 2010, James J. Hickman.
U.S. Appl. No. 61/171,968, filed Apr. 23, 2009, James J. Hickman.
U.S. Appl. No. 61/181,718, filed May 28, 2009, James J. Hickman.
U.S. Appl. No. 61/181,737, filed May 28, 2009, James J. Hickman.
U.S. Appl. No. 61/181,868, filed May 28, 2009, James J. Hickman.
U.S. Appl. No. 61/252,195, filed Oct. 16, 2009, James J. Hickman.
U.S. Appl. No. 61/257,504, filed Nov. 3, 2009, James J. Hickman.
U.S. Appl. No. 61/301,669, filed Feb. 5, 2010, James J. Hickman.
U.S. Appl. No. 61/487,251, filed May 17, 2011, James J. Hickman.
U.S. Appl. No. 61/684,168, filed Aug. 17, 2012, James J. Hickman.
U.S. Appl. No. 61/789,184, filed Mar. 15, 2013, James J. Hickman.
U.S. Appl. No. 61/732,042, filed Nov. 30, 2012, James J. Hickman.
U.S. Appl. No. 61/732,574, filed Dec. 3, 2012, James J. Hickman.
U.S. Appl. No. 61/784,923, filed Mar. 14, 2013, James J. Hickman.
U.S. Appl. No. 61/758,628, filed Jan. 30, 2013, James J. Hickman.
U.S. Appl. No. 61/790,061, filed Mar. 15, 2013, James J. Hickman.
U.S. Appl. No. 61/789,587, filed Mar. 15, 2013, James J. Hickman.
U.S. Appl. No. 12/117,339, J.J. Hickman.
U.S. Appl. No. 12/145,810, J.J. Hickman.
U.S. Appl. No. 12/661,323, J.J. Hickman.
U.S. Appl. No. 12/765,399, J.J. Hickman.
U.S. Appl. No. 12/765,996, J.J. Hickman.
U.S. Appl. No. 12/788,732, J.J. Hickman.
U.S. Appl. No. 12/938,701, J.J. Hickman.
Preliminary Amendment filed Jul. 10, 2012 for U.S. Appl. No. 12/117,339, filed May 8, 2008 (Hickman et al—inventors)(5 pages).
Non-Final Office Action issued Aug. 24, 2012 for U.S. Appl. No. 12/117,339, filed May 8, 2008 (Hickman et al—inventors)(10 pages).
Response to Non-Final Office Action filed Jan. 24, 2013 for U.S. Appl. No. 12/117,339, filed May 8, 2008 (Hickman et al—inventors)(8 pages).
Non-Final Office Action issued Oct. 11, 2013 for U.S. Appl. No. 12/117,339, filed May 8, 2008 (Hickman et al—inventors)(10 pages).
Restriction Requirement issued Jun. 7, 2011 for U.S. Appl. No. 12/145,810, filed Jun. 25, 2008 (Hickman et al—inventors)(5 pages).
Response to Restriction Requirement filed Jul. 5, 2011 for U.S. Appl. No. 12/145,810, filed Jun. 25, 2008 (Hickman et al—inventors)(7 pages).
Non-Final Office Action issued Aug. 31, 2011 for U.S. Appl. No. 12/145,810, filed Jun. 25, 2008 (Hickman et al—inventors)(8 pages).
Response to Non-Final Office Action filed Jan. 31, 2012 for U.S. Appl. No. 12/145,810, filed Jun. 25, 2008 (Hickman et al—inventors)(13 pages).
Final Office Action issued Apr. 9, 2012 for U.S. Appl. No. 12/145,810, filed Jun. 25, 2008 (Hickman et al—inventors)(7 pages).
Notice of Abandonment issued on Oct. 19, 2012 for U.S. Appl. No. 12/145,810, filed Jun. 25, 2008 (Hickman et al—inventors)(2 pages).
Restriction Requirement issued Sep. 27, 2012 for U.S. Appl. No. 12/661,323, filed Mar. 15, 2010 (Hickman et al—inventors)(10 pages).
Response to Restriction Requirement filed Nov. 17, 2012 for U.S. Appl. No. 12/661,323, filed Mar. 15, 2010 (Hickman et al—inventors)(7 pages).
Non-Final Office Action issued Mar. 13, 2013 for for U.S. Appl. No. 12/661,323, filed Mar. 15, 2010 (Hickman et al—inventors)(14 pages).
Response to Non-Final Office Action filed Jul. 12, 2013 for U.S. Appl. No. 12/661,323, filed Mar. 15, 2010 (Hickman et al—inventors)(11 pages).
Restriction Requirement issued Aug. 7, 2012 for U.S. Appl. No. 12/765,996, filed Feb. 23, 2010 (Hickman et al—inventors)(6 pages).
Response to Restriction Requirement filed on Sep. 7, 2012 for U.S. Appl. No. 12/765,996, filed Feb. 23, 2010 (Hickman et al—inventors)(7 pages).
Non-Final Office Action issued Nov. 13, 2012 for U.S. Appl. No. 12/765,996, filed Feb. 23, 2010 (Hickman et al—inventors)(11 pages).
Response to Non-Final Office Action filed on Apr. 12, 2013 for U.S. Appl. No. 12/765,996, filed Feb. 23, 2010 (Hickman et al—inventors)(70 pages).
Notice of Non-Compliant Amendment issued Apr. 19, 2013 for U.S. Appl. No. 12/765,996, filed Feb. 23, 2010 (Hickman et al—inventors)(2 pages).
Letter Withdrawing a Notice of Non-Compliant Amendment issued Apr. 25, 2013 for U.S. Appl. No. 12/765,996, filed Feb. 23, 2010 (Hickman et al—inventors)(2 pages).
Restriction Requirement issued Oct. 3, 2012 for U.S. Appl. No. 13/102,672, filed May 6, 2011 (Hickman et al—inventors)(7 pages).
Response to Restriction Requirement filed Nov. 16, 2012 for U.S. Appl. No. 13/102,672, filed May 6, 2011 (Hickman et al—inventors)(6 pages).
Preliminary Amendment filed Nov. 6, 2012 for U.S. Appl. No. 13/696,396, filed Nov. 6, 2012 (Hickman, et al—inventors)(4 pages).
Restriction Requirement issued Aug. 30, 2013 for U.S. Appl. No. 13/696,396, filed Nov. 6, 2012 (Hickman, et al—inventors)(11 pages).
International Search Report issued Jul. 28, 2011 for PCT Application No. PCT/US2011/035585, which published as WO 2011/133985 on Oct. 27, 2011 (Applicant: University of Central Florida Research Foundation // Inventors—James Hickman, et al.)(2 Pages).
Written Opinion issued Jul. 28, 2011 for PCT Application No. PCT/US2011/035585, which published as WO 2011/133985 on Oct. 27, 2011 (Applicant: University of Central Florida Research Foundation // Inventors—James Hickman, et al.)(4 pages).
International Preliminary Report on Patentability issued Oct. 23, 2012 for for PCT Application No. PCT/US2011/035585, which published as WO 2011/133985 on Oct. 27, 2011 (Applicant: University of Central Florida Research Foundation // Inventors—James Hickman, et al.)(5 pages).
Communication pursuant to Rules 161(2) and 162 EPC issued on Dec. 18, 2012 for European Patent Application No. 11772857.6, which caims priority to PCT/US11/35585, which published as WO 2011/133985 on Oct. 27, 2011 (Applicant: University of Central Florida Research Foundation // Inventors—James Hickman, et al.)(2 pages).
Response to Communication pursuant to Rules 161(2) and 162 EPC filed Aug. 2, 2012 for European Patent Application No. 11772857.6, which caims priority to PCT/US11/35585, which published as WO 2011/133985 on Oct. 27, 2011 (Applicant: University of Central Florida Research Foundation // Inventors—James Hickman, et al.).
Restriction Requirement issued Jul. 19, 2012 for U.S. Appl. No. 12/765,399, filed Apr. 22, 2010 (Hickman, et al—inventors)(7 pages).
Response to Restriction Requirement filed Aug. 17, 2012 for U.S. Appl. No. 12/765,399, filed Apr. 22, 2010 (Hickman, et al—inventors)(5 pages).

(56) References Cited

OTHER PUBLICATIONS

Non-Final Office Action issued Oct. 18, 2012 for U.S. Appl. No. 12/765,399, filed Apr. 22, 2010 (Hickman, et al—inventors)(9 pages).
Response to Non-Final Office Action filed Jan. 16, 2013 for U.S. Appl. No. 12/765,399, filed Apr. 22, 2010 (Hickman, et al—inventors)(49 pages).
Final Office Action issued Apr. 15, 2013 for U.S. Appl. No. 12/765,399, filed Apr. 22, 2010 (Hickman, et al—inventors)(7 pages).
Response to Final Office Action filed Aug. 15, 2013 for U.S. Appl. No. 12/765,399 filed Apr. 22, 2010 (Hickman, et al—inventors)(6 pages).
International Search Report issued Jul. 30, 2010 for PCT Application No. PCT/US2010/36336, which published as WO 2010/138679 on Dec. 2, 2010 (Applicant: University of Central Florida Research Foundation // Inventors—James Hickman, et al.)(2 Pages).
Written Opinion issued Jul. 30, 2010 for PCT Application No. PCT/US2010/036336, which published as WO 2010/138679 on Dec. 2, 2010 (Applicant: University of Central Florida Research Foundation // Inventors—James Hickman, et al.)(4 Pages).
International Preliminary Report on Patentability issued Nov. 29, 2011 for PCT Application No. PCT/US2010/036336, which published as WO 2010/138679 on Dec. 2, 2010 (Applicant: University of Central Florida Research Foundation // Inventors—James Hickman, et al.)(5 Pages).
Preliminary Amendment filed Nov. 28, 2011 for U.S. Appl. No. 13/322,911, filed Nov. 28, 2011 (Hickman, et al—inventors)(4 pages).
Non-Final Office Action issued Sep. 10, 2013 for U.S. Appl. No. 13/322,911, filed Nov. 28, 2011 (Hickman, et al—inventors)(14 pages).
Communication conveying Extended European Search Report issued Jan. 22, 2013 for EP Application No. 10781190.3, which claims priority to PCT/US2010/036336 filed on May 27, 2010 (Applicant—University of Central Florida Research Foundation// Inventors—James Hickman et al.) (6 Pages).
Restriction Requirement issued Sep. 14, 2012 for U.S. Appl. No. 12/765,399, filed May 27, 2010 (Hickman, et al—inventors)(5 pages).
Response to Restriction Requirement filed Nov. 14, 2012 for U.S. Appl. No. 12/788,732, filed May 27, 2010 (Hickman, et al—inventors)(6 pages).
Non-Final Office Action issued Feb. 28, 2013 for U.S. Appl. No. 12/788,732 filed May 27, 2010 (Hickman, et al—inventors)(6 pages).
Response to Non-Final Office Action filed May 28, 2013 for U.S. Appl. No. 12/788,732, filed May 27, 2010 (Hickman, et al—inventors)(11 pages).
Final Office Action issued Sep. 16, 2013 for U.S. Appl. No. 12/788,732, filed May 27, 2010 (Hickman, et al—inventors)(5 pages).
International Search Report issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(2 Pages).
Written Opinion issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(5 Pages).
International Preliminary Report on Patentability issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(6 Pages).
Preliminary Amendment filed Nov. 28, 2011 for U.S. Appl. No. 13/322,903, filed Nov. 28, 2011 (Hickman and Davis—inventors)(4 pages).
Restriction Requirement issued Nov. 27, 2012 for U.S. Appl. No. 13/322,903, filed Nov. 28, 2011 (Hickman and Davis—inventors)(6 pages).
Response to Restriction Requirement filed Dec. 1, 2012 for U.S. Appl. No. 13/322,903, filed Nov. 28, 2011 (Hickman and Davis—inventors)(6 pages).
Non-Final Office Action issued Jan. 31, 2013 for U.S. Appl. No. 13/322,903, filed Nov. 28, 2011 (Hickman and Davis—inventors)(17 pages).
Response to Non-Final Office Action filed Jul. 31, 2013 for U.S. Appl. No. 13/322,903, filed Nov. 28, 2011 (Hickman and Davis—inventors)(15 pages).
Communication pursuant to Rules 161(2) and 162 EPC issued on Jan. 23, 2012 for European Patent Application No. 10781254.7, which caims priority to PCT/US2010/36505 filed on May 28, 2010 (Applicant—University of Central Florida Research Foundation// Inventors—Hickman and Davis)(2 pages).
Response to Communication pursuant to Rules 161(2) and 162 EPC filed Aug. 2, 2012 for European Patent Application No. 10781254.7, which caims priority to PCT/US2010/36505 filed on May 28, 2010 (Applicant—University of Central Florida Research Foundation// Inventors—Hickman and Davis)(5 pages).
Restriction Requirement issued Mar. 7, 2013 for U.S. Appl. No. 12/938,701, filed Nov. 3, 2010 (Hickman, et al.—inventors)(7 pages).
Response to Restriction Requirement filed Apr. 8, 2013 for U.S. Appl. No. 12/938,701, filed Nov. 3, 2010 (Hickman, et al—inventors)(6 pages).
Non-Final Office Action issued Jun. 13, 2013 for U.S. Appl. No. 12/938,701, filed Nov. 3, 2010 (Hickman, et al—inventors)(8 pages).
Response to Non-Final Office Action filed Oct. 3, 2013 for U.S. Appl. No. 12/938,701, filed Nov. 3, 2010 (Hickman, et al—inventors)(8 pages).
International Search Report issued Jun. 7, 2011 for PCT Application No. PCT/US2011/023921, which published as WO 2011/097574 on Aug. 11, 2011 (Applicant: University of Central Florida Research Foundation // Inventors—James Hickman, et al.)(3 Pages).
Written Opinion issued Jun. 7, 2011 for PCT Application No. PCT/US2011/023921, which published as WO 2011/097574 on Aug. 11, 2011 (Applicant: University of Central Florida Research Foundation // Inventors—James Hickman, et al.)(5 Pages).
International Preliminary Report on Patentability issued Aug. 7, 2012 for PCT Application No. PCT/US2011/023921, which published as WO 2011/097574 on Aug. 11, 2011 (Applicant: University of Central Florida Research Foundation // Inventors—James Hickman, et al.)(6 Pages).
Communication pursuant to Rules 161(2) and 162 EPC issued on Oct. 10, 2012 for European Patent Application No. 11740493.9, which caims priority to PCT/US2011/023921 filed on Feb. 7, 2011 (Applicant—University of Central Florida Research Foundation// Inventors—James Hickman, et al.)(2 pages).
Response to Communication pursuant to Rules 161(2) and 162 EPC issued on Oct. 10, 2012 for European Patent Application No. 11740493.9, which caims priority to PCT/US2011/023921 filed on Feb. 7, 2011 (Applicant—University of Central Florida Research Foundation// Inventors—James Hickman, et al.)(4 pages).
Communication conveying Extended European Search Report issued Jul. 10, 2013 for EP Application No. 11740493.9, which claims priority to PCT/US2011/023921 filed on Feb. 7, 2011 (Applicant—University of Central Florida Research Foundation// Inventors—James Hickman, et al.)(7 Pages).
International Search Report issued Oct. 16, 2012 for PCT Application No. PCT/US2012/038358, which published as WO 2012/158923 on Nov. 22, 2012 (Applicant: University of Central Florida Research Foundation // Inventors—James Hickman, et al.)(4 Pages).
Written Opinion issued Oct. 16, 2012 for PCT Application No. PCT/US2012/38358, which published as WO 2012/158923 on Nov. 22, 2012 (Applicant: University of Central Florida Research Foundation // Inventors—James Hickman, et al.)(6 Pages).

(56) References Cited

OTHER PUBLICATIONS

Abbanat D, et al. (2003) Novel antibacterial agents for the treatment of serious Gram-positive infections. Expert Opin Investig Drugs. 12: 379-399.

Abdi H. (2003) Multivariate Analysis. Encyclopedia of Social Sciences Research Methods. M. Lewis-Beck, A. Bryman and T. Futing. Thousand Oaks (CA), Sage.

Adell A, et al. (2002) Origin and functional role of the extracellular serotonin in the midbrain raphe nuclei. Brain Res Brain Res Rev. 39: 154-180.

Agarwal A, et al. (2013) Microfluidic heart on a chip for higher throughput pharmacological studies. Lab Chip. 13: 3599-3608.

Ahern CA, et al. (2003) Ca2+ current and charge movements in skeletal myotubes promoted by the beta-subunit of the dihydropyridine receptor in the absence of ryanodine receptor type 1. Biophys J. 84: 942-959.

Ahmari SE, et al. (2000) Assembly of presynaptic active zones from cytoplasmic transport packets. Nat Neurosci. 3: 445-451.

Ahuja TK, et al. (2007) Hippocampal slice cultures integrated with multi-electrode arrays: A model for study of long-term drug effects on synaptic activity. Drug Development Research. 68: 84-93.

Ainscow EK, et al. (1999) Internal regulation of ATP turnover, glycolysis and oxidative phosphorylation in rat hepatocytes. Eur J Biochem. 266: 737-749.

Akaaboune M, et al. (2000) Developmental regulation of amyloid precursor protein at the neuromuscular junction in mouse skeletal muscle. Mol Cell Neurosci. 15: 355-367.

Akanda N, et al. (2008) Effect of malonate, a metabolic pathway inhibitor, on action potential peak shape and the relationship to cellular pathways. 38th Annual Meeting of the Society for Neuroscience. vol. 38.

Akanda N, et al. (2009) Analysis of toxin-induced changes in action potential shape for drug development. J Biomol Screen. 14: 1228-1235.

Alabed YZ, et al. (2006) Neuronal responses to myelin are mediated by rho kinase. J Neurochem. 96: 1616-1625.

Albensi BC. (2003) A comparison of drug treatment versus electrical stimulation for suppressing seizure activity. Drug News Perspect. 16: 347-352.

Albert R, et al.. (2003) The topology of the regulatory interactions predicts the expression pattern of the segment polarity genes in *Drosophila melanogaster*. J Theor Biol. 223: 1-18.

Albert Y, et al. (2005) Transcriptional regulation of myotube fate specification and intrafusal muscle fiber morphogenesis. J Cell Biol. 169: 257-268.

Alexander SL, et al. (1989) an atomic-resolution atomic-force microscope implemented using an optical lever. J Appl Phys. 65: 164-167.

Al-Shanti N, et al. (2008) Beneficial synergistic interactions of TNF-alpha and IL-6 in C2 skeletal myoblasts—potential cross-talk with IGF system. Growth Factors. 26: 61-73.

Alsina B, et al. (2001) Visualizing synapse formation in arborizing optic axons in vivo: dynamics and modulation by BDNF. Nat Neurosci. 4: 1093-1101.

Alterio J, et al. (1990) Acidic and basic fibroblast growth factor mRNAs are expressed by skeletal muscle satellite cells.Biochem Biophys Res Commun. 166: 1205-1212.

Altmann L. (2000) Multielectrode recordings of synaptic plasticity in brain slices: A new method for the assessment of neurotoxic effects. European Journal of Neuroscience. 12: 29-29.

Amarenco P, et al. (2006) High-dose atorvastatin after stroke or transient ischemic attack. N Engl J Med. 355: 549-559.

Amit M. (2007) Feeder-layer free culture system for human embryonic stem cells. Methods Mol Biol. 407: 11-20.

Anderson DJ, et al. (1997) Cell lineage determination and the control of neuronal identity in the neural crest. Cold Spring Harb Symp Quant Biol. 62: 493-504.

Anderson JE, et al. (1991) Distinctive patterns of basic fibroblast growth factor (bFGF) distribution in degenerating and regenerating areas of dystrophic (mdx) striated muscles. Dev Biol. 147: 96-109.

Andersson H, et al. (2004) Microfabrication and microfluidics for tissue engineering: state of the art and future opportunities. Lab Chip. 4: 98-103.

Antzelevitch C. (2001) Transmural dispersion of repolarization and the T wave. Cardiovasc Res. 50: 426-431.

Antzelevitch C. (2005) Cardiac repolarization. The long and short of it. Europace. 7: 3-9.

Aracil A, et al. (2004) Proceedings of Neuropeptides 2004, the XIV European Neuropeptides Club meeting. Neuropeptides. 38: 369-371.

Archer JD, et al. (2006) Persistent and improved functional gain in mdx dystrophic mice after treatment with L-arginine and deflazacort. FASEB J. 20: 738-740.

Armstrong DL, et al. (1999) Ion channel regulation. Introduction. Adv Second Messenger Phosphoprotein Res. 33: ix-xx.

Arnold HH, et al. (1998) Muscle differentiation: more complexity to the network of myogenic regulators. Curr Opin Genet Dev. 8: 539-544.

Arnone MI, et al. (1997) The hardwiring of development: organization and function of genomic regulatory systems. Development. 124: 1851-1864.

Arsic N, et al. (2004) Vascular endothelial growth factor stimulates skeletal muscle regeneration in vivo. Mol Ther. 10: 844-854.

Askanas V, et al. (1987) De novo neuromuscular junction formation on human muscle fibres cultured in monolayer and innervated by foetal rat spinal cord: ultrastructural and ultrastructural—cytochemical studies. J Neurocytol. 16: 523-537.

Asotra K, et al. (1993) Protein kinase C activity modulates myelin gene expression in enriched oligodendrocytes. J Neurosci Res. 34: 571-588.

Azzouz M, et al. (2004) VEGF delivery with retrogradely transported lentivector prolongs survival in a mouse ALS model. Nature. 429: 413-417.

Badie N, et al. (2009) A method to replicate the microstructure of heart tissue in vitro using DTMRI-based cell micropatterning. Ann Biomed Eng. 37: 2510-2521.

Bahr M, et al. (1991) In vitro myelination of regenerating adult rat retinal ganglion cell axons by Schwann cells. Glia. 4: 529-533.

Baker DC, et al. (2002) The origin and neuronal function of in vivo nonsynaptic glutamate. J Neurosci. 22: 9134-9141.

Bandi E, et al. (2008) Neural agrin controls maturation of the excitation-contraction coupling mechanism in human myotubes developing in vitro. Am J Physiol Cell Physiol. 294: C66-C73.

Bansal R, et al. (1992) Novel stage in the oligodendrocyte lineage defined by reactivity of progenitors with R-mAb prior to O1 anti-galactocerebroside. J Neurosci Res. 32: 309-316.

Baraban SC, et al. (1997) Osmolarity modulates K+ channel function on rat hippocampal interneurons but not CA1 pyramidal neurons. J Physiol. 498: 679-689.

Barbulovic-Nad I, et al. (2008) Digital microfluidics for cell-based assays. Lab Chip. 8: 519-526.

Baron W, et al. (2000) PDGF and FGF-2 signaling in oligodendrocyte progenitor cells: regulation of proliferation and differentiation by multiple intracellular signaling pathways. Mol Cell Neurosci. 15: 314-329.

Barone FC, et al. (1998) Ischemic preconditioning and brain tolerance: temporal histological and functional outcomes, protein synthesis requirement, and interleukin-1 receptor antagonist and early gene expression. Stroke. 29: 1937-1950; discussion 1950-1951.

Behar TN. (2001) Analysis of fractal dimension of O2A glial cells differentiating in vitro. Methods. 24: 331-339.

Belardinelli L, et al. (2003) Assessing predictors of drug-induced torsade de pointes. Trends Pharmacol Sci. 24: 619-625.

Bellamkonda R, et al. (1995) Hydrogel-based three-dimensional matrix for neural cells. J Biomed Mater Res. 29: 663-671.

Bellas E, et al. (2012) In vitro 3D full-thickness skin-equivalent tissue model using silk and collagen biomaterials. Macromol Biosci. 12: 1627-1236.

Benabid AL. (2003) Deep brain stimulation for Parkinson's disease. Curr Opin Neurobiol. 13: 696-706.

Bender A, et al. (2007) Analysis of pharmacology data and the prediction of adverse drug reactions and off-target effects from chemical structure. ChemMedChem. 2: 861-873.

(56) References Cited

OTHER PUBLICATIONS

Bentley A and Atkinsona, A. (2001) Whole cell biosensors—electrochemical and optical approaches to ecotoxicity testing. Toxicol In Vitro. 15: 469-475.
Berg MC, et al. (2004) Controlling mammalian cell interactions on patterned polyelectrolyte multilayer surfaces. Langmuir. 20: 1362-1368.
Berger TW, et al. (2001) Brain-implantable biomimetic electronics as the next era in neural prosthetics. Proceedings of the IEEE. 89: 993-1012.
Bernstein M, et al. (1996) Receptor-mediated calcium signalling in glial cells from mouse corpus callosum slices. J Neurosci Res. 46: 152-163.
Bers DM. (2002) Cardiac excitation-contraction coupling. Nature. 415: 198-205.
Bettinger CJ, et al. (2009) Engineering substrate topography at the micro- and nanoscale to control cell function. Angew Chem Int Ed Engl. 48: 5406-5415.
Bhalla US, et al. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN, et al.. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by muscle-derived factors. Development. 111: 221-232.
Bodine SC, et al. (2001) Identification of ubiquitin ligases required for skeletal muscle atrophy. Science. 294: 1704-1708.
Bogler O, et al. (1990) Cooperation between two growth factors promotes extended self-renewal and inhibits differentiation of oligodendrocyte-type-2 astrocyte (O-2A) progenitor cells. Proc Natl Acad Sci U S A. 87: 6368-6372.
Boillee S, et al. (2006) ALS: a disease of motor neurons and their nonneuronal neighbors. Neuron. 52: 39-59.
Boldin SA, , et al. (2000) Up-regulation of glucosylceramide synthesis upon stimulation of axonal growth by basic fibroblast growth factor. Evidence for posttranslational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.
Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al. (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silico simulation of synaptic processes. BMC Bioinformatics. 9 Suppl 4: S7.
Brand T, et al. (2000) EMBO Workshop Report: Molecular genetics of muscle development and neuromuscular diseases Kloster Irsee, Germany, Sep. 26-Oct. 1, 1999. EMBO J. 19: 1935-1941.
Brand-Saberi B, et al. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neurol. 148: 475-494.
Bren-Mattison Y, et al. (2002) Sonic hedgehog inhibits the terminal differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.
Brewer GJ, et al. (2008) NbActiv4 medium improvement to Neurobasal/B27 increases neuron synapse densities and network spike rates on multielectrode arrays. J Neurosci Methods. 170: 181-187.
Brewer GJ. (1997) Isolation and culture of adult rat hippocampal neurons. J Neurosci Methods. 71: 143-155.
Brewer GJ. (1999) Regeneration and proliferation of embryonic and adult rat hippocampal neurons in culture. Exp Neurol. 159: 237-247.
Brito-Martins M, et al. (2008) beta(1)- and beta(2)-adrenoceptor responses in cardiomyocytes derived from human embryonic stem cells: comparison with failing and non-failing adult human heart. Br J Pharmacol. 153: 751-759.
Brockes JP, et al. (1979) Studies on cultured rat Schwann cells. I. Establishment of purified populations from cultures of peripheral nerve. Brain Res. 165: 105-118.
Brokhman I, et al. (2008) Peripheral sensory neurons differentiate from neural precursors derived from human embryonic stem cells. Differentiation. 76: 145-155.
Brumovsky P, et al. (2007) Expression of the vesicular glutamate transporters-1 and -2 in adult mouse dorsal root ganglia and spinal cord and their regulation by nerve injury. Neuroscience. 147: 469-490.
Bult CJ, et al. (1996) Complete genome sequence of the methanogenic archaeon, Methanococcus jannaschii. Science. 273: 1058-1073.
Bunge MB, et al. (1962) Electron microscopic demonstration of connections between glia and myelin sheaths in the developing mammalian central nervous system. J Cell Biol. 12: 448-453.
Bunge RP. (1968) Glial cells and the central myelin sheath. Physiol Rev. 48: 197-251.
Bunge RP. (1993) Expanding roles for the Schwann cell: ensheathment, myelination, trophism and regeneration. Curr Opin Neurobiol. 3: 805-809.
Burdick JA, et al. (2008) Engineered microenvironments for controlled stem cell differentiation. Tissue Eng Part A. 15: 205-219.
Burgess C, et al. (2008) An endogenous glutamatergic drive onto somatic motoneurons contributes to the stereotypical pattern of muscle tone across the sleep-wake cycle. J Neurosci. 28: 4649-4660.
Butt HJ. (1996) Sensitive Method to Measure Changes in the Surface Stress of Solids. Journal of Colloid and Interface Science. 180: 251-260.
Buzanska L, et al. (2002) Human cord blood-derived cells attain neuronal and glial features in vitro. J Cell Sci. 115: 2131-2138.
Cai J, et al. (2007) Directed differentiation of human embryonic stem cells into functional hepatic cells. Hepatology. 45: 1229-1239.
Caiozzo VJ, et al. (1992) Response of slow and fast muscle to hypothyroidism: maximal shortening velocity and myosin isoforms. Am J Physiol. 263: C86-C94.
Cakir T, et al. (2007) Reconstruction and flux analysis of coupling between metabolic pathways of astrocytes and neurons: application to cerebral hypoxia. Theor Biol Med Model. 4: 48.
Campbell TJ, et al. (2001) Therapeutic drug monitoring: antiarrhythmic drugs. Br J Clin Pharmacol. 52 Suppl 1: 21S-34S.
Camu W and Henderson CE. (1992) Purification of embryonic rat motoneurons by panning on a monoclonal antibody to the low-affinity NGF receptor. J Neurosci Methods. 44: 59-70.
Camu W and Henderson CE. (1994) Rapid purification of embryonic rat motoneurons: an in vitro model for studying MND/ALS pathogenesis. J Neurol Sci. 124 Suppl: 73-74.

(56) References Cited

OTHER PUBLICATIONS

Cannon JG. (1998) Intrinsic and extrinsic factors in muscle aging. Ann N Y Acad Sci. 854: 72-77.
Caratsch CG, et al. (1994) Interferon-alpha, beta and tumor necrosis factor-alpha enhance the frequency of miniature end-plate potentials at rat neuromuscular junction. Neurosci Lett. 166: 97-100.
Carlsson L. (2006) In vitro and in vivo models for testing arrhythmogenesis in drugs. J Intern Med. 259: 70-80.
Carpenedo RL, et al. (2007) Rotary suspension culture enhances the efficiency, yield, and homogeneity of embryoid body differentiation. Stem Cells. 25: 2224-2234.
Carr PA, et al. (1989) Parvalbumin is highly colocalized with calbindin D28k and rarely with calcitonin gene-related peptide in dorsal root ganglia neurons of rat. Brain Res. 497: 163-170.
Carrasco DI, et al. (2005) Neurotrophin 4/5 is required for the normal development of the slow muscle fiber phenotype in the rat soleus. J Exp Biol. 206: 2191-2200.
Caspi O, et al. (2009) In vitro electrophysiological drug testing using human embryonic stem cell derived cardiomyocytes. Stem Cells Dev. 18: 161-172.
Catoire H, et al. (2008) Sirtuin inhibition protects from the polyalanine muscular dystrophy protein PABPN1. Hum Mol Genet. 17: 2108-2117.
Cerignoli F, et al. (2012) High throughput measurement of $Ca^{2+}$ dynamics for drug risk assessment in human stem cell-derived cardiomyocytes by kinetic image cytometry. J Pharmacol Toxicol Methods. 66: 246-256.
Chambers SM, et al. (2009) Highly efficient neural conversion of human ES and iPS cells by dual inhibition of SMAD signaling. Nat Biotechnol. 27: 275-280.
Chandran S, et al. (1998) Regional potential for oligodendrocyte generation in the rodent embryonic spinal cord following exposure to EGF and FGF-2. Glia. 24: 382-389.
Chang JC, et al. (2001) Modulation of neural network activity by patterning. Biosens Bioelectron. 16: 527-533.
Charpentier A, et al. (1993) RRR-alpha-tocopheryl succinate inhibits proliferation and enhances secretion of transforming growth factor-beta (TGF-beta) by human breast cancer cells. Nutr Cancer. 19: 225-239.
Chaudhary KW, et al. (2006) Embryonic stem cells in predictive cardiotoxicity: laser capture microscopy enables assay development. Toxicol Sci. 90: 149-158.
Chaves M, et al. (2005) Robustness and fragility of Boolean models for genetic regulatory networks. J Theor Biol. 235: 431-449.
Chaves M, et al. (2006) Methods of robustness analysis for Boolean models of gene control networks. Syst Biol (Stevenage). 153: 154-167.
Chen CS, et al. (1997) Geometric control of cell life and death. Science. 276: 1425-1428.
Chen EW, et al. (1995) Target regulation of a motor neuron-specific epitope. J Neurosci. 15: 1555-1566.
Chen J, et al. (2004) Role of exogenous and endogenous trophic factors in the regulation of extraocular muscle strength during development.Invest Ophthalmol Vis Sci. 45: 3538-3545.
Chen QS, et al. (2000) Impairment of hippocampal long-term potentiation by Alzheimer amyloid beta-peptides. J Neurosci Res. 60: 65-72.
Chen X, et al. (2005) Dedifferentiation of adult human myoblasts induced by ciliary neurotrophic factor in vitro. Moll Biol Cell. 16: 3140-3151.
Chen XF, et al. (2008) Dynamic simulation of the effect of calcium-release activated calcium channel on cytoplasmic $Ca^{2+}$ oscillation. Biophys Chem. 136: 87-95.
Chen XP, (2003) [Exogenous rhCNTF inhibits myoblast differentiation of skeletal muscle of adult human in vitro]. Sheng Li Xue Bao. 55: 464-468.
Chiu AY, et al. (1993) A motor neuron-specific epitope and the low-affinity nerve growth factor receptor display reciprocal patterns of expression during development, axotomy, and regeneration. J Comp Neurol. 328: 351-363.
Choi-Lundberg DL and Bohn MC. (1995) Ontogeny and distribution of glial cell line-derived neurotrophic factor (GDNF) mRNA in rat. Brain Res Dev Brain Res. 85: 80-88.
Choudhury A, et al. (2007) A piezoresistive microcantilever array for surface stress measurement: curvature model and fabrication. J Micromech Microeng. 17: 2065-2076.
Chow I, et al. (1985) Release of acetylcholine from embryonic neurons upon contact with muscle cell. J Neurosci. 5: 1076-1082.
Christ B, et al. (2002) Limb muscle development. Int J Dev Biol. 46: 905-914.
Cizkova D, et al. (2007) Functional recovery in rats with ischemic paraplegia after spinal grafting of human spinal stem cells. Neuroscience. 147: 546-560.
Clegg CH, et al. (1987) Growth factor control of skeletal muscle differentiation: commitment to terminal differentiation occurs in G1 phase and is repressed by fibroblast growth factor. J Cell Biol. 105: 949-956.
Clements JD, et al. (1992) The time course of glutamate in the synaptic cleft. Science. 258: 1498-1501.
Coggan JS, et al. (2005) Evidence for ectopic neurotransmission at a neuronal synapse. Science. 309: 446-451.
Cohen RI and Almazan G. (1993) Norepinephrine-stimulated PI hydrolysis in oligodendrocytes is mediated by alpha 1A-adrenoceptors. Neuroreport. 4: 1115-1118.
Cohen-Cory S. (2002) The developing synapse: construction and modulation of synaptic structures and circuits. Science. 298: 770-776.
Collins CA and Morgan JE. (2003) Duchenne's muscular dystrophy: animal models used to investigate pathogenesis and develop therapeutic strategies. Int J Exp Pathol. 84: 165-172.
Colomar A and Robitaille R. (2004) Glial modulation of synaptic transmission at the neuromuscular junction. Glia. 47: 284-289.
Cooper A, et al. (1976) the growth of mouse neuroblastoma cells in controlled orientations on thin films of silicon monoxide. Exp Cell Res. 103: 435-439.
Corey JM, et al. (1991) Compliance of hippocampal neurons to patterned substrate networks. J Neurosci Res. 30: 300-307.
Corey JM, et al. (1996) Micrometer resolution silane-based patterning of hippocampal neurons: critical variables in photoresist and laser ablation processes for substrate fabrication. IEEE Trans Biomed Eng. 43: 944-955.
Corey JM, et al. (1997) Differentiated B104 neuroblastoma cells are a high-resolution assay for micropatterned substrates. J Neurosci Methods. 75: 91-97.
Cortassa S, et al. (2003) An integrated model of cardiac mitochondrial energy metabolism and calcium dynamics. Biophys J. 84: 2734-2755.
Cossu G, et al. (1996) How is myogenesis initiated in the embryo? Trends Genet. 12: 218-223.
Courdier-Fruh I, et al. (2002) Glucocorticoid-mediated regulation of utrophin levels in human muscle fibers. Neuromuscul Disord. 12(Suppl 1): S95-S104.
Cross-Doersen D and Isfort RJ. (2003) A novel cell-based system for evaluating skeletal muscle cell hypertrophy-inducing agents. In Vitro Cell Dev Biol Animal. 39: 407-412.
Cukierman E, et al. (2002) Cell interactions with three-dimensional matrices. Curr Opin Cell Biol. 14: 633-639.
Cunningham JJ and Roussel MF. (2001) Cyclin-dependent kinase inhibitors in the development of the central nervous system. Cell Growth Differ. 12: 387-396.
Cuppini R, et al. (2001) Alpha-tocopherol controls cell proliferation in the adult rat dentate gyms. Neurosci Lett. 303: 198-200.
Currie PD and Ingham PW. (1996) Induction of a specific muscle cell type by a hedgehog-like protein in zebrafish. Nature. 382: 452-455.
Curtis R, et al. (1988) Development of macroglial cells in rat cerebellum. I. Use of antibodies to follow early in vivo development and migration of oligodendrocytes. J Neurocytol. 17: 43-54.
Cysyk J and Tung L. (2008) Electric field perturbations of spiral waves attached to millimeter-size obstacles. Biophys J. 94: 1533-1541.

(56) References Cited

OTHER PUBLICATIONS

Dakhel Y and Jamali F. (2006) Erythromycin potentiates PR interval prolonging effect of verapamil in the rat: a pharmacodynamic drug interaction. Toxicol Appl Pharmacol. 214: 24-29.
Daniels MP, et al. (2000) Rodent nerve-muscle cell culture system for studies of neuromuscular junction development: refinements and applications. Microsc Res Tech. 49: 26-37.
Daniels MP. (1990) Localization of actin, beta-spectrin, 43 × 10(3) Mr and 58 × 10(3) Mr proteins to receptor-enriched domains of newly formed acetylcholine receptor aggregates in isolated myotube membranes. J Cell Sci. 97(Pt 4): 615-626.
Daniels MP. (1997) Intercellular communication that mediates formation of the neuromuscular junction. Mol Neurobiol. 14: 143-170.
Das M, et al. (2003) Electrophysiological and morphological characterization of rat embryonic motoneurons in a defined system. Biotechnol Prog. 19: 1756-1761.
Das M, et al. (2004) Long-term culture of embryonic rat cardiomyocytes on an organosilane surface in a serum-free medium. Biomaterials. 25: 5643-5647.
Das M, et al. (2005) Adult rat spinal cord culture on an organosilane surface in a novel serum-free medium. In Vitro Cell Dev Biol Anim. 41: 343-348.
Das M, et al. (2006) A defined system to allow skeletal muscle differentiation and subsequent integration with silicon microstructures. Biomaterials. 27: 4374-4380.
Das M, et al. (2007a) Auto-catalytic ceria nanoparticles offer neuroprotection to adult rat spinal cord neurons. Biomaterials. 28: 1918-1925.
Das M, et al. (2007b) Differentiation of skeletal muscle and integration of myotubes with silicon microstructures using serum-free medium and a synthetic silane substrate. Nat Protoc. 2: 1795-1801.
Das M, et al. (2007c) Embryonic motoneuron-skeletal muscle co-culture in a defined system. Neuroscience. 146: 481-488.
Das M, et al. (2008) Temporal neurotransmitter conditioning restores the functional activity of adult spinal cord neurons in long-term culture. Exp Neurol. 209: 171-180.
Das M, et al. (2009a) Developing a novel serum-free cell culture model of skeletal muscle differentiation by systematically studying the role of different growth factors in myotube formation. In Vitro Cell Dev Biol Anim. 45: 378-387.
Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.
Das M, et al. (2010) A defined long-term in vitro tissue engineered model of neuromuscular junctions. Biomaterials. 31: 4880-4888.
Datar R, et al. (2009) Cantilever Sensors: Nanomechanical Tools for Diagnostics. MRS Bulletin. 34: 449-454.
David JA and Pitman RM. (1982) The effects of axotomy upon the extrasynaptic acetylcholine sensitivity of an identified motoneurone in the cockroach Periplaneta americana. J Exp Biol. 98: 329-341.
Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.
De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.
De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.
de Lange P, et al. (2006) Sequential changes in the signal transduction responses of skeletal muscle following food deprivation. FASEB J. 20: 2579-2581.
de Wilde J, et al. (2008) Short-term high fat-feeding results in morphological and metabolic adaptations in the skeletal muscle of C57BL/6J mice. Physiol Genomics. 32: 360-369.

Dell'Era P, et al. (2003) Fibroblast growth factor receptor-1 is essential for in vitro cardiomyocyte development. Circ Res. 93: 414-420.
Denning C and Anderson D. (2008) Cardiomyocytes from human embryonic stem cells as predictors of cardiotoxicity. Drug Discovery Today: Therapeutic Strategies. 5: 223-232.
Dennis RG and Kosnik IPE. (2000) Excitability and isometric contractile properties of mammalian skeletal muscle constructs engineered in vitro. In Vitro Cell Dev Biol Anim. 36: 327-335.
Dennis RG, et al. (2001) Excitability and contractility of skeletal muscle engineered from primary cultures and cell lines. Am J Physiol Cell Physiol. 280: C288-C295.
Denyer MCT, et al. (1998) Preliminary study on the suitability of a pharmacological bio-assay based on cardiac myocytes cultured over microfabricated microelectrode arrays. Med Biol Eng Comput. 36: 638-644.
Descarries L, et al. (1997) Diffuse transmission by acetylcholine in the CNS. Prog Neurobiol. 53: 603-625.
Dhavan R and Tsai L. (2001) A decade of CDK5. Nat Rev Mol Cell Biol. 2: 749-759.
Dhir V, et al. (2009) Patterning of diverse mammalian cell types in serum free medium with photoablation. Biotechnol Prog. 25: 594-603.
Di Giovanni S, et al. (2005) Cell cycle inhibition provides neuroprotection and reduces glial proliferation and scar formation after traumatic brain injury. Proc Natl Acad Sci U S A. 102: 8333-8338.
Dimitrova DS and Gilbert DM. (2000) Temporally coordinated assembly and disassembly of replication factories in the absence of DNA synthesis. Nat Cell Biol. 2: 686-694.
Djouhri L and Lawson SN. (1999) Changes in somatic action potential shape in guinea-pig nociceptive primary afferent neurones during inflammation in vivo. J Physiol. 520 Pt 2: 565-576.
Dolcet X, et al. (2001) Cytokines promote motoneuron survival through the Janus kinase-dependent activation of the phosphatidylinositol 3-kinase pathway. Mol Cell Neurosci. 18: 619-631.
Du Y, et al. (2006) Distinct effects of p75 in mediating actions of neurotrophins on basal forebrain oligodendrocytes. Mol Cell Neurosci. 31: 366-375.
Dulcey CS, et al. (1991) Deep UV photochemistry of chemisorbed monolayers: patterned coplanar molecular assemblies. Science. 252: 551-554.
Dumont RJ, et al. (2001) Acute spinal cord injury, part I: pathophysiologic mechanisms. Clin Neuropharmacology. 24: 254-264.
Duport S, et al. (1999) A metallic multisite recording system designed for continuous long-term monitoring of electrophysiological activity in slice cultures. Biosens Bioelectron. 14: 369-376.
Dusterhoft S and Pette D. (1999) Evidence that acidic fibroblast growth factor promotes maturation of rat satellite-cell-derived myotubes in vitro. Differentiation. 65 : 161-169.
Dutton EK, et al. (1995) Acetylcholine receptor aggregation at nerve-muscle contacts in mammalian cultures: induction by ventral spinal cord neurons is specific to axons. J Neurosci. 15: 7401-7416.
Edwards D, et al. (2010) Addition of glutamate to serum-free culture promotes recovery of electrical activity in adult hippocampal neurons in vitro. J Neurosci Methods. 190: 155-163.
Egert U, et al. (1998) A novel organotypic long-term culture of the rat hippocampus on substrate-integrated multielectrode arrays. Brain Res Brain Res Protoc. 2: 229-242.
Egert U, et al. (2006) Analysis of cardiac myocyte activity dynamics with microeletrode arrays. In: Taketani M BM, editor. Advances in netwrok electrophysiology using multi electrode arrays: Springer 2006. p. 274-290.
Eisen A and Swash M. (2001) Clinical neurophysiology of ALS. Clin Neurophysiol. 112: 2190-2201.
Eisenberg T, et al. (2009) Induction of autophagy by spermidine promotes longevity. Nat Cell Biol. 11: 1305-1314.
Eldridge CF, et al. (1989) Differentiation of axon-related Schwann cells in vitro: II. Control of myelin formation by basal lamina. J Neurosci. 9: 625-638.

(56) References Cited

OTHER PUBLICATIONS

Elia D, et al. (2007) Sonic hedgehog promotes proliferation and differentiation of adult muscle cells: Involvement of MAPK/ERK and PI3K/Akt pathways. Biochim Biophys Acta. 1773: 1438-1446.
Emery AEH. (2002) The muscular dystrophies. Lancet. 359: 687-695.
Engler AJ, et al. (2006) Matrix elasticity directs stem cell lineage specification. Cell. 126: 677-689.
English AW. (2003) Cytokines, growth factors and sprouting at the neuromuscular junction. J Neurocytol. 32: 943-960.
Entcheva EK, et al. (2004) Fluorescence imaging of electrical activity in cardiac cells using an all-solid-state system. IEEE Trans Biomed Eng. 51: 331-341.
Ericson J, et al. (1992) Early stages of motor neuron differentiation revealed by expression of homeobox gene Islet-1. Science. 256: 1555-1560.
Esch MB, et al. (2011) The role of body-on-a-chip devices in drug and toxicity studies. Annu Rev Biomed Eng. 13: 55-72.
Esch MB, et al. (2012) On chip porous polymer membranes for integration of gastrointestinal tract epithelium with microfluidic 'body-on-a-chip' devices. Biomed Microdevices. 14: 895-906.
Eschenhagen T and Zimmermann WH. (2005) Engineering myocardial tissue. Circ Res. 97: 1220-1231.
Evans MS, et al. (1998) Electrophysiology of embryonic, adult and aged rat hippocampal neurons in serum-free culture. J Neurosci Methods. 79: 37-46.
Fan CM and Tessier-Lavigne M. (1994) Patterning of mammalian somites by surface ectoderm and notochord: evidence for sclerotome induction by a hedgehog homolog. Cell. 79: 1175-1186.
Faraut B, et al. (2004) Thrombin reduces MuSK and acetylcholine receptor expression along with neuromuscular contact size in vitro. Eur J Neurosci. 19: 2099-2108.
FDA (2004) Innovation or Stagnation: Challenge and Opportunity on the Critical Path to New Medical Products.
Fernandez-Valle C, et al. (1993) Expression of the protein zero myelin gene in axon-related Schwann cells is linked to basal lamina formation. Development. 119: 867-880.
Fernandez-Valle C, et al. (1995) Schwann cells degrade myelin and proliferate in the absence of macrophages: evidence from in vitro studies of Wallerian degeneration. J Neurocytol. 24: 667-679.
Fields GB, et al. (1998) Protein-like molecular architecture: biomaterial applications for inducing cellular receptor binding and signal transduction. Biopolymers. 47: 143-151.
Fields GB. (1999) Induction of protein-like molecular architecture by self-assembly processes. Bioorg Med Chem. 7: 75-81.
Figenschou A, et al. (1996) Cholinergic modulation of the action potential in rat hippocampal neurons. Eur J Neurosci. 8: 211-219.
Fink CC, et al. (1999) Determination of time-dependent inositol-1,4,5-trisphosphate concentrations during calcium release in a smooth muscle cell. Biophys J. 77: 617-628.
Fischbach GD and Cohen SA. (1973) The distribution of acetylcholine sensitivity over uninnervated and innervated muscle fibers grown in cell culture. Dev Biol. 31: 147-162.
Fischbach GD. (1972) Synapse formation between dissociated nerve and muscle cells in low density cell cultures. Dev Biol. 28: 407-429.
Fisher OZ, et al. (2010) Bioinspired materials for controlling stem cell fate. Acc Chem Res. 43: 419-428.
Fishman RA. (2002) The cerebrospinal fluid production rate is reduced in dementia of the Alzheimer's type. Neurology. 58: 1866; author reply 1866.
Flucher BE, et al. (1990) Localization of the alpha 1 and alpha 2 subunits of the dihydropyridine receptor and ankyrin in skeletal muscle triads. Neuron. 5: 339-351.
Flucher BE, et al. (1991) Biogenesis of transverse tubules in skeletal muscle in vitro. Dev Biol. 145: 77-90.
Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.
Flucher BE, et al. (1994) Molecular organization of transverse tubule/sarcoplasmic reticulum junctions during development of excitation-contraction coupling in skeletal muscle. Mol. Biol Cell. 5: 1105-1118.
Forry SP, et al. (2006) Facilitating the culture of mammalian nerve cells with polyelectrolyte multilayers. Langmuir. 22: 5770-5775.
Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.
Fowler VM, et al. (1993) Tropomodulin is associated with the free (pointed) ends of the thin filaments in rat skeletal muscle. J Cell Biol. 120: 411-420.
Fox MA, et al. (2007) Distinct target-derived signals organize formation, maturation, and maintenance of motor nerve terminals. Cell. 129: 179-193.
Francis PT. (2008) Glutamatergic approaches to the treatment of cognitive and behavioural symptoms of Alzheimer's disease. Neurodegener Dis. 5: 241-243.
Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.
Franzini-Armstrong C and Protasi F. (1997) Ryanodine receptors of striated muscles: a complex channel capable of multiple interactions. Physiol Rev. 77: 699-729.
Friedman B, et al. (1995) BDNF and NT-4/5 exert neurotrophic influences on injured adult spinal motor neurons. J Neurosci. 15: 1044-1056.
Fu X, et al. (1995) Acidic fibroblast growth factor reduces rat skeletal muscle damage caused by ischemia and reperfusion. Chin Med J (Engl). 108: 209-214.
Fuentes-Medel Y, et al. (2012) Integration of a retrograde signal during synapse formation by glia-secreted TGF-β ligand. Curr Biol. 22: 1831-1838.
Funakoshi H, et al. (1995) Muscle-derived neurotrophin-4 as an activity-dependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175: 50-57.
Galizia CG and Menzel R. (2000) Probing the olfactory code. Nat Neurosci. 3: 853-854.
Gao BX and Ziskind-Conhaim L. (1995) Development of glycine- and GABA-gated currents in rat spinal motoneurons. J Neurophysiol. 74: 113-121.
Gao Bx and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69: 4027-4037.
Gaud A, et al. (2004) Prednisone reduces muscle degeneration in dystrophin-deficient Caenorhabditis elegans. Neuromuscul Disord. 14: 365-370.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.

(56) References Cited

OTHER PUBLICATIONS

Ghiani CA, et al. (1999) Neurotransmitter receptor activation triggers p27(Kip1)and p21(CIP1) accumulation and G1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass L and Kauffman SA. (1973) The logical analysis of continuous, non-linear biochemical control networks. J Theor Biol. 39: 103-129.
Glass L. (1975) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF family-receptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.
Greenstein JL and Winslow RL. (2002) An integrative model of the cardiac ventricular myocyte incorporating local control of Ca2+ release. Biophys J. 83: 2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374: 1745-1753.

Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNP1. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in APP + PS1 transgenic mice. Neurobiol Dis. 15: 188-195.
Haas HL and Selbach O. (2000) Functions of neuronal adenosine receptors. Naunyn Schmiedebergs Arch Pharmacol. 362: 375-381.
Halbach M, et al. (2003) Estimation of action potential changes from field potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.
Han DK and Hubbell JA. (1997) Synthesis of Polymer Network Scaffolds from 1-Lactide and Poly(ethylene glycol) and Their Interaction with Cells. Macromolecules. 30: 607-6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived motoneurons in vitro and in motoneuron-injured adult rats. Proc Natl Acad Sci U S A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.

(56) References Cited

OTHER PUBLICATIONS

Henderson CE, et al. (1993) Neurotrophins promote motor neuron survival and are present in embryonic limb bud. Nature. 363: 266-270.
Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction-enhancement technique. J Appl Physiol. 82: 1739-1742.
Hennessey JV, et al. (2001) Growth hormone administration and exercise effects on muscle fiber type and diameter in moderately frail older people. J Am Geriatr Soc. 49: 852-858.
Hermann M, et al. (2006) Exposure of atorvastatin is unchanged but lactone and acid metabolites are increased several-fold in patients with atorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.
Hickman J, et al. (1993) The use of monlayers as templates for biocompatibility studies. Abstracts of Papers of the American Chemical Society. 205: 146—Coll.
Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.
Hickman JJ, et al. (1994) Rational Pattern Design for in-Vitro Cellular Networks Using Surface Photochemistry. J Vac Science Technol A. 12: 607-616.
Hirano A. (1968) A confirmation of the oligodendroglial origin of myelin in the adult rat. J Cell Biol. 38: 637-640.
Hjerling-Leffler J, et al. (2005) The boundary cap: a source of neural crest stem cells that generate multiple sensory neuron subtypes. Development. 132: 2623-2632.
Hoffman EP and Escolar D. (2006) Translating mighty mice into neuromuscular therapeutics: is bigger muscle better? Am J Pathol. 168: 1775-1778.
Hofmann F and Bading H. (2006) Long term recordings with microelectrode arrays: studies of transcription-dependent neuronal plasticity and axonal regeneration. J Physiol Paris. 99: 125-132.
Holleran AL, et al. (1995) Glutamine metabolism in AS-30D hepatoma cells. Evidence for its conversion into lipids via reductive carboxylation. Mol Cell Biochem. 152: 95-101.
Hondeghem LM and Hoffman P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.
Hondeghem LM, et al. (2001) Instability and triangulation of the action potential predict serious proarrhythmia, but action potential duration prolongation is antiarrhythmic. Circulation. 103: 2004-2013.
Hondeghem LM, et al. (2003a) Detection of proarrhythmia in the female rabbit heart: blinded validation. J Cardiovasc Electrophysiol. 14: 287-294.
Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.
Hondeghem LM. (2007) Relative contributions of TRIaD and QT to proarrhythmia. J Cardiovasc Electrophysiol. 18: 655-657.
Hsiao CF, et al. (2005) Voltage-dependent calcium currents in trigeminal motoneurons of early postnatal rats: modulation by 5-HT receptors. J Neurophysiol. 94: 2063-2072.
Hu BY, et al. (2009) Human oligodendrocytes from embryonic stem cells: conserved SHH signaling networks and divergent FGF effects. Development. 136: 1443-1452.
Hua JY and Smth SJ. (2004) Neural activity and the dynamics of central nervous system development. Nat Neurosci. 7: 327-332.

Huang Y, et al. (2007) An alpha1A-adrenergic-extracellular signal-regulated kinase survival signaling pathway in cardiac myocytes. Circulation. 115: 763-772.
Huang YC, et al. (2005) Rapid formation of functional muscle in vitro using fibrin gels. J Appl Physiol. 98: 706-713.
Hucka M, et al. (2003) The systems biology markup language (SBML): a medium for representation and exchange of biochemical network models. Bioinformatics. 19: 524-531.
Hughes B. (2008) 2007 FDA drug approvals: a year of flux. Nat Rev Drug Discov. 7: 107-109.
Huh D, et al. (2010) Reconstituting organ-level lung functions on a chip. Science. 328: 1662-1668.
Huh D, et al. (2012) Microengineered physiological biomimicry: organs-on-chips. Lab Chip. 12: 2156-2164.
Hui EE and Bhatia SN. (2007) Microscale control of cell contact and spacing via three-component surface patterning. Langmuir. 23: 4103-4107.
Hung SC, et al. (2002) In vitro differentiation of size-sieved stem cells into electrically active neural cells. Stem Cells. 20: 522-529.
Husmann I, et al. (1996) Growth factors in skeletal muscle regeneration. Cytokine Growth Factor Rev. 7: 249-258.
Huxley, A. F. (1975). The origin of force in skeletal muscle. Ciba Found Symp. 31: 271-290.
Ichikawa H, et al. (2004) Effect of Brn-3a deficiency on parvalbumin-immunoreactive primary sensory neurons in the dorsal root ganglion. Brain Res Dev Brain Res. 150: 41-45.
Inoue N, et al. (2004) Rapid electrical stimulation of contraction modulates gap junction protein in neonatal rat cultured cardiomyocytes: involvement of mitogen-activated protein kinases and effects of angiotensin II-receptor antagonist. J Am Coll Cardiol. 44: 914-922.
Iravanian S, et al. (2003) Functional reentry in cultured monolayers of neonatal rat cardiac cells. Am J Physiol Heart Circ Physiol. 285: H449-H456.
Ito Y. (1999) Surface micropatterning to regulate cell functions. Biomaterials. 20: 2333-2342.
Izrael M, et al. (2007) Human oligodendrocytes derived from embryonic stem cells: Effect of noggin on phenotypic differentiation in vitro and on myelination in vivo. Mol Cell Neurosci. 34: 310-323.
Izumiya Y, et al. (2008) Fast/glycolytic muscle fiber growth reduces fat mass and improves metabolic parameters in obese mice. Cell Metabolism. 7: 159-172.
Jackson JH 4th, et al. (2004) Assessment of drug therapy management and the prevalence of heart failure in a managed care population with hypertension. J Manag Care Pharm. 10: 513-520.
Jaworska-Wilczynska M, et al. (2002) Three lipoprotein receptors and cholesterol in inclusion-body myositis muscle. Neurology. 58: 438-445.
Jensen J, et al. (2009) Human embryonic stem cell technologies and drug discovery. J Cell Physiol. 219: 513-519.
Jessen KR and Mirsky R. (2005) The origin and development of glial cells in peripheral nerves. Nat Rev Neurosci. 6: 671-682.
Jevsek M, et al. (2004) Origin of acetylcholinesterase in the neuromuscular junction formed in the in vitro innervated human muscle. Eur J Neurosci. 20: 2865-2871.
Jhamandas JH, et al. (2001) Cellular mechanisms for amyloid beta-protein activation of rat cholinergic basal forebrain neurons. J Neurophysiol. 86: 1312-1320.
Jiang XH, et al. (2009) Isolation and characterization of neural crest stem cells derived from in vitro-differentiated human embryonic stem cells. Stem Cells Dev. 18: 1059-1070.
Jiang Z and Clemens PR. (2006) Cellular caspase-8-like inhibitory protein (cFLIP) prevents inhibition of muscle cell differentiation induced by cancer cells. FASEB J. 20: 2570-2572.
Jiang ZG, et al. (1990) Excitatory and inhibitory transmission from dorsal root afferents to neonate rat motoneurons in vitro. Brain Res. 535: 110-118.
Jin P, et al. (1991) Recombinant platelet-derived growth factor-BB stimulates growth and inhibits differentiation of rat L6 myoblasts. J Biol Chem. 266: 1245-1249.

(56) References Cited

OTHER PUBLICATIONS

Johnson TE, et al. (2005) Statins and PPARalpha agonists induce myotoxicity in differentiated rat skeletal muscle cultures but do not exhibit synergy with cotreatment. Toxicol Appl Pharmacol. 208: 210-221.
Julius D and Basbaum AI. (2001) Molecular mechanisms of nociception. Nature. 413: 203-210.
Jung DR, et al. (1998) Cell-Based Sensor Microelectrode Array Characterized by Imaging X-ray Photoelectron Spectroscopy, Scanning Electron Microscopy, Impedance Measurements, and Extracellular Recordings. Journal of Vacuum Science & Technology A (Vacuum, Surfaces, and Films). 16: 1183-1188.
Jung DR, et al. (2001) Topographical and physicochemical modification of material surface to enable patterning of living cells. Crit Rev Biotechnol. 21: 111-154.
Jurdana M, et al. (2009) Neural agrin changes the electrical properties of developing human skeletal muscle cells. Cell Mol Neurobiol. 29: 123-131.
Kaeberlein M. (2009) Spermidine surprise for a long life. Nat Cell Biol. 11: 1277-1278.
Kaji H, et al. (2003) Pharmacological characterization of micropatterned cardiac myocytes. Biomaterials. 24: 4239-4244.
Kamp TJ. (2009) Human pluripotent stem cell-derived cardiomyocytes for safety pharmacology applications. Journal of Pharmacological and Toxicological Methods. 60: 259.
Kane RS, et al. (1999) Patterning proteins and cells using soft lithography. Biomaterials. 20: 2363-2376.
Kang JH, et al. (2009) In vitro 3D model for human vascularized adipose tissue. Tissue Eng Part A. 15: 2227-2236.
Kato AC and Lindsay RM. (1994) Overlapping and additive effects of neurotrophins and CNTF on cultured human spinal cord neurons. Exp Neurol. 130: 196-201.
Katsuki H, et al. (2000) Distinct signaling pathways involved in multiple effects of basic fibroblast growth factor on cultured rat hippocampal neurons. Brain Res. 885: 240-250.
Katz LC and Shatz CJ. (1996) Synaptic activity and the construction of cortical circuits. 274: 1133-1138.
Kauffman S, et al. (2003) Random Boolean network models and the yeast transcriptional network. Proc Natl Acad Sci U S A. 100: 14796-14799.
Kauffman S. (1971) Gene regulation networks: a theory for their global structure and behaviors. Curr Top Dev Biol. 6: 145-182.
Kaufmann P, et al. (2006) Toxicity of statins on rat skeletal muscle mitochondria. Cell Mol Life Sci. 63: 2415-2425.
Keefer EW, et al. (2001) Acute toxicity screening of novel AChE inhibitors using neuronal networks on microelectrode arrays. Neurotoxicology. 22: 3-12.
Keefer EW, et al. (2001) Characterization of acute neurotoxic effects of trimethylolpropane phosphate via neuronal network biosensors. Biosens Bioelectron. 16: 513-525.
Kessaris N, et al. (2008) Specification of CNS glia from neural stem cells in the embryonic neuroepithelium. Philos Trans R Soc Lond B Biol Sci. 363: 71-85.
Khademhosseini A, et al. (2006a) Interplay of biomaterials and micro-scale technologies for advancing biomedical applications. J Biomater Sci Polym Ed. 17: 1221-1240.
Khademhosseini A, et al. (2006b) Microscale technologies for tissue engineering and biology. Proc Natl Acad Sci USA. 103: 2480-2487.
Khorchid A, et al. (1999) Characterization of the signal transduction pathways mediating noradrenaline-stimulated MAPK activation and c-fos expression in oligodendrocyte progenitors. J Neurosci Res. 58: 765-778.
Khorchid A, et al. (2002) Developmental regulation of alpha 1A-adrenoceptor function in rat brain oligodendrocyte cultures. Neuropharmacology. 42: 685-696.
Kidambi S, et al. (2004) Controlling primary hepatocyte adhesion and spreading on protein-free polyelectrolyte multilayer films. J Am Chem Soc. 126: 16286-16287.
Kidambi S, et al. (2007a) Patterned co-culture of primary hepatocytes and fibroblasts using polyelectrolyte multilayer templates. Macromol Biosci. 7: 344-353.
Kidambi S, et al. (2007b) Cell adhesion on polyelectrolyte multilayer coated polydimethylsiloxane surfaces with varying topographies. Tissue Eng. 13: 2105-2117.
Kidd, J. (2006). Life after statin patent expiries. Nat Rev Drug Discov. 5: 813-814.
Kim C, et al. (2010) Non-cardiomyocytes influence the electrophysiological maturation of human embryonic stem cell-derived cardiomyocytes during differentiation. Stem Cells Dev. 19: 783-795.
Kim J, et al. (2002) Dopamine neurons derived from embryonic stem cells function in an animal model of Parkinson's disease. Nature. 418: 50-56.
Kim K, et al. (2011) Calibrated micropost arrays for biomechanical characterization of cardiomyocytes. Micro and Nano Letters. 6: 317-322.
Kim SU, et al. (2002) Production of immortalized human neural crest stem cells. Methods Mol Biol. 198: 55-65.
King T, et al. (2000) Piezoactuators for 'real-world' applications—Can they deliver sufficient displacement? Power Engineering. 14: 105-110.
Kingshott P and Griesser HJ. (1999) Surfaces that resist bioadhesion. Current Opinion in Solid State and Materials Science. 4: 403-412.
Kirazov E, et al. (2008) Amyloid beta peptides exhibit functional neurotoxicity to cortical network cultures. Compt Rend Acad Bulg Sci. 61: 905-910.
Kita-Matsuo H, et al. (2009) Lentiviral vectors and protocols for creation of stable hESC lines for fluorescent tracking and drug resistance selection of cardiomyocytes. PLoS One. 4: e5046.
Kleber AG and Rudy Y. (2004) Basic mechanisms of cardiac impulse propagation and associated arrhythmias. Physiol Rev. 84: 431-488.
Klein C, et al. (2002) Zinc inhibition of cAMP signaling. J Biol Chem. 277: 11859-11865.
Klein WL. (2002) Abeta toxicity in Alzheimer's disease: globular oligomers (ADDLs) as new vaccine and drug targets. Neurochem Int. 41: 345-352.
Kleinfeld D, et al. (1988) Controlled outgrowth of dissociated neurons on patterned substrates. J Neurosci. 8: 4098-4120.
Knobloch M and Mansuy IM. (2008) Dendritic spine loss and synaptic alterations in Alzheimer's disease. Mol Neurobiol. 37: 73-82.
Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.
Kobayashi T, et al. (1987) Human muscle cultured in monolayer and cocultured with fetal rat spinal cord: importance of dorsal root ganglia for achieving successful functional innervation. J Neurosci. 7: 3131-3141.
Koike T, et al. (2008) Axon & dendrite degeneration: its mechanisms and protective experimental paradigms. Neurochem Int. 52: 751-760.
Koirala S, et al. (2003) Roles of glial cells in the formation, function, and maintenance of the neuromuscular junction. J Neurocytol. 32: 987-1002.
Koleva M, et al. (2005) Pleiotropic effects of sonic hedgehog on muscle satellite cells. Cell Mol Life Sci. 62: 1863-1870.
Koliatsos VE, et al. (2008) Human stem cell grafts as therapies for motor neuron disease. Expert Opin Biol Ther. 8: 137-141.
Kontrogianni-Konstantopoulos A, et al. (2009) Muscle giants: molecular scaffolds in sarcomerogenesis. Physiol Rev. 89: 1217-1267.
Kornblum HI, et al. (1999) Multiple trophic actions of heparin-binding epidermal growth factor (HB-EGF) in the central nervous system. Eur J Neurosci. 11: 3236-3246.
Kucera J and Dorovini-Zis K. (1979). Types of human intrafusal muscle fibers. Muscle Nerve. 2: 437-451.
Kucera J and Walro J. (1992) Axotomy induces fusimotor-free muscle spindles in neonatal rats. Neurosci Lett. 136: 216-218.

(56) References Cited

OTHER PUBLICATIONS

Kucera J, et al. (1989) Role of nerve and muscle factors in the development of rat muscle spindles. Am J Anat. 186: 144-160.
Kucera J. (1982a) One-bag-fiber muscle spindles in tenuissimus muscles of the cat. Histochemistry and Cell Biology. 76: 315-328.
Kucera, J. (1982b). The topography of long nuclear chain intrafusal fibers in the cat muscle spindle. Histochemistry. 74: 183-197.
Kucera, J. (1983). Multiple-bag-fiber muscle spindles in tenuissimus muscles of the cat. Histochemistry. 79: 457-476.
Kudla AJ, et al. (1995) A requirement for fibroblast growth factor in regulation of skeletal muscle growth and differentiation cannot be replaced by activation of platelet-derived growth factor signaling pathways. Mol Cell Biol. 15: 3238-3246.
Kuhl U, et al. (1982) Synthesis of type IV collagen and laminin in cultures of skeletal muscle cells and their assembly on the surface of myotubes. Dev Biol. 93: 344-354.
Kuhl U, et al. (1986) Role of laminin and fibronectin in selecting myogenic versus fibrogenic cells from skeletal muscle cells in vitro. Dev Biol. 117: 628-635.
Kumar S, et al. (1998) NT-3-mediated TrkC receptor activation promotes proliferation and cell survival of rodent progenitor oligodendrocyte cells in vitro and in vivo. J Neurosci Res. 54: 754-765.
Kurek JB, et al. (1996) Leukemia inhibitory factor and interleukin-6 are produced by diseased and regenerating skeletal muscle. Muscle Nerve. 19: 1291-1301.
Lacor PN, et al. (2007) Abeta oligomer-induced aberrations in synapse composition, shape, and density provide a molecular basis for loss of connectivity in Alzheimer's disease. J Neurosci. 27: 796-807.
Lacor PN. (2007) Advances on the understanding of the origins of synaptic pathology in AD. Curr Genomics. 8: 486-508.
Laflamme MA, et al. (2007) Cardiomyocytes derived from human embryonic stem cells in pro-survival factors enhance function of infarcted rat hearts. Nat Biotechnol. 25: 1015-1024.
Lamb TM, et al. (1993) Neural induction by the secreted polypeptide noggin. Science. 262: 713-718.
Lambert MP, et al. (1998) Diffusible, nonfibrillar ligands derived from Abetal—42 are potent central nervous system neurotoxins. Proc Natl Acad Sci U S A. 95: 6448-6453.
Lambeth MJ and Kushmerick MJ. (2002) A computational model for glycogenolysis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.
Langen RC, et al. (2003) Enhanced myogenic differentiation by extracellular matrix is regulated at the early stages of myogenesis. In Vitro Cell Dev Biol Anim. 39: 163-169.
Langer R and Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proarrhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.
Lee HY, et al. (2004) Instructive role of Wnt/beta-catenin in sensory fate specification in neural crest stem cells. Science. 303: 1020-1023.
Lee MJ, et al. (2003) Hereditary sensory neuropathy is caused by a mutation in the delta subunit of the cytosolic chaperonin-containing t-complex peptide-1 (Cct4 ) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation of NMDA receptors by cyclin-dependent kinase-5. Proc Natl Acad Sci U S A. 98: 12742-12747.
Li L and Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4: e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. Curr Neurovasc Res. 3: 281-288.
Lin JW, et al. (2008) Region [corrected] of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations in DRG neurons: relation to neuropathic pain. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci U S A. 97: 6126-6131.

(56) References Cited

OTHER PUBLICATIONS

Liu TX, et al. (2006) Blinded validation of the isolated arterially perfused rabbit ventricular wedge in preclinical assessment of drug-induced proarrhythmias. Heart Rhythm. 3: 948-956.

Liu WP, et al. (2005) Enantioselectivity in environmental safety of current chiral insecticides. Proc Natl Acad Sci U S A. 102: 701-706.

Lochter AJ, et al. (1995) Control of neuronal morphology in vitro: interplay between adhesive substrate forces and molecular instruction. J Neurosci Res. 42: 145-158.

Long C, et al. (2012) Design optimization of liquid-phase flow patterns for microfabricated lung on a chip. Ann Biomed Eng. 40: 1255-1267.

Lou XJ. (2009) Polarization fatigue in ferroelectric thin films and related materials. Journal of Applied Physics. 105: 024101-024124.

Love S. (2003) Neuronal expression of cell cycle-related proteins after brain ischaemia in man. Neurosci Lett. 353: 29-32.

Lu B, et al. (1996) Expression of synapsin I correlates with maturation of the neuromuscular synapse. Neuroscience. 74: 1087-1097.

Lu HR, et al. (2006) In-vitro experimental models for the risk assessment of antibiotic-induced QT prolongation. Eur J Pharmacol. 553: 229-239.

Ludwig T and A Thomson J. (2007) Defined, feeder-independent medium for human embryonic stem cell culture. Curr Protoc Stem Cell Biol. Chapter 1: Unit 1C.2.

Lund AE and Narahashi T. (1982) Dose-dependent interaction of the pyrethroid isomers with sodium channels of squid axon membranes. Neurotoxicology. 3: 11-24.

Luo Y, et al. (2006) Effects of growth factors on extracellular matrix production by vocal fold fibroblasts in 3-dimensional culture. Tissue Eng. 12: 3365-3374.

Lyles JM, et al. (1992) Matrigel enhances myotube development in a serum-free defined medium. Int J Dev Neurosci. 10: 59-73.

Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.

Machida S, et al. (2004) Primary rat muscle progenitor cells have decreased proliferation and myotube formation during passages. Cell Prolif. 37: 267-277.

Maduell F. (2005) Hemodiafiltration. Hemodial Int. 9: 47-55.

Mahler GJ, et al. (2009a) Characterization of a gastrointestinal tract microscale cell culture analog used to predict drug toxicity. Biotechnol Bioeng. 104: 193-205.

Mahler GJ, et al. (2009b) Characterization of Caco-2 and HT29-MTX cocultures in an in vitro digestion/cell culture model used to predict iron bioavailability. J Nutr Biochem. 20: 494-502.

Malerba A, et al. (2009) Selection of multipotent cells and enhanced muscle reconstruction by myogenic macrophage-secreted factors. Exp Cell Res. 315: 915-927.

Malm C, et al. (2004) Leukocytes, cytokines, growth factors and hormones in human skeletal muscle and blood after uphill or downhill running J Physiol. 556: 983-1000.

Malo N, et al. (2006) Statistical practice in high-throughput screening data analysis. Nat Biotechnol. 24: 167-175.

Marhl M, et al. (2000) Complex calcium oscillations and the role of mitochondria and cytosolic proteins. Biosystems. 57: 75-86.

Marona HRN, et al. (1999) Determination of sparfloxacin and its degradation products by HPLC-PDA. J Antimicrob Chemother. 44: 301-302.

Marques MJ and Neto HS. (1997) Ciliary neurotrophic factor stimulates in vivo myotube formation in mice. Neurosci Lett. 234: 43-46.

Mars T, et al. (2001) Differentiation of glial cells and motor neurons during the formation of neuromuscular junctions in cocultures of rat spinal cord explant and human muscle. J Comp Neurol. 438: 239-251.

Mars T, et al. (2003) Functional innervation of cultured human skeletal muscle proceeds by two modes with regard to agrin effects. Neuroscience. 118: 87-97.

Martin-Caraballo M and Greer JJ. (2000) Development of potassium conductances in perinatal rat phrenic motoneurons. J Neurophysiol. 83: 3497-3508.

Martinou JC, et al. (1992) Cholinergic differentiation factor (CDF/LIF) promotes survival of isolated rat embryonic motoneurons in vitro. Neuron. 8: 737-744.

Masu Y, et al. (1993) Disruption of the CNTF gene results in motor neuron degeneration. Nature. 365: 27-32.

Matsakas A and Patel K. (2009) Skeletal muscle fibre plasticity in response to selected environmental and physiological stimuli. Histol Histopathol. 24: 611-629.

Matsuda T, et al. (1992) Two-dimensional cell manipulation technology. An artificial neural circuit based on surface microphotoprocessing. ASAIO J. 38: M243-M247.

Matthews PB. (1964) Muscle spindles and their motor control. Physiol Rev. 44: 219-288.

Mattson MP, et al. (1992) Beta-Amyloid Peptides Destabilize Calcium Homeostasis and Render Human Cortical-Neurons Vulnerable to Excitotoxicity. J Neurosci. 12: 376-389.

Matzno S, et al. (2003) Evaluation of the synergistic adverse effects of concomitant therapy with statins and fibrates on rhabdomyolysis. J Pharm Pharmacol. 55: 795-802.

Mayes L, et al. (2007) Pbx homeodomain proteins direct Myod activity to promote fast-muscle differentiation. Development. 134: 3371-3382.

Maynard EM. (2001) Visual prostheses. Annu Rev Biomed Eng. 3: 145-168.

McAuliffe GJ, et al. (2008) Development of a gastrointestinal tract microscale cell culture analog to predict drug transport. Mol Cell Biomech. 5: 119-132.

McBeath R, et al. (2004) Cell shape, cytoskeletal tension, and RhoA regulate stem cell lineage commitment. Dev Cell. 6: 483-495.

McDevitt TC, et al. (2002) In vitro generation of differentiated cardiac myofibers on micropatterned laminin surfaces. J Biomed Mater Res. 60: 472-479.

McMahon JA, et al. (1998) Noggin-mediated antagonism of BMP signaling is required for growth and patterning of the neural tube and somite. Genes Dev. 12: 1438-1452.

Megeney LA, et al. (1996) bFGF and LIF signaling activates STAT3 in proliferating myoblasts. Dev Genet. 19: 139-145.

Mehra S, et al. (2004) A boolean algorithm for reconstructing the structure of regulatory networks. Metab Eng. 6: 326-339.

Meijer L and Raymond E. (2003) Roscovitine and other purines as kinase inhibitors. From starfish oocytes to clinical trials. Acc Chem Res. 36: 417-425.

Melendez-Vasquez CV, et al. (2001) Nodes of Ranvier form in association with ezrin-radixin-moesin (ERM)-positive Schwann cell processes. Proc Natl Acad Sci U S A. 98: 1235-1240.

Mendelsohn JD, et al. (2003) Rational design of cytophilic and cytophobic polyelectrolyte multilayer thin films. Biomacromolecules. 2003 4: 96-106.

Menendez L, et al. (2011) Wnt signaling and a Smad pathway blockade direct the differentiation of human pluripotent stem cells to multipotent neural crest cells. Proc Natl Acad Sci U S A. 108: 19240-19245.

Menn B, et al. (2010) Delayed treatment with systemic (S)-roscovitine provides neuroprotection and inhibits in vivo CDK5 activity increase in animal stroke models. PLoS One. 5: e12117.

Metzger SW, et al. (1999) Development and characterization of surface chemistries for microfabricated biosensors. J of Vacuum Sci & Tech a-Vacuum Surfaces and Films. 17: 2623-2628.

Meyer G and Nabil MA. (1988) Novel optical approach to atomic force microscopy. Applied Physics Letters. 53: 1045-1047.

Meyer T, et al. (2004) Micro-electrode arrays in cardiac safety pharmacology—A novel tool to study QT interval prolongation. Drug Saf. 27: 763-772.

Meyer T, et al. (2004b) QT-screen: high-throughput cardiac safety pharmacology by extracellular electrophysiology on primary cardiac myocytes. Assay Drug Dev Technol. 2: 507-514.

Miles GB, et al. (2004) Functional properties of motoneurons derived from mouse embryonic stem cells. J Neurosci. 24: 7848-7858.

(56) References Cited

OTHER PUBLICATIONS

Miller FD. (2007) Riding the waves: neural and nonneural origins for mesenchymal stem cells. Cell Stem Cell. 1: 129-130.
Miller SC, et al. (1988) Tumor necrosis factor inhibits human myogenesis in vitro. Mol Cell Biol. 8: 2295-2301.
Mitsumoto H, et al. (2001) Effects of cardiotrophin-1 (CT-1) in a mouse motor neuron disease. Muscle Nerve. 24: 769-777.
Mizuseki K, et al. (2003) Generation of neural crest-derived peripheral neurons and floor plate cells from mouse and primate embryonic stem cells. Proc Natl Acad Sci U S A. 100: 5828-5833.
Moe GK. (1962) On the multiple wavelet hypothesis of atrial fibrillation. Arch Int Pharmacodyn Ther. 183-188.
Mohammed JS, et al. (2004) Micropatterning of nanoengineered surfaces to study neuronal cell attachment in vitro. Biomacromolecules. 5: 1745-1755.
Mohan DK, et al. (2006) Toxin detection based on action potential shape analysis using a realistic mathematical model of differentiated NG108-15 cells. Biosens Bioelectron. 21: 1804-1811.
Mokry J, et al. (2007) Differentiation of neural stem cells into cells of oligodendroglial lineage. Acta Medica (Hradec Kralove). 50: 35-41.
Molnar P, et al. (2005) Biosurface Engineering. Encyclopedia of Medical Devices and Instrumentation. J.G. Webster. New York, John Wiley & Sons, Inc.
Molnar P, et al. (2007) Photolithographic Patterning of C2C12 Myotubes using Vitronectin as Growth Substrate in Serum-Free Medium. Biotechnol Prog. 23: 265-268.
Molnar P, et al. (2007b) Synaptic connectivity in engineered neuronal networks. Methods Mol Biol. 403: 165-173.
Molnar P, et al. (2007c) Modeling of action potential generation in NG108-15 cells. Methods Mol Biol. 403: 175-184.
Monaco EA 3rd and Vallano ML. (2005) Roscovitine triggers excitotoxicity in cultured granule neurons by enhancing glutamate release. Mol Pharmacol. 68: 1331-1342.
Monaco EA 3rd. (2004) Recent evidence regarding a role for Cdk5 dysregulation in Alzheimer's disease. Curr Alzheimer Res. 1: 33-38.
Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogenic differentiation. Development. 111: 741-748.
Morefield SI, et al. (2000) Drug evaluations using neuronal networks cultured on microelectrode arrays. Biosens Bioelectron. 15: 383-396.
Morganroth J and Gussak I. (2004) Cardiac Safety of Noncardiac Drugs: Practical Guidelines for Clinical Research and Drug Development. New York, Humana Press.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-1 mediates the inhibition of endothelial cell proliferation and the promotion of skeletal myoblast differentiation by Sparc: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different In Vitro Systems Affect CYPIA1 Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate $CO_2/H+$-sensitive neurons in rat brain stem slices. J Appl Physiol. 95: 910-921.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Müller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481: 617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan to Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash MP, et al (2006) Evidence for multiple mechanisms in human ventricular fibrillation. Circulation. 114: 536-542.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol in Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32: 4267-4274.
Natarajan A, et al. (2013) Engineered In Vitro Feed-Forward Networks. J Biotechnol Biomater. 3: 153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) Of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24: 1517-1530.
Nelson PG. (1975) Nerve and muscle cells in culture. Physiol Rev. 55: 1-61.

(56) References Cited

OTHER PUBLICATIONS

Nerbonne JM and Kass RS. (2005) Molecular physiology of cardiac repolarization. Physiol Rev. 85: 1205-1253.

Nguemo F, et al. (2012) In vitro model for assessing arrhythmogenic properties of drugs based on high-resolution impedance measurements. Cell Physiol Biochem. 29: 819-832.

Nguyen L, et al. (2006) The Yin and Yang of cell cycle progression and differentiation in the oligodendroglial lineage. Ment Retard Dev Disabil Res Rev. 12: 85-96.

Nicolelis MAL and Ribeiro S. (2002) Multielectrode recordings: the next steps. Curr Opin Neurobiol. 12: 602-606.

Nimmrich V, et al. (2008) Amyloid beta oligomers (A beta(1-42) globulomer) suppress spontaneous synaptic activity by inhibition of P/Q-type calcium currents. J Neurosci. 28: 788-797.

Nishikawa J, et al. (2005) Increase of Cardiotrophin-1 immunoreactivity in regenerating and overloaded but not denervated muscles of rats. Neuropathology. 25: 54-65.

Nishimaru H, et al. (2005) Mammalian motor neurons corelease glutamate and acetylcholine at central synapses. Proc Natl Acad Sci U S A. 102: 5245-5249.

Nistor GI, et al. (2005) Human embryonic stem cells differentiate into oligodendrocytes in high purity and myelinate after spinal cord transplantation. Glia. 49: 385-396.

Noble D. (2004) Modeling the heart. Physiology (Bethesda). 19: 191-197.

Noll E and Miller RH. (1993) Oligodendrocyte precursors originate at the ventral ventricular zone dorsal to the ventral midline region in the embryonic rat spinal cord. Development. 118: 563-573.

Normann RA, et al. (1999) A neural interface for a cortical vision prosthesis. Vision Res. 39: 2577-2587.

Norris W, et al. (2000) Slow muscle induction by Hedgehog signalling in vitro. J Cell Sci. 113: 2695-2703.

Nyitrai G, et al. (2006) Extracellular level of GABA and Glu: in vivo microdialysis-HPLC measurements. Curr Top Med Chem. 6: 935-940.

Oakley RA, et al. (1997) Neurotrophin-3 promotes the differentiation of muscle spindle afferents in the absence of peripheral targets. J Neurosci. 17: 4262-4274.

O'Connor SM, et al. (2000) Immobilization of neural cells in three-dimensional matrices for biosensor applications. Biosens Bioelectron. 14: 871-881.

Offenhausser A and Knoll W. (2001) Cell-transistor hybrid systems and their potential applications. Trends Biotechnol. 19: 62-66.

Offenhausser A, et al. (1997) Field-effect transistor array for monitoring electrical activity from mammalian neurons in culture. Biosensors and Bioelectronics. 12: 819-826.

Oh TI, et al. (2007) Real-time multiple fluorescence detection of microscale cell culture analog devices in situ. Cytometry A. 71: 857-865.

Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.

Olson E. (1992a) Activation of muscle-specific transcription by myogenic helix-loop-helix proteins. Symp Soc Exp Biol. 46: 331-341.

Olson EN and Perry WM. (1992b) MyoD and the paradoxes of myogenesis. Curr Biol. 2: 35-37.

Olson EN and Williams RS. (2000) Calcineurin Signaling and Muscle Remodeling. Cell. 101: 689-692.

Olson EN. (1992c) Interplay between proliferation and differentiation within the myogenic lineage. Dev Biol. 154: 261-272.

Olwin BB and Rapraeger A. (1992) Repression of myogenic differentiation by aFGF, bFGF, and K-FGF is dependent on cellular heparan sulfate. J Cell Biol. 118: 631-639.

Oppenheim RW, et al. (1991) Control of embryonic motoneuron survival in vivo by ciliary neurotrophic factor. Science. 251: 1616-1618.

Oppenheim RW, et al. (2001) Cardiotrophin-1, a muscle-derived cytokine, is required for the survival of subpopulations of developing motoneurons. J Neurosci. 21: 1283-1291.

Orentas DM and Miller RH. (1998) Regulation of oligodendrocyte development. Mol Neurobiol. 18: 247-259.

Orlov SN and Hamet P. (2006) Intracellular monovalent ions as second messengers. J Membr Biol. 210: 161-172.

Ostuni E, et al. (2000) Patterning mammalian cells using elastomeric membranes. Langmuir. 16: 7811-7819.

Oumata N, et al. (2008) Roscovitine-derived, dual-specificity inhibitors of cyclin-dependent kinases and casein kinases 1. J Med Chem. 51: 5229-5242.

Padmanabhan J, et al. (1999) Role of cell cycle regulatory proteins in cerebellar granule neuron apoptosis. J Neurosci. 19: 8747-8756.

Pagan SM, et al. (1996) Surgical removal of limb bud Sonic hedgehog results in posterior skeletal defects. Dev Biol. 180: 35-40.

Pancrazio JJ, et al. (1998) Portable cell-based biosensor system for toxin detection. Sensors and Actuators B Chem. 53: 179-185.

Park J, et al. (2005) Real-time measurement of the contractile forces of self-organized cardiomyocytes on hybrid biopolymer microcantilevers. Anal Chem. 77: 6571-6580.

Parker KK, et al. (2008) Myofibrillar architecture in engineered cardiac myocytes. Circ Res. 103: 340-342.

Parng C, et al. (2002) Zebrafish: A Preclinical Model for Drug Screening. Assay Drug Dev Technol. 1: 41-48.

Parviz M and Gross GW. (2007) Quantification of zinc toxicity using neuronal networks on microelectrode arrays. Neurotoxicology. 28: 520-531.

Paspalas CD and Papadopoulos GC. (1996) Ultrastructural relationships between noradrenergic nerve fibers and non-neuronal elements in the rat cerebral cortex. Glia. 17: 133-146.

Payne ET, et al. (2006) Nutritional therapy improves function and complements corticosteroid intervention in mdx mice. Muscle Nerve. 33: 66-77.

Peng HB, et al. (2003) Differential effects of neurotrophins and schwann cell-derived signals on neuronal survival/growth and synaptogenesis. J Neurosci. 23: 5050-5060.

Peroulakis ME and Forger NG. (2000) Ciliary neurotrophic factor increases muscle fiber number in the developing levator ani muscle of female rats. Neurosci Lett. 296: 73-76.

Perrier AL, et al. (2004) Derivation of midbrain dopamine neurons from human embryonic stem cells. Proc Natl Acad Sci U S A. 101: 12543-12548.

Peters A. (1964) Observations on the Connexions Between Myelin Sheaths and Glial Cells in the Optic Nerves of Young Rats. J Anat. 98: 125-134.

Peterson CA, et al. (1999) Effects of moisture on Fowler—Nordheim characterization of thin silicon-oxide films. J Vac Science Technol A. 17: 2753-2758.

Pette D and Staron S. (2001) Transitions of muscle fiber phenotypic profiles. Histochem Cell Biol. 115: 359-372.

Pette D, et al. (2002) Partial fast-to-slow conversion of regenerating rat fast-twitche muscle by chronic low frequency stimulation. J Muscle Res Cell Motil. 3: 215-221.

Pfeiffer SE, et al. (1993) The oligodendrocyte and its many cellular processes. Trends Cell Biol. 3: 191-197.

Pfrieger FW and Banes BA. (1997) Synaptic efficacy enhanced by glial cells in vitro. Science. 277: 1684-1687.

Pijnappels DA, et al. (2007) Resynchronization of separated rat cardiomyocyte fields with genetically modified human ventricular scar fibroblasts. Circulation. 116: 2018-2028.

Pillekamp F, et al. (2012) Contractile properties of early human embryonic stem cell-derived cardiomyocytes: beta-adrenergic stimulation induces positive chronotropy and lusitropy but not inotropy. Stem Cells Dev. 21: 2111-2121.

Podratz J, et al. (2004) Antioxidants are necessary for myelination of dorsal root ganglion neurons, in vitro. Glia. 45: 54-58.

Pomp O, et al. (2005) Generation of peripheral sensory and sympathetic neurons and neural crest cells from human embrionic stem cells. Stem Cells. 23: 923-930.

Pomp O, et al. (2008) PA6-induced human embryonic stem cell-derived neurospheres: a new source of human peripheral sensory neurons and neural crest cells. Brain Res. 1230: 50-60.

(56) References Cited

OTHER PUBLICATIONS

Pontier C, et al. (2001) HT29-MTX and Caco-2/TC7 monolayers as predictive models for human intestinal absorption: role of the mucus layer. J Pharm Sci. 90: 1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and McMorris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B-Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly(ethylene glycol) Photolithography to Create High-Density Cell Arrays on Glass. Langmuir. 19: 9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.
Richert L, et al. (2004) pH dependent growth of poly(L-lysine)/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation in apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.
Rosenberg SS, et al. (2008) The geometric and spatial constraints of the microenvironment induce oligodendrocyte differentiation. Proc Natl Acad Sci U S A. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-1. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. (1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. J Neurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-641.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-119.
Scherer J, et al. (1995) Differentiation and maturation of rabbit retinal oligodendrocyte precursor cells in vitro. Brain Res Dev Brain Res. 89: 214-226.
Schiaffino S and Serrano A. (2002) Calcineurin signaling and neural control of skeletal muscle fiber type and size. Trends Pharmacol Sci. 23: 569-575.

(56) References Cited

OTHER PUBLICATIONS

Schiaffino S, et al. (2007) Activity-Dependent Signaling Pathways Controlling Muscle Diversity and Plasticity. Physiology. 22: 269-278.
Schluter H, et al. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276: C900-C906.
Scholzen T, et al. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.
Schuster R, et al. (1995) Use of mathematical models for predicting the metabolic effect of large-scale enzyme activity alterations. Application to enzyme deficiencies of red blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote M, et al. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KATP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12: 1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.
Sheridan DC, et al. (2003) Ca2+-dependent excitation-contraction coupling triggered by the heterologous cardiac/brain DHPR beta2a-subunit in skeletal myotubes. Biophys J. 85: 3739-3757.
Sheridan DC, et al. (2003) Truncation of the carboxyl terminus of the dihydropyridine receptor beta1a subunit promotes Ca2+ dependent excitation-contraction coupling in skeletal myotubes. Biophys J. 84: 220-237.
Sherman DL and Brophy PJ. (2005) Mechanisms of axon ensheathment and myelin growth. Nat Rev Neurosci. 6: 683-690.
Sherman DL, et al. (2005) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14: 1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19: 317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J, et al. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313: 107-117.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-1729.
Soundararajan P, et al. (2007) Easy and rapid differentiation of embryonic stem cells into functional motoneurons using sonic hedgehog-producing cells. Stem Cells. 25: 1697-1706.
Spach MS, et al. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.

(56) References Cited

OTHER PUBLICATIONS

Spargo BJ, et al. (1994) Spatially controlled adhesion, spreading, and differentiation of endothelial cells on self-assembled molecular monolayers. Proc Natl Acad Sci USA. 91: 11070-11074.

Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.

St John PM, et al. (1997) Preferential glial cell attachment to microcontact printed surfaces. J Neurosci Methods. 75: 171-177.

St. George-Hyslop PH, et al. (2005) Molecular biology and genetics of Alzheimer's disease. C R Biol. 328: 119-130.

Stavarachi M, et al. (2010) Spinal muscular atrophy disease: a literature review for therapeutic strategies. J Med Life. 3: 3-9.

Steffen LS, et al. (2007) Zebrafish orthologs of human muscular dystrophy genes. BMC Genomics. 8: 79.

Stenger DA, et al. (1992) Coplanar Molecular Assemblies of Aminoalkylsilane and Perfluorinated Alkylsilane—Characterization and Geometric Definition of Mammalian-Cell Adhesion and Growth. Journal of the American Chemical Society. 114: 8435-8442.

Stenger DA, et al. (1993) Surface determinants of neuronal survival and growth on self-assembled monolayers in culture. Brain Res. 630: 136-147.

Stenger DA, et al. (1998) Microlithographic determination of axonal/dendritic polarity in cultured hippocampal neurons. J Neurosci Methods. 82: 167-173.

Sternberger NH, et al. (1985) Immunocytochemistry of myelin basic proteins in adult rat oligodendroglia. J Neuroimmunol. 7: 355-363.

Stett A, et al (2003) Biological application of microelectrode arrays in drug discovery and basic research. Anal Bioanal Chem. 377: 486-495.

Stevens JL. (2006) Future of toxicology—mechanisms of toxicity and drug safety: where do we go from here? Chem Res Toxicol. 19: 1393-1401.

Stinstra J, et al. (2006) A Model of 3D Propagation in Discrete Cardiac Tissue. Comput Cardiol. 33: 41-44.

Stockwell BR. (2004) Exploring biology with small organic molecules. Nature. 432: 846-854.

Stoney GG. (1909) The Tension of Metallic Films Deposited by Electrolysis. Proc Roy Soc London. 82: 172-175.

Subramanian B, et al. (2010) Tissue-engineered three-dimensional in vitro models for normal and diseased kidney. Tissue Eng Part A. 16: 2821-2831.

Sun L, et al. (2007) JAK1-STAT1-STAT3, a key pathway promoting proliferation and preventing premature differentiation of myoblasts. J Cell Biol. 179: 129-138.

Sung JH, et al. (2009a) A micro cell culture analog (microCCA) with 3-D hydrogel culture of multiple cell lines to assess metabolism-dependent cytotoxicity of anti-cancer drugs. Lab Chip. 9: 1385-1394.

Sung JH, et al. (2009b) Prevention of air bubble formation in a microfluidic perfusion cell culture system using a microscale bubble trap. Biomed Microdevices. 11: 731-738.

Sung JH, et al. (2009c) Fluorescence optical detection in situ for real-time monitoring of cytochrome P450 enzymatic activity of liver cells in multiple microfluidic devices. Biotechnol Bioeng. 104: 516-525.

Sung JH, et al. (2010) A microfluidic device for a pharmacokinetic-pharmacodynamic (PK-PD) model on a chip. Lab Chip. 10: 446-455.

Sung JH, et al. (2013) Microfabricated mammalian organ systems and their integration into models of whole animals and humans. Lab Chip. 13: 1201-1212.

Suter W. (2006) Predictive value of in vitro safety studies. Curr Opin Chem Biol. 10: 362-366.

Sutton NM, et al. (2007) Clinical effects and outcome of feline permethrin spot-on poisonings reported to the Veterinary Poisons Information Service (VPIS), London. J Feline Med Surg. 9: 335-339.

Swasdison S, et al. (1992) Formation of highly organized skeletal muscle fibers in vitro. Comparison with muscle development in vivo. J Cell Sci. 102: 643-652.

Swynghedauw B. (1999) Molecular mechanisms of myocardial remodeling. Physiol Rev. 79: 215-262.

Takagishi Y, et al. (2000) Species-specific difference in distribution of voltage-gated L-type Ca(2+) channels of cardiac myocytes. Am J Physiol Cell Physiol. 279: C1963-C1969.

Takahashi T. (1978) Intracellular recording from visually identified motoneurons in rat spinal cord slices. Proc R Soc Lond B Biol Sci. 202: 417-421.

Takashima Y, et al. (2007) Neuroepithelial cells supply an initial transient wave of MSC differentiation. Cell. 129: 1377-1388.

Tan W, et al. (2003) Microfluidic patterning of cells in extracellular matrix biopolymers: effects of channel size, cell type, and matrix composition on pattern integrity. Tissue Eng. 9: 255-267.

Tanaka M, et al. (2005) An Unbiased Cell Morphology Based Screen for New, Biologically Active Small Molecules. PLoS Biol. 3: e128.

Tanaka Y, et al. (2006) An actuated pump on-chip powered by cultured cardiomyocytes. Lab Chip. 6: 362-368.

Tarasenko YI, et al. (2007) Human fetal neural stem cells grafted into contusion-injured rat spinal cords improve behavior. J Neurosci Res. 85: 47-57.

Tatosian D, et al. (2009) A novel system for evaluation of drug mixtures for potential efficacy in treating multidrug resistant cancers. Biotechnol Bioeng. 103: 187-198.

Termin A, et al. (1992) Changes in myosin heavy-chain isoform synthesis of chronically stimulated rat fast-twitch muscle. Eur J Biochem. 204: 569-573.

Terstappen GC, et al. (2007) Target deconvolution strategies in drug discovery. Nat. Rev Drug Discov. 6: 891-903.

Thomas CA, et al. (1972) A miniature microelectrode array to monitor the bioelectric activity of cultured cells. Exp Cell Res. 74: 61-66.

Thomas R. (1973) Boolean formalization of genetic control circuits. J Theor Biol. 1973. 42: 563-585.

Thompson PD, et al. (2006) An assessment of statin safety by muscle experts. Am J Cardiol. 97: 69C-76C.

Thompson RB, et al. (2005) Intracardiac transplantation of a mixed population of bone marrow cells improves both regional systolic contractility and diastolic relaxation. J Heart Lung Transplant. 24: 205-214.

Thorrez L, et al. (2008) Growth, differentiation, transplantation and survival of human skeletal myofibers on biodegradable scaffolds. Biomaterials. 29: 75-84.

Timmerman W, et al. (1997) Brain microdialysis of GABA and glutamate: what does it signify? Synapse. 27: 242-261.

Tobert JA. (2003) Lovastatin and beyond: the history of the HMGCoA reductase inhibitors. Nat Rev Drug Discov. 2: 517-526.

Toga T, et al. (2007) The 5-HT(4) agonists cisapride, mosapride, and CJ-033466, a Novel potent compound, exhibit different human ether-a-go-go-related gene (hERG)-blocking activities. J Pharmacol Sci. 105: 207-210.

Tomb JF, et al. (1997) The complete genome sequence of the gastric pathogen Helicobacter pylori. Nature. 388: 539-547.

Torgan CE and Daniels MP. (2001) Regulation of myosin heavy chain expression during rat skeletal muscle development in vitro. Mol Biol Cell. 12: 1499-1508.

Torgan CE and Daniels MP. (2006) Calcineurin localization in skeletal muscle offers insights into potential new targets. J Histochem Cytochem. 54: 119-128.

Torimitsu K, et al. (1990) Selective growth of sensory nerve fibers on metal oxide pattern in culture. Brain Res Dev Brain Res. 51: 128-131.

Townsend KP, et al. (2005) Novel therapeutic opportunities for Alzheimer's disease: focus on nonsteroidal anti-inflammatory drugs. FASEB J. 19: 1592-1601.

(56) References Cited

OTHER PUBLICATIONS

Tung L, et al. (2007) Imaging fibrillation/defibrillation in a dish. J Electrocardiol. 40: S62-S65.
Tung L, et al. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.
Urakami H, et al. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through NO-synthase. Physiol Res. 44: 205-208.
Vakakis N, et al. (1995) In vitro myoblast to myotube transformations in the presence of leukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
van de Ven C, et al. (2007) The potential of umbilical cord blood multipotent stem cells for nonhematopoietic tissue and cell regeneration. Exp Hematol. 35: 1753-1765.
van der Valk J, et al. (2010) Optimization of chemically defined cell culture media—replacing fetal bovine serum in mammalian in vitro methods. Toxicol In Vitro. 24: 1053-1063.
van Rijen HV, et al. (2006) Connexins and cardiac arrhythmias. Adv Cardiol. 42: 150-160.
van Soest PF, et al. (1998) Conopressin affects excitability, firing, and action potential shape through stimulation of transient and persistent inward currents in mullusc an neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue culture: Effects on skeletal muscle organogenesis. In Vitro Cell Dev Biol. 24: 609-619.
Varghese K, et al. (2009) Regeneration and characterization of adult mouse hippocampal neurons in a defined in vitro system. J Neurosci Methods. 177: 51-59.
Varghese K, et al. (2010) A new target for amyloid beta toxicity validated by standard and high-throughput electrophysiology. PLoS One. 5: e8643.
Vargo TG, et al. (1992) Monolayer Chemical Lithography and Characterization of Fluoropolymer Films. Langmuir. 8: 130-134.
Vartanian T, et al. (1988) Oligodendrocyte substratum adhesion modulates expression of adenylate cyclase-linked receptors. Proc Natl Acad Sci U S A. 85: 939-943.
Ventimiglia R, et a. (1987) Localization of beta-adrenergic receptors on differentiated cells of the central nervous system in culture. Proc Natl Acad Sci U S A. 84: 5073-5077.

Vidarsson H, et al. (2010) Differentiation of human embryonic stem cells to cardiomyocytes for in vitro and in vivo applications. Stem Cell Rev. 6: 108-120.
Viravaidya K, et al. (2004) Incorporation of 3T3-L1 cells to mimic bioaccumulation in a microscale cell culture analog device for toxicity studies. Biotechnol Prog. 20: 590-597.
Vogel V, et al. (2006) Local force and geometry sensing regulate cell functions. Nat Rev Mol Cell Biol. 7: 265-275.
Vogel Z, et al. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.
Waggoner PS, et al. (2007) Micro- and nanomechanical sensors for environmental, chemical, and biological detection. Lab Chip. 7: 1238-1255.
Wagner I, et al. (2013) A dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM, et al. (1999) Why adult mammalian intrafusal and extrafusal fibers contain different myosin heavy-chain isoforms. Trends Neurosci. 22: 180-184.
Walsh DM, et al. (2007) A beta oligomers—a decade of discovery. J Neurochem. 101: 1172-1184.
Walsh K, et al. (2005) Human central nervous system tissue culture: a historical review and examination of recent advances. Neurobiol Dis. 18: 2-18.
Wang HW, et al. (2002) Soluble oligomers of beta amyloid (1-42) inhibit long-term potentiation but not long-term depression in rat dentate gyms. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and ciliary neurotrophic factor on the proliferation and differentiation of adult human myoblasts. Cell Mol Neurobiol. 28: 113-124.
Ward JH, et al. (2001) Micropatterning of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122: R43-R50.
Winslow RL, et al. (2005) Using models of the myocyte for functional interpretation of cardiac proteomic data. J Physiol. 563: 73-81.

(56) References Cited

OTHER PUBLICATIONS

Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation of myelination by Schwann cells. Ann N Y Acad Sci. 605: 1-14.
Wright CD, et al. (2008) Nuclear alphal-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity in functional mammalian neuronal networks grown on patterned surfaces. J Neurosci Methods. 117: 123-131.
Xi J, et al. (2005) Self-assembled microdevices driven by muscle. Nat Mater. 4: 180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-1 transgenic rats. Transplantation. 82: 865-875.
Xu T, et al. (2004) Construction of high-density bacterial colony arrays and patterns by the ink jet method. Biotechnol Bioeng. 85: 29-33.
Xu T, et al. (2005) Inkjet printing of viable mammalian cells. Biomaterials. 26: 93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.
Yan J, et al. (2007) Extensive neuronal differentiation of human neural stem cell grafts in adult rat spinal cord. PLoS Med. 4: 318-332.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly(diol citrate) biodegradable elastomers. Biomaterials. 27: 1889-1898.
Yang L, et al. (2007) Increased asynchronous release and aberrant calcium channel activation in amyloid precursor protein deficient neuromuscular synapses. Neuroscience. 149: 768-778.
Yang LX, et al. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatterning capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.
Yap FL, et al. (2007) Protein and cell micropatterning and its integration with micro/nanoparticles assembly. Biosens Bioelectron. 22: 775-788.
Yasuda SI, et al. (2001) A novel method to study contraction characteristics of a single cardiac myocyte using carbon fibers. Am J Physiol Heart Circ Physiol. 281: H1442-H1446.
Yeung CK, et al. (2007) Drug profiling using planar microelectrode arrays. Anal Bioanal Chem. 387: 2673-2680.
Yin SH, et al. (2005) Measuring single cardiac myocyte contractile force via moving a magnetic bead. Biophys J. 88: 1489-1495.
Zhao BL, et al. (1989) Scavenging effect of extracts of green tea and natural antioxidants on active oxygen radicals. Cell Biophys. 14: 175-185.
Zhou L, et al. (2005) Mechanistic model of cardiac energy metabolism predicts localization of glycolysis to cytosolic subdomain during ischemia. Am J Physiol Heart Circ Physiol. 288: H2400-H2411.
Zhou Z, et al. (1999) Block of HERG potassium channels by the antihistamine astemizole and its metabolites desmethylastemizole and norastemizole. J Cardiovasc Electrophysiol. 10: 836-843.
Zimmermann WH, et al. (2000) Three-dimensional engineered heart tissue from neonatal rat cardiac myocytes. Biotechnol Bioeng. 68: 106-114.
Zimmermann WH, et al. (2002) Tissue Engineering of a Differentiated Cardiac Muscle Construct. Circ Res. 90: 223-230.
Zorzano A, et al. (2003) Intracellular signals involved in the effects of insulin-like growth factors and neuregulins on myofibre formation. Cell Signal. 15: 141-149.
Zurn AD, et al. (1996) Combined effects of GDNF, BDNF, and CNTF on motoneuron differentiation in vitro. J Neurosci Res. 44: 133-141.
Zweigerdt R, et al. (2003) Generation of confluent cardiomyocyte monolayers derived from embryonic stem cells in suspension: a cell source for new therapies and screening strategies. Cytotherapy. 5: 399-413.

MODEL AND METHODS FOR IDENTIFYING POINTS OF ACTION IN ELECTRICALLY ACTIVE CELLS

CROSS-REFERENCE TO RELATED PATENT APPLICATIONS

This application is a National Phase Application of International Application No. PCT/US2011/023921, filed Feb. 7, 2011, which claims priority to U.S. Patent Application No. 61/301,669, filed Feb. 5, 2010, which applications are incorporated herein fully by this reference.

STATEMENT OF GOVERNMENT INTEREST

This invention was made with Government support under agency contract/grant number R01 EB005459 awarded by the National Institutes of Health. The government has certain rights in this invention.

FIELD OF THE INVENTION

The present invention relates to the field of cell modeling, and, more particularly, to a model and methods for identifying a point of action of a substance in an electrically active cell.

BACKGROUND OF THE INVENTION

A primary challenge common to both, toxicology and drug development, is the accurate in vitro determination of targets for a toxin or drug. Numerous methods have been developed to quantify the physiological change induced by toxins/drugs in whole cell sensing devices [1, 2]. One of the techniques frequently used for monitoring the state and activity of excitable cells is the recording of action potentials (APs) [3, 4]. The shape of a given AP contains a significant amount of information, as it is dependent on the concerted action of ion channels located in cellular membranes. Ion currents through ion channels are tightly regulated by receptors and the intracellular messenger systems [5, 6], calcium [7], sodium [8], and potassium [9]. Channel modulators as well as a multitude of toxins and pathological conditions [10, 11] are known to significantly affect the shape of APs. The myriad of complexities and challenges faced in the determination of sites of action for toxins and potential lead compounds are well known as well [12, 13]. However, whole-cell models capable of using the shape of APs in order to accurately determine points of action for a particular toxin are currently lacking. Therefore, there is a clear need for a whole-cell modeling framework that functionally links AP generation via ion channels with all other cellular processes (metabolism, signaling, transcription, translation, etc.).

SUMMARY OF THE INVENTION

The present invention discloses a model for generating predicted action potentials of an electrically active cell, for example, a mammalian neuronal cell. The model comprises a first submodel containing Hodgkin-Huxley elements generating action potentials based on electrical equivalent circuits. A second submodel is based on reaction kinetics of mammalian cell metabolism and is operatively coupled with the first submodel. A third submodel is based on Boolean dynamics representing signaling and associated cellular processes and is operatively coupled with the first and second submodels.

In an embodiment of the invention, the model as described above is capable of reacting to stimuli which are internal or external to the cell. Those skilled in the art will recognize that the stimulus may include any compound or composition that triggers the cell to generate an electrical response. Accordingly, an electrical stimulus is included in the term "stimulus." Additionally, exposure to electromagnetic radiation, for example, light waves, would also induce the cell to generate an electrical response in some cases. All of these are included in the term "stimulus." Preferably, the first, second and third submodels are computer implemented. The first submodel quantifies changes in intracellular processes based on physiological changes in the cell responsive to input received from the second and third submodels. The second submodel comprises a plurality of modeled physiological compartments, each having an associated compartment volume. The modeled physiological compartments comprise whole cell volume, mitochondrial volume, endoplasmic reticulum volume, nuclear volume and extracellular volume. Preferably, the mitochondrial volume, endoplasmic reticulum volume and nuclear volume are nested in the whole cell volume. Also preferably, the third submodel further comprises network topology and dynamic state for each pathway node to thereby assign relative importance to a pathway node with respect to overall response of a biological network. More specifically, the third submodel may further comprise Glass dynamics providing a continuous time course simulation.

Additionally, the disclosed model may be used to generate a library of simulation results comprising model parameters of the mammalian neuronal cell. The library of simulation results provides for the parameters to be stored in a structured query language database programmed in a computer. The results stored comprise a plurality of parameters selected from simulated action potentials, Boolean model data of simulated cell signaling cascades, scaling factors of cell metabolic processes, ion and ATP concentrations, data for ion channels included in the Hodgkin-Huxley calculations, and combinations thereof.

The model disclosed may be used to predict mammalian neuronal cell response to an applied stimulus. In particular, the disclosed model provides a method of identifying a point of action of a stimulus applied to a mammalian neuronal cell. It should be understood that the stimulus may be external, for example, as when a compound or composition is applied to a cell, e.g. an antibiotic, a toxin, an unknown compound. The stimulus could also be internal, for example, when a gene is activated. The method of this embodiment of the invention comprises storing a library of calculated action potentials and associated cellular parameters generated by a model having a first submodel based on Hodgkin-Huxley calculations, a second submodel operably linked thereto and based on reaction kinetics of neuronal cell metabolism and a third submodel operably linked to the first and second submodels and based on Boolean dynamics representing signaling and associated cellular processes. The method continues by applying the stimulus to the mammalian neuronal cell in vitro so that the cell generates an action potential; and then comparing the cell-generated action potential with the calculated action potentials stored in the library, wherein a match is predictive of the cellular point of action of the applied stimulus according to the parameters stored for the matching calculated action potential. In the method, the stimulus may comprise a drug or a toxin.

BRIEF DESCRIPTION OF THE DRAWINGS

FIG. 8A: Phase-contrast image of NG108-15 cell with a patch-clamp electrode attached (Scale bar=25 □m). FIG. 8B: Sodium currents recorded at different membrane potentials in voltage-clamp mode (solid line) and the results of the parameter fitting using the Hodgkin-Huxley model and the linear thermodynamic formalism (dotted line). FIG. 8C: Potassium currents (solid line) and the fitted curves using the model (dotted line). FIG. 8D, E, F, G: Effect of toxins on the action potentials of NG108-15 cells. The solid line is data recorded in current clamp experiments. The dotted line is the results of the simulation using the mathematical model of the NG108-15 cells after parameter fitting. Ion channel parameters were estimated based on action potential shapes.

(FIG. 12B) NADH/NAD ratio (red) and ATP/ADP ratio (blue) in the cytosol (circle) and mitochondria (square) in response to increased ATP consumption.

DETAILED DESCRIPTION OF THE PREFERRED EMBODIMENTS

In the Summary of the Invention above and in the Detailed Description of the Invention and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the present invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

Figure 1:
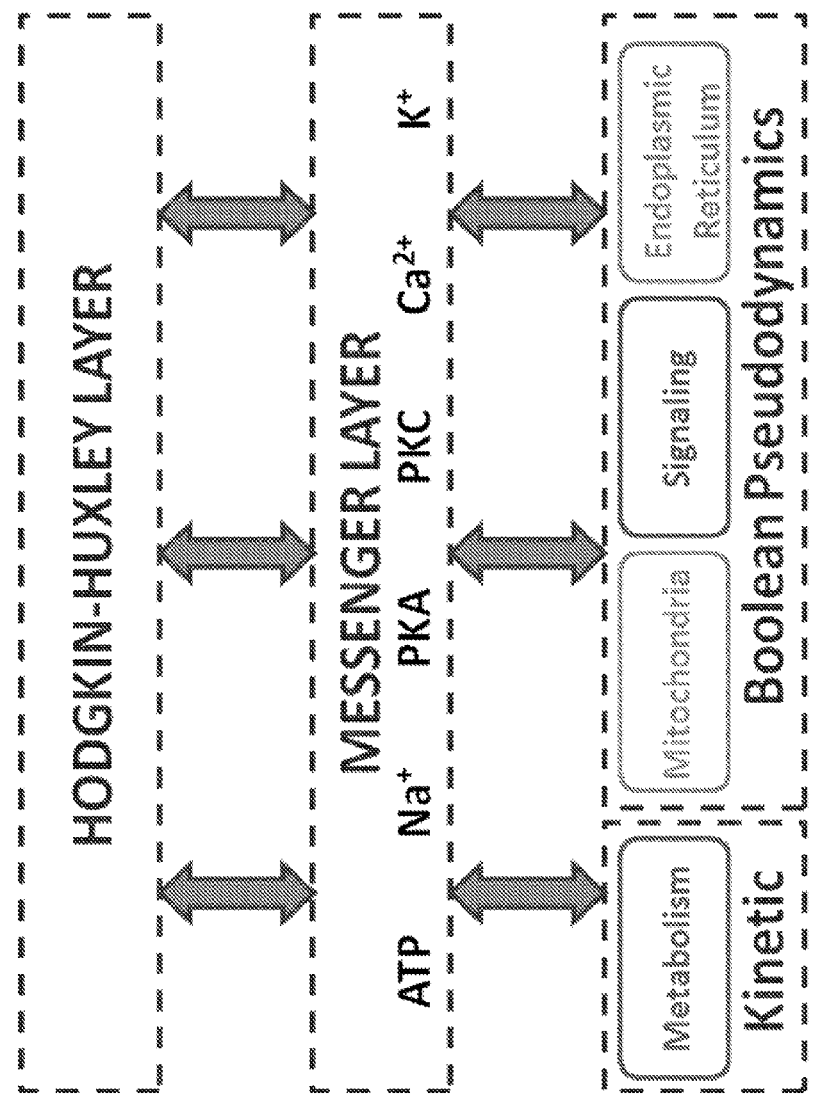
FIG. 1 is a diagram for the identification of toxin action using a whole cell modeling platform.

An aspect of an embodiment of the invention is to provide a model of an entire mammalian neuronal cell that is capable of reacting to both internal and external stimuli. The hybrid whole-cell model is the combination of three submodels that communicate via messengers (FIG. 1):

(1) A model for the generation of action potentials (APs) that is based on electrical equivalent circuits, containing Hodgkin-Huxley (HH) elements
(2) A detailed model to address mammalian cell metabolism that is based on reaction kinetics (3) A model for signaling and other cellular processes using Boolean dynamics How these three models connect and interact with each other to form the hybrid whole-cell model is unique to this invention. The final product of this invention is a database containing simulation results from the hybrid model in the form of AP shapes and their corresponding model parameters. The shape of APs recorded from neuronal cells, in the presence or absence of drugs, toxins or combinations thereof, can be compared automatically to simulated AP shapes stored in the database. The model parameters saved in the database along with AP shapes describe internal states of the cell under investigation. Parametric changes over time indicate a drug or toxins point(s) of action inside the cell. As the hybrid whole-cell model becomes more complex, the produced database will contain more detailed information about the possible internal or external stimuli and thus represent an invaluable tool for drug discovery, systems biology and functional genomics research.

Hodgkin-Huxley Based Model for Action Potentials

Ion channels are regulated by all common intracellular mechanisms including phosphorylation and second messenger dependent systems [15], with intracellular ions playing an equally significant role of second messengers in cells [16]. Electrical activity is highly dependent on the state/physiology/pathophysiology of the cells [17]. Action potential shape is determined by intracellular ionic concentrations, ATP, calcium, cAMP and other second messenger dependent channels and pumps [18-20].

In the presented hybrid whole-cell model, APs are generated by a Hodgkin-Huxley (HH) submodel. In 1952 the scientists Hodgkin and Huxley published an electrical equivalent circuit, composed of resistors and capacitances, in order to reproduce the shape of APs recorded from squid neurons. The original HH model did not couple intracellular processes to electrophysiological parameters and action potential generation was considered as an 'all-or-none' process, without significant variability. This view is in contrast with findings concerning participation of ion channels in intracellular signaling and metabolic pathways [15]. Realistic, experimentally validated cell models have already been developed and couple electrophysiological properties of the cell membrane to complex intracellular pathways [22, 23]. These models are routinely used to predict/explain physiological changes caused by intracellular mechanisms (gene expression changes, activation of second messenger systems, phosphorylation, etc.) [24]. In this invention we couple the HH-model to other models which are containing all relevant cellular processes (metabolism, signaling, etc.) in order to enable quantification of changes in intracellular processes based on physiological changes in the behavior of the cells.

The HH-model of this invention is implemented as a program in the scientific computation environment Matlab® (The Mathworks, Inc.), and calculates a time-dependent potential across the cell membrane by the following equation:

$$\frac{dV}{dt} = \frac{I_{external} - I_{ionic}}{C_M} \quad \text{(Eq. 1)}$$

with the potential V across the cell membrane, the time t, the sum of artificially induced currents $I_{external}$, the sum of membrane currents $I_{ionic}$ and the capacitance $C_M$ of the cell membrane. The HH-model is capable (but not limited) to compute voltage-gated sodium (Na), potassium (K) and calcium (Ca) as well as general leak (I) currents. A detailed description of the model and its calibration can be found in [21].

In addition to the published model, this invention links a part of the K-currents with the cytosolic concentration of adenosine triphosphate (ATP). ATP is known to be a ubiquitous source of energy in the cell and therefore important for interactions between the submodels. The formulations for individual ion currents composing an AP are summands of:

$$I_{ionic} = I_{Na} + I_K + I_{Ca} + I_l \quad \text{(Eq. 2)}$$
$$= g_{Na}m^3h(V - V_{Na}) + (g_K n^4 + g_{K_{ATP}} z)(V - V_K) +$$
$$g_{Ca} e^3 (V - V_{Ca}) + g_l (V - V_l)$$

with the maximal conductance for an ion species $g_{<ion>}$, the reverse potential $V_{<ion>}$ of an ion species as well as the state parameters m, h, n and e to describe a channel population's probability to be open or closed (details in [21]). The potassium currents are a combination of currents through two separate ion channels. Potassium currents are partially governed by $g_k n^4$ and thus purely voltage-gated, whereas $g_{K_{ATP}} z$ describes an additional influence due to the intracellular concentration of ATP. The factor z, scaling a significant portion of potassium currents, is calculated to $$\frac{1}{z} = \left(1 + \frac{[ATP]}{k_z}\right)^\gamma \quad \text{(Eq. 3)}$$

with $k_z$=0.06 and $\gamma$=1.3. When the HH-model is executed, the intracellular ion and ATP concentrations are determined by the other models (Boolean & Metabolic).

Modeling of Reaction Kinetics for Simulations of Cell Metabolism

Figure 2:
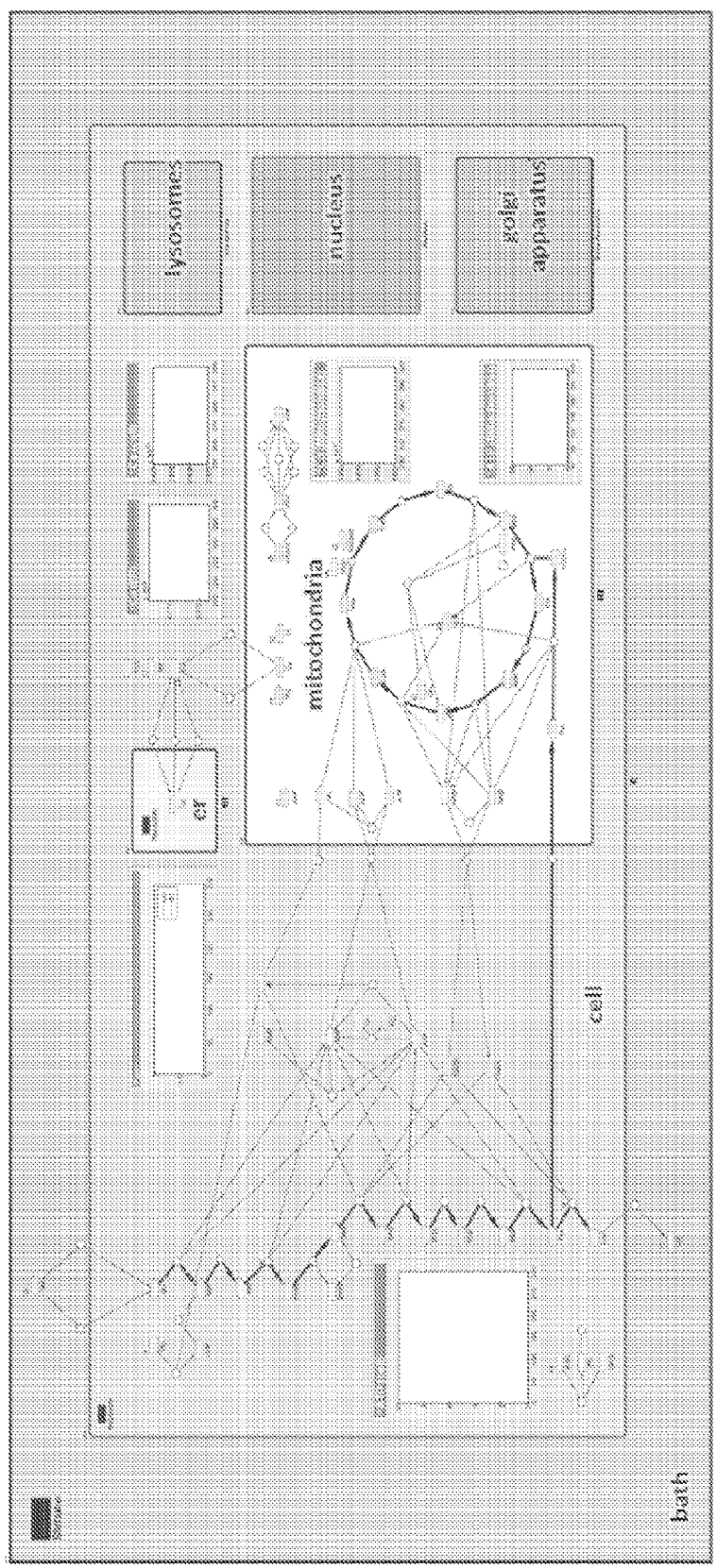
FIG. 2 is a screenshot of a metabolic model in Matlab®'s SimBiology® including compartments for mitochondria, endoplasmatic reticulum, lysosomes, golgi apparatus and the nucleus.

The model of an NG108-15 was implemented in the commercially available tool box SimBiology® for the scientific programming environment Matlab® (both from The Mathworks, Inc.). However, in order to capture the experimental environment, the models were implemented with physiological compartments, including physiological compartment volumes. The cellular volume of the NG108-15 hybrid cell was calculated to be ~4.7712938E-8 ml using the equation for the volume of a sphere. The radius used, 22.5 µm, is within the experimentally observed range published by the American Type Culture Collection (ATCC). The mitochondrial volume was calculated to be ~1.0471975E-12 ml using the equation for the volume of an ellipsoid, with a length of 2 µm, width of 1 µm and depth of 1 µm. The mitochondrial volume was multiplied by 400, an estimated number of mitochondria in an NG108-15 hybrid cell, and implemented as total mitochondrial volume. The volumes of the endoplasmic reticulum and the nucleus were approximated at 10% of the cellular volume, or ~4.7712938E-9 ml. Presuming a total simulation volume of 1 ml, the extracellular volume was calculated to be ~0.9940835 ml. The compartments were implemented in SimBiology® as nested (FIG. 2), whereby the nuclear, endoplasmic reticulum and mitochondrial volumes were nested in the cellular volume and the cellular volume was nested in the extracellular volume. In addition, the compartments were implemented as volumetric ratios, in order to address issues regarding solver tolerances (solver: Solaris). Hence, the volumetric ratios were calculated to be 2.0834675E7 (extracellular), 1.0 (cellular), 8.779149E-3 (mitochondrial), 0.1 (endoplasmic reticulum) and 0.1 (nuclear).

The compartmentalized metabolic model of an NG108-15 response to ATP load couples the metabolic models originally proposed by Lambeth (glycolysis) [33] and Cortassa (mitochondria) [34]. The glycolysis model (FIG. 3) converts glycogen to lactate through a series of fourteen reactions involving 21 species. The model contains fully reversible kinetic equations for each enzymatic reaction, along with phosphate buffering via creatine kinase. The pyruvate generated by the glycolytic pathway is then either converted to lactate by means of lactate dehydrogenase or to acetyl coenzyme A (AcCoA), for use in the TCA cycle, by means of pyruvate dehydrogenase. The detailed mitochondrial model (FIG. 4) consisting of 27 chemical species and 22 reactions, including the tricarboxylic acid (TCA) cycle, oxidative phosphorylation and mitochondrial transport processes, was also constructed [34]. The TCA cycle completes the oxidation of AcCoA to $CO_2$ producing NADH and $FADH_2$, which provides the driving force for oxidative phosphorylation. When AcCoA concentrations are low, the TCA cycle is driven primarily by consumption of glutamate, while high, the carbon flux through the TCA cycle can be regulated by the production of glutamate. TCA cycle dehydrogenases are regulated by mitochondrial $Ca^{2+}$ concentration, and in this way, the rate of $Ca^{2+}$ uptake by mitochondria is involved in membrane polarization through the TCA cycle and oxidative phosphorylation. The model includes both the explicit electrical gradient ($\Delta\psi_m$) and proton gradient ($\Delta$pH) across the mitochondrial inner membrane established by oxidative phosphorylation. The large $\Delta\psi_m$ of the mitochondrial inner membrane determines the electrochemical transport of ions, including calcium influx and efflux. In addition, the model considers the explicit dependence of the citric acid cycle dehydrogenases on mitochondrial calcium concentration. Calcium dynamics are an important part of this model, as the action of many toxins includes prolonged increase in cytoplasmic $Ca^{2+}$ concentration [35].

In order to allow changes in simulated activity of the glycolysis model [33] to the mitochondrial metabolism model [34], every reaction was supplemented by a scaling factor $S_{Gly}$ and $S_{Mit}$, respectively. The glycolysis model was coupled to the mitochondrial metabolism model with additional reactions for pyruvate transport into the mitochondria and conversion to acetyl CoA by pyruvate dehydrogenase. The rate equation for pyruvate transport had the general form $$v = V_{max} \times r(X) \times \left( \prod_i x_i^{c_{ij}^+} - \frac{1}{q} \prod_i x_i^{c_{ij}^-} \right) \quad \text{(Eq. 4)}$$

where, $c^+$ and $c^-$ are the positive and negative elements of the stoichiometric matrix, q is the equilibrium constant and r(X) is the regulatory function for saturation, allostery, etc. [61]. Rate equation parameters published in units per hour were implemented in the whole cell model as units per minute. The rate equation for pyruvate dehydrogenase was implemented using irreversible mass action kinetics, as described by Nazaret et al. [63]. In addition, the malate-aspartate shuttle was included in the whole cell model in order to maintain NAD+ concentrations in the cytosol adequate to maintain flux through glycolysis. The rate equation for the malate-aspartate shuttle was implemented using irreversible mass action kinetics. A reaction for phosphate transport into the mitochondria has been included as well.

Boolean Modeling and Pseudo Dynamics for Signaling Pathways

Pathway models of more than a hundred species present significant challenges for most commonly applied modeling techniques. Foremost among the problems is that few interactions in a large pathway model have well characterized chemical kinetics, which eliminates many of the ordinary differential equation-based approaches. Experimental observations of cellular function indicate that the input-output behavior of many network types (ex. signaling) can be adequately approximated using the Heaviside, or step function [25]. Recent research has focused on applying rule-based Boolean models to the challenging problem of predicting biological network dynamics [26]. In a Boolean analysis, the nodes of the pathway representing species can have an active (1) or an inactive state (0). The network dynamics are determined by Boolean rules for each node, that determine the state of the node at the next time-step based on the state of the upstream nodes, and the nodal update strategy. Rule-based Boolean network models have been successfully used to aid in explaining experimentally observed robustness of cellular networks [25, 27, 28], and to determine the effects of an alteration in the network components and individual reaction rates [29]. The hybrid whole-cell model contains an important augmented Boolean pseudo-dynamics approach to identify and quantitatively rank the importance of a node using a Boolean description of a cellular interaction network. The approach, known as the Boolean Network Dynamics and Target Identification (BNDTI), combines network topology and dynamic state information to determine the relative importance of a particular node with respect to the overall response of the network [30]. While Boolean models offer a convenient tool to quantitatively model regulatory networks, current formulations have not been coupled with a HH to provide the capability to enable the simulation of AP response to perturbation of underlying cellular processes.

Figure 5:
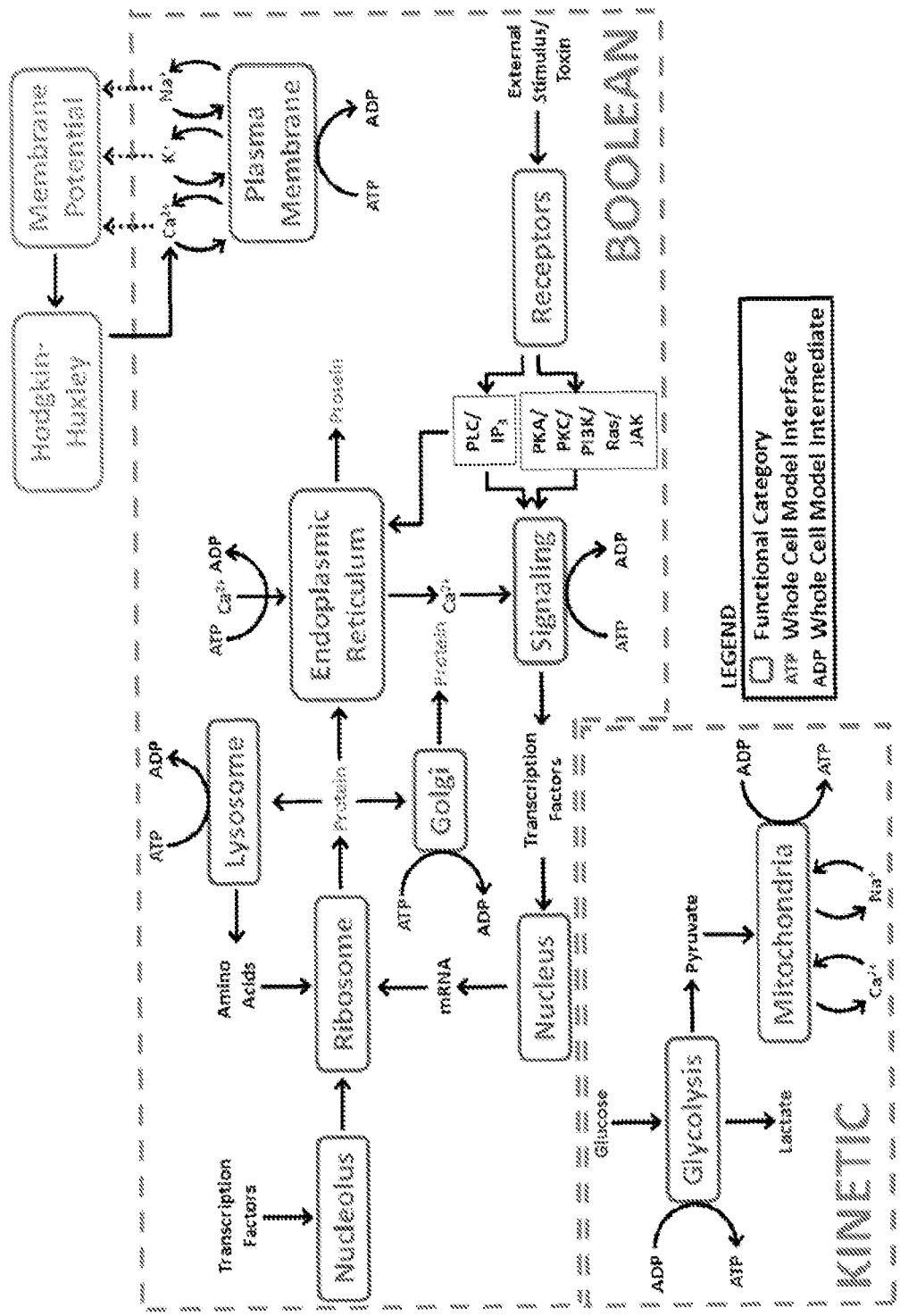
FIG. 5 illustrates the interaction of the chemical kinetics and Boolean dynamics within the whole cell model.

The ion channels and receptors that control membrane the potential and that mediate neuronal signaling exist on the plasma membrane. As most toxins target ion channels and receptors on the plasma membrane, the whole-cell model contains a hybrid Boolean and kinetic model of neuronal signaling on the plasma membrane. A Boolean function is used to describe the activation/inactivation of a plasma membrane ion channel or receptor as a response to a specific stimulus concentration. The kinetic function is used to describe the association/dissociation of the stimulus with the ion channel or receptor and the neuronal signaling mediated by the ion channel or receptor. These general stimuli were implemented as events in SimBiology®. The events can be modified to reflect specific experimental conditions. The interaction of the stimulus with a general plasma membrane receptor has been implemented as a rule in SimBiology®. The rule evaluates a Boolean function in a Matlab® file that is evaluated at each simulation step. For the stimulus of interest, additional details regarding its targets and its potency for its targets can be further specified in the Boolean function. In addition, the association/dissociation kinetics of the stimulus and its targets can be specified as a reaction in SimBiology®. The whole-cell model provides a conceptual hybrid Boolean and kinetic model of neuronal signaling on the plasma membrane that can be expanded to include other stimuli and their associated kinetics (FIG. 5).

The primary benefit from using a Boolean approach is the ability to incorporate all biological information at hand in one framework without a detailed knowledge of the underlying chemical kinetics. The interaction between nodes in the network is determined by a set of logical rules, based on connectivity. All interactions are characterized as logical operators (AND, OR, NOT), enabling automated translation of pathway files to logical rules. To obtain the logical rules, the SBML pathway model is used to obtain the reaction type between all pairs of species. The form of the logical rule is dictated by the reaction type, i.e., activation, inhibition or binding/association between species. Species activated by multiple other species form an OR rule, species inhibited by one or multiple other species form an AND NOT rule, and species binding/associating with other species form an AND rule. For example, the protein Ras of the mitogen-activated protein kinase (MAPK) signaling pathway may be activated by SOS, RasGRF, RasGRP, RapGEF, or PKC, but may be inhibited by Gap1m, p120GAP, or NF1. Therefore, the logical rule for Ras is:

(SOS OR RasGRF OR RasGRP OR RasGEF OR PKC) AND NOT (Gap1m OR p120GAP OR NF1)

Given the state of each of the species in this rule, it can be evaluated to determine the final state of the species Ras. The logical rule assigned to each species can be used in to simulate the system and generate Boolean state trajectories.

Figure 6:
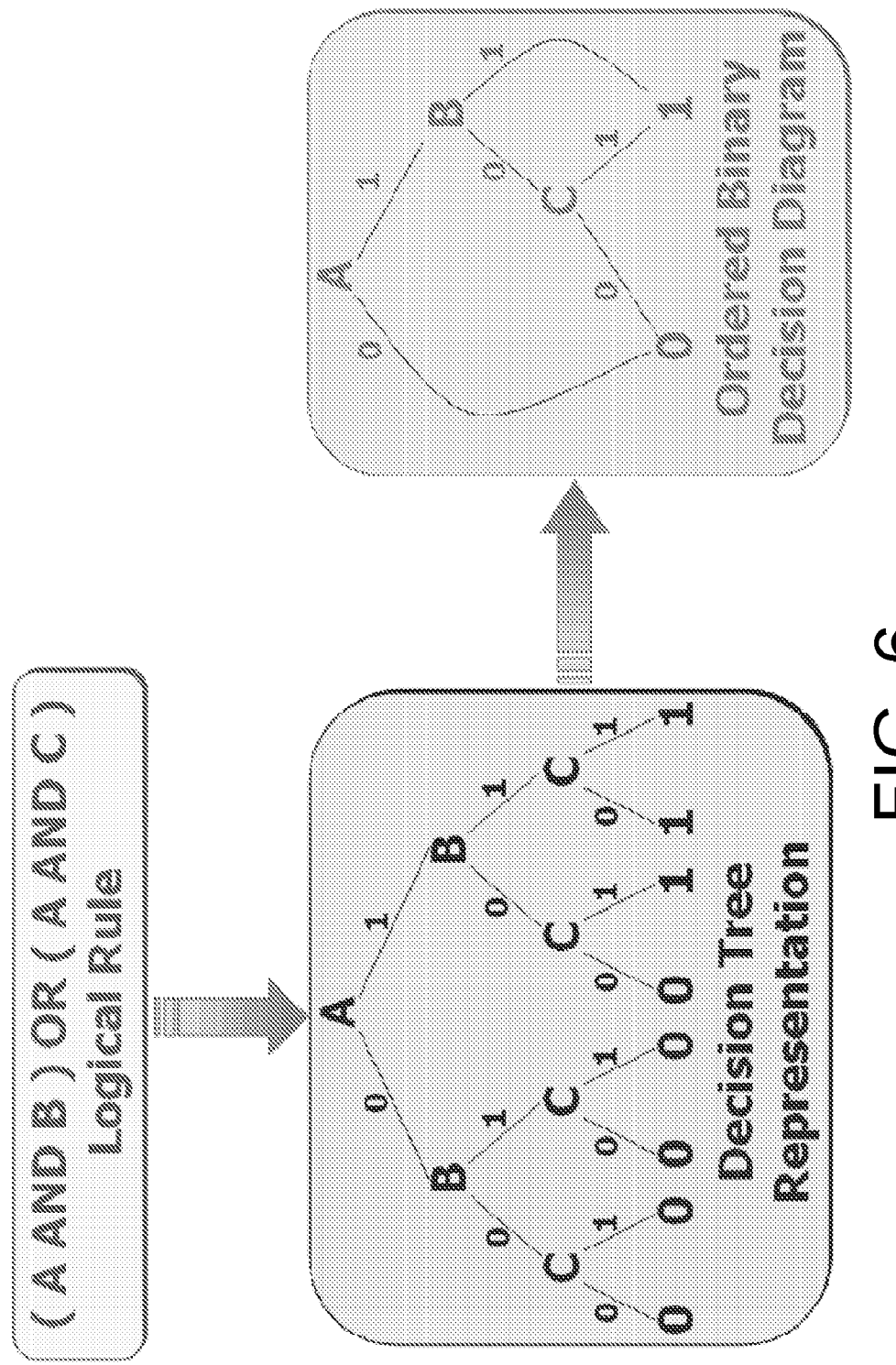
FIG. 6 is the conversion of a logical rule into an ordered binary decision diagram.

For rules that contain a series of combined operations, it is not computationally feasible to use the logical rule directly to evaluate the resultant state of the species, i.e., 0 or 1. In order to simplify and speed up the evaluation of complex rules we can convert the rule into a more efficient form known as an ordered binary decision diagram (OBDD). The algorithm proposed by Andersen and co-workers can be used to convert the logical rules into an OBDD, a compact, unique representation of a Boolean expression. In order to construct an OBDD, a decision tree representation of the logical rule is created by first setting the order of evaluation (in FIG. 6 the order of evaluation is A, B, and the C). Several redundant tests are evident in FIG. 6, where both the low branch (0) and high branch (1) branch lead to the same value. Many of the unnecessary tests can be removed and any reference to a redundant node can be replaced by a reference to an upstream node. Once all redundant tests are eliminated, the decision tree is converted into an OBDD. The resultant set of OBDDs are then stored for use during the simulation.

Having obtained the Boolean rules representing the inter-species interactions, the initial values of the network nodes can be assigned, the input/output nodes can be identified and their values fixed. In Boolean analysis, the nodes of the network represent the genes and can have an active (1) or an inactive state (0). Input nodes are specific nodes that have been identified as initiators of the stimulus/response, and output nodes are monitored to analyze the effect of the input node. The state of the input node is prescribed (fixed or time varying variable) throughout the simulation, and the initial values for all network nodes are randomly generated at the start of each simulation so that an ensemble of simulations can be performed to enable the characterization of the ensemble averaged network behavior [26-28, 45, 46]. This quantitatively ranks the importance of a node using a Boolean description of a cellular interaction network. The approach, known as the Boolean Network Dynamics and Target Identification (BNDTI), combines network topology and dynamic state information to determine the relative importance of a particular node with respect to the overall response of the network [30]. Once the system is initialized, it is ready for simulation using the pseudo-dynamic Boolean state update strategy.

In order to obtain the state trajectories, the individual nodes of the regulatory network are updated in a pseudo-dynamic manner at each time-step [26-28, 45, 46]. The update method is an asynchronous method [29, 47, 48]. This method assumes that the distribution of time-scales within the cellular system is Gaussian. Nodes are updated once during each time interval, with the update order being randomly selected at the beginning of each time step. Asynchronous updating is known to closely mimic the dynamic picture of cellular events, and has been shown to effectively capture rare events [26, 29]. The flexibility in an asynchronous update allows for one node to update once, whereas other nodes could be updated at a faster rate. The selection of the number of time-steps is governed by the ability to capture the system steady-state profile [26]. The output from BPD is an array of 0's and 1's describing the state trajectories in the system. In order to account for all possible statistical distributions of the randomized initial state, an ensemble of simulations is performed. The proposing team has observed that 10,000 simulations have generally proved to be sufficient.

In order to study the time-evolving features of the cellular response to stimuli, the static analysis based on network topology can be supplemented by a time-course dynamic simulation. In this regard the Boolean pseudodynamics algorithm is an excellent approach to study the dynamics of regulatory systems when kinetic information is unavailable. A commonly employed approach that is closest to a realistic network description is one that employs a continuous simulation strategy. In this regard, Glass and Kaufmann introduced a seminal technique hitherto referred as Glass dynamics [31, 32].

Glass dynamics provide a link between discrete Boolean and continuous ordinary differential equation models, with the advantage of not requiring a kinetic description of the underlying processes. The network node dynamics in the Glass dynamics simulation are described by an ordinary differential equation:

$$\frac{d\hat{A}_i}{dt} = -\hat{A}_i + F_i(A_1, A_2, \ldots, A_N) \qquad \text{(Eq. 5)}$$

Each equation is composed of two terms. The first term is an exponential decay term in the continuous variable, and the second term represents the Boolean transfer function F that captures the interaction with other nodes. This Boolean function is composed of discrete variables. Borrowing notation from Chaves and co-workers, we let $\hat{A}_i$ represent the continuous component of the variable associated with node I [49]. At each time instant the discrete variable $A_i$ is defined as a function of continuous variable according to a threshold value given as $A_i(t)=0$ for $\hat{A}_i(t)<=\theta$ and $A_i(t)=1$ for $\hat{A}_i(t)>\theta$. In these equations $\theta$ is bounded in the region (0, 1). The discrete variable represents whether the particular node is active or inactive, i.e., on or off, within the network. The limiting solution of the nodes is given by [0, 1] and this represents the situation signifying the absence, and maximum concentration of the nodal species, respectively. The parameter θ provides a link between the continuous and Boolean parts of the nodal dynamic equation. When $Â_i(t) > θ$, the Boolean variable is switched to the activated or on state, whereas it persists in the inactivated state otherwise. Thus the parameter θ determines the fractional level of maximum concentration required for the nodal species to function, and characterizes the continuous response of the system. It is also interesting to note that the steady-state solutions for both this hybrid method and the discrete asynchronous update BPD algorithm are the same.

The Glass dynamics model incorporates several additional components. Since the Glass dynamics equation is modeling an individual chemical species ($X_i$), that species (in general) participates in chemical reactions, represented in Eq. 6 by the kinetic rate. The species $X_i$ may also be affected by the action of individual cellular processes that is turned on/off depending on the state of the cell. Also, the time constant for the response of $X_i$ to the individual cellular process can vary significantly. The aforementioned dependences are included in the second term in Eq. 6. Finally, the background state decay rate that ensures the Glass dynamics system will attain the proper steady state is included as the final term in Eq. 6. The background decay rate is essential to achieving proper steady state, and has a tunable time constant.

$$\frac{dX_i}{dt} = \underbrace{r_{X_i}}_{\substack{\text{Specie} \\ \text{Rate}}} + \underbrace{\sum_{k=1}^{N_{Processes}} \alpha_k f(\tilde{X})}_{\substack{\text{Kinetic} \\ \text{Rate}}} \underbrace{\phantom{\sum}}_{\substack{\text{Boolean} \\ \text{Rate}}} - \underbrace{\frac{X_i}{\tau_i}}_{\substack{\text{State Decay} \\ \text{Rate}}} \qquad \text{(Eq. 6)}$$

All chemical species that interact with Boolean cellular processes use Eq. 6 to describe their kinetics. The remaining chemical species will use Equation 2 with the Boolean rate and state decay rates set to zero. Appropriate cellular process response coefficients, $\alpha_k$, and timescales for state decay rates, $\tau_i$, can be extracted from the literature, or available experimental data. FIG. 5 illustrates some of the chemical species that will interact with the Boolean description of the cellular processes, or functional categories.

Database With Simulated Action Potentials and Corresponding Model Parameters

A commercially available Structured Query Language (SQL) database is used to store simulation results from the hybrid whole-cell model with their corresponding model parameters. The stored data is comprised of simulated APs (0.5 s, resampled at 20 kHz) including eight characteristic values, the corresponding Boolean-model parameters of simulated cell-signalling cascades, scaling factors of metabolic processes, resulting ion and ATP concentrations as well as all parameters describing ion channel parameters for the HH model.

A method of using the whole cell model according to an embodiment of the invention will now be described. The method comprises preparing the whole-cell model, generating an AP database and using it to find a point of action of a substance. Portions of the method include:
(1) Calibration of the hybrid whole-cell model for a certain cell type
  (a) Fit HH-model parameters to match simulation results with recorded APs and membrane currents.
  (b) Calibrate metabolic reaction-kinetics with experimental or published data.
  (c) Cell-signaling cascades in the Boolean model can be adjusted to include/exclude specific signaling pathways of interest.
(2) The creation of a cell- and model-specific database
  (a) Specify s parameter space and intervals for selected parameters and variables in the entire whole-cell model.
  (b) Run simulations and store results as well as all parameters in a database.
    (i) Simulate APs with the whole-cell model for all combinations of specified parameters.
      1) Run hybrid of Boolean and metabolic model to determine ion and ATP concentration.
      2) Run HH-model with ion and ATP concentrations from previous step to generate APs.
    (ii) Save AP shape, characteristic values and all corresponding parameters in a database.
(3) Identify a substance's point(s) of action.
  (a) Measure multiple APs before, during and after drug/toxin application.
  (b) Search the database for closest matching (regarding the AP shape) entries and retrieve model parameters.
  (c) Interpret the retrieved information to reconstruct signaling and metabolic events inside and outside the cell under investigation.
  (d) Determine the drugs/toxins possible point(s) of action.

In certain embodiments of the invention, the method of using the whole cell model can be implemented using the internet. In those embodiments, the database can be provided by a server application and can be updated centrally. Further, a user such as a customer or licensor can use the database to identify a substance's point of action.

Example 1

This example calibrates the submodels for NG108/15 cells and generates an AP database for variations in cytosolic glycogenolysis and mitochondrial metabolism as well as parametric changes in the HH-model that reflect various cell sizes and experimental parameters.

Calibrating the HH-Model for Action Potentials from NG108-15 Cells

Figure 7:
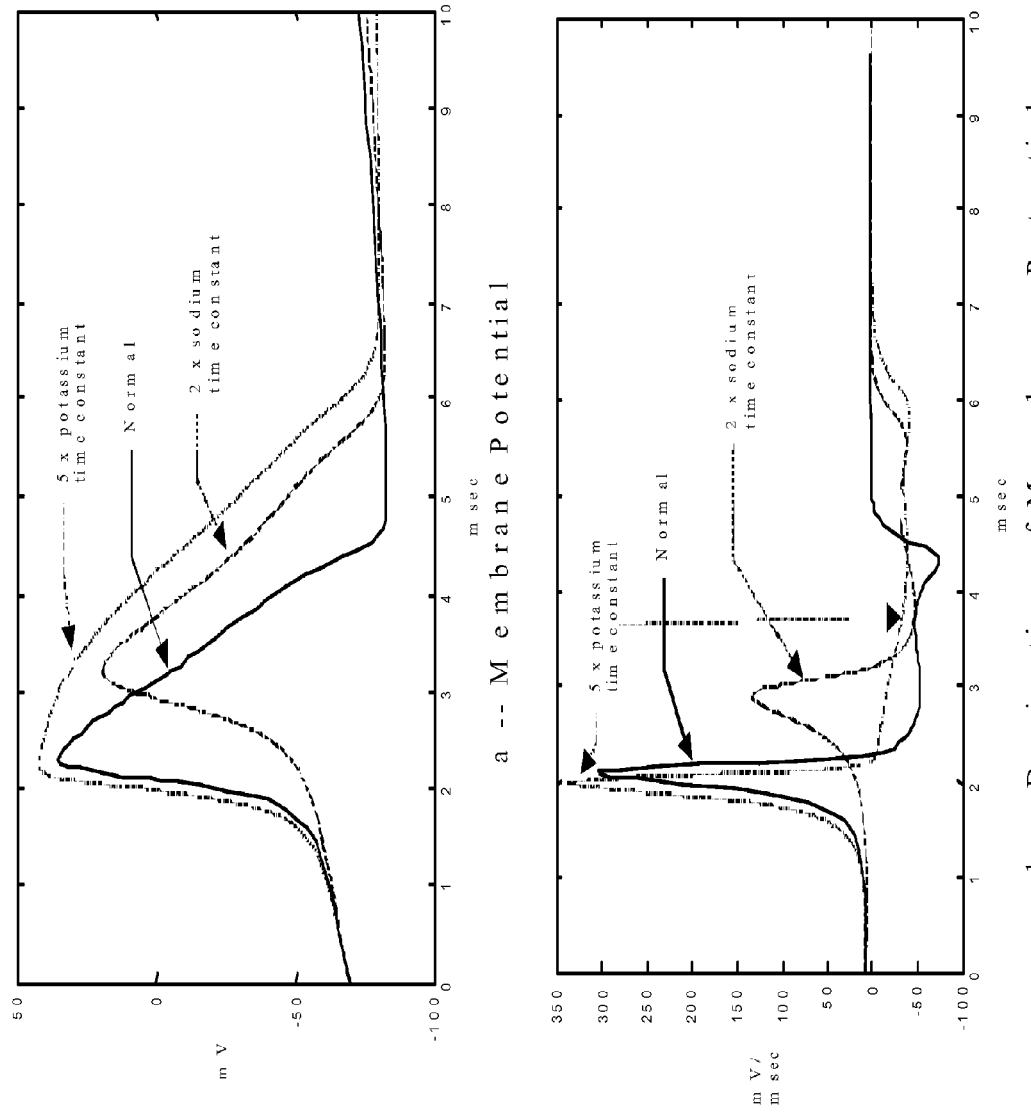
FIG. 7 shows Hodgkin-Huxley simulations that illustrate sensitivity of extracellular waveforms to changes in membrane time constants. The largest peak is from a simulation in which the potassium channel time constant was lengthened by a factor of five (note the longer after potential). The smallest of the peaks results from increasing the sodium time constant by a factor of two. The remaining peak is the normal 'textbook' Hodgkin-Huxley simulation.
Figure 8:
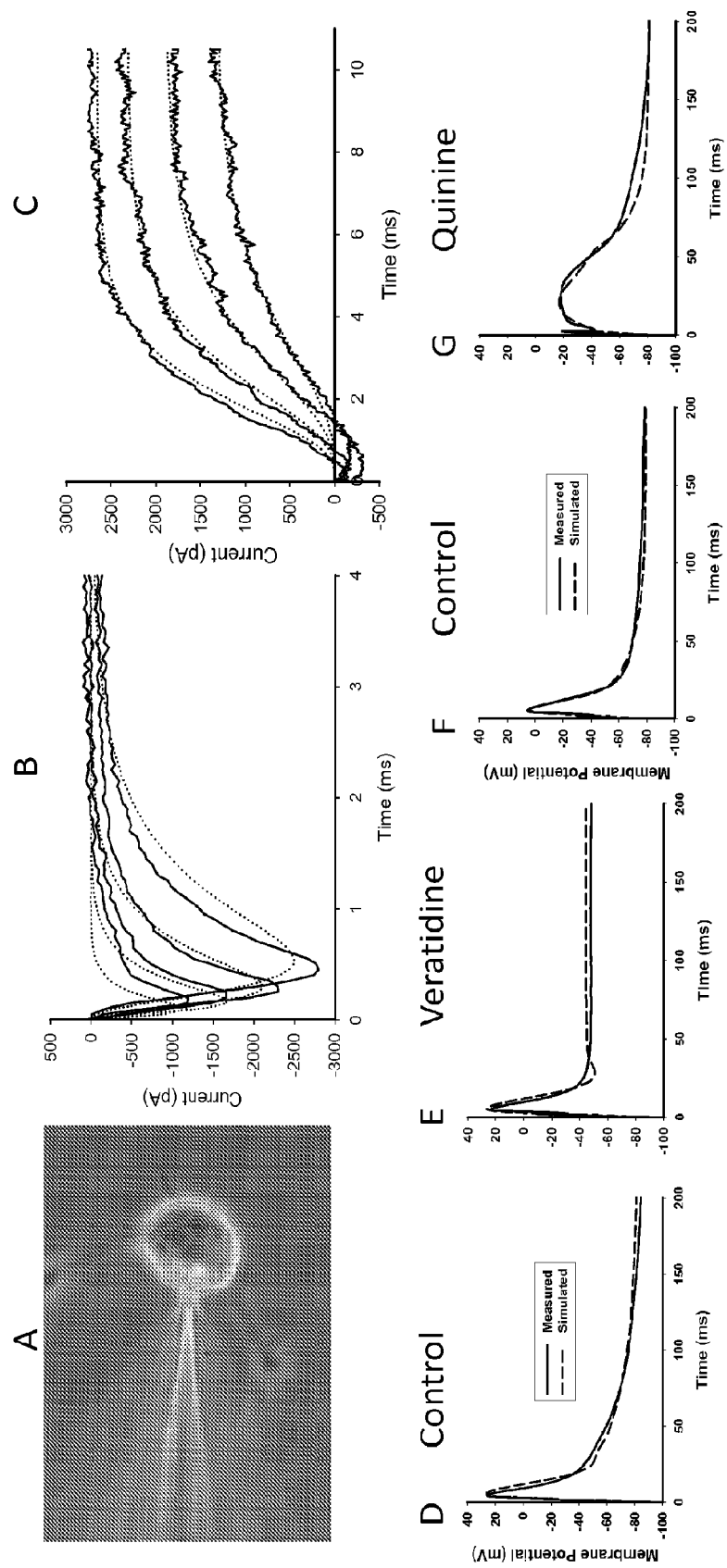
FIG. 8 is an estimation of ion channel parameters from voltage- and current-clamp experiments.
Figure 9:
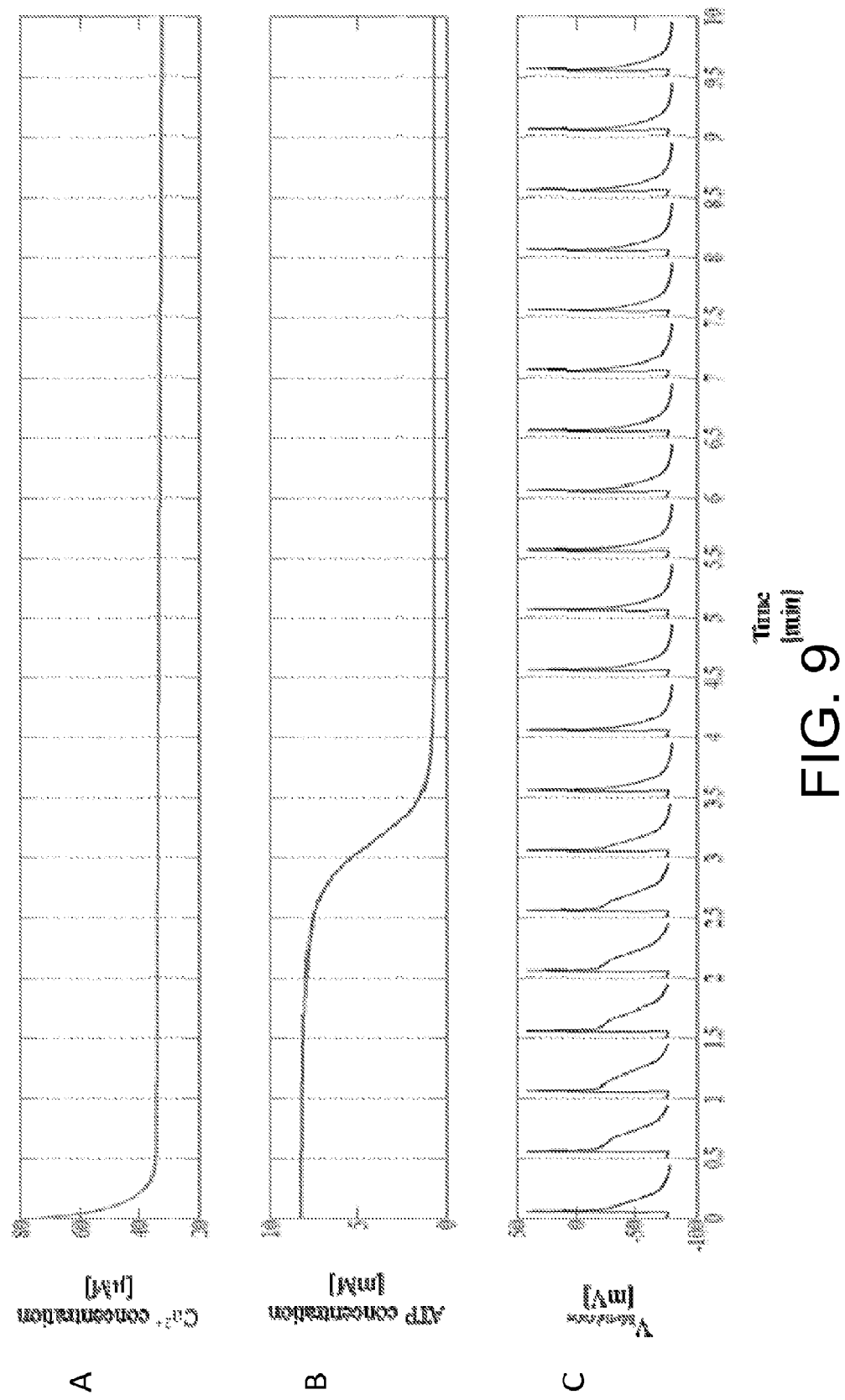
FIG. 9 is changes in the intracellular concentrations of Ca (FIG. 9A) and ATP (FIG. 9B) result in various AP shapes (FIG. 9C).

NG108-15 cells were cultured, experiments performed and model parameters filled according to published protocols [21, 60]. Exemplary data is provided in FIG. 7 as well as FIG. 8. Changes in intracellular ion or ATP concentrations lead to different AP shapes, as depicted in FIG. 8.

Calibrating the Metabolic Model

NG108-15 cells were cultured according to [21]. In addition to the published standard plating on coverslips, 1,000,000 cells were plated in either 6 or 12 75 cm T-flasks for differentiation. After 4 days in differentiation, the culturing media was replaced by 1 ml of the published [21] extracellular solution used during patch-clamp experiments. The extracellular solution includes 10 mM 2-Desoxy-Glucose (2DG). 2DG is favored over glucose by the glucose transporters, located in the cell membrane. In contrast to glucose, 2DG cannot be used by the cell to generate energy and thus affects the cellular metabolism.

For cells on coverslips, 20 μl samples of extracellular solution were taken right after the application of 2DG and every 20 minutes for 4 hours and stored in a freezer at −20° C. After 4 hours the frozen samples were thawed in order to determine the concentrations of glucose/2DG and lactate using commercially available standard calorimetric kits.

After 4 days in differentiation, the media of cells in T-flasks was replaced by the published extracellular solution, including 10 mM 2DG. The first Cells in the first T-flask were lysed immediately to determine the intracellular ATP concentration using commercially available ATP kits. Every 30 min, cells in another T-flask were lysed for ATP experiments. The ATP-containing analytes were stored at −20° C. until all samples were collected. The ATP concentrations were determined using calorimetric ATP kits.

Figure 10:
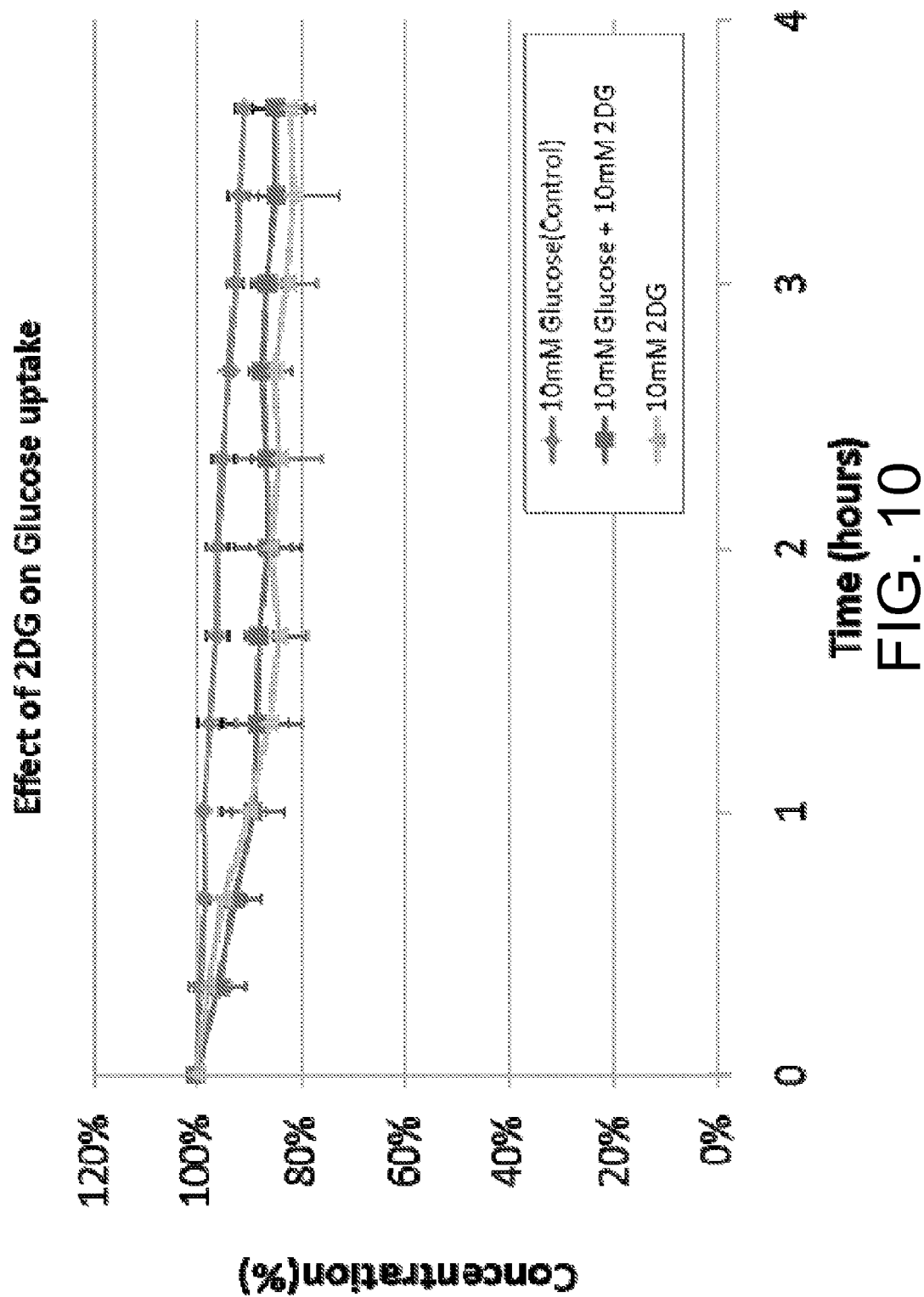
FIG. 10 shows results from experiments performed for the calibration of the metabolic model.
Figure 11:
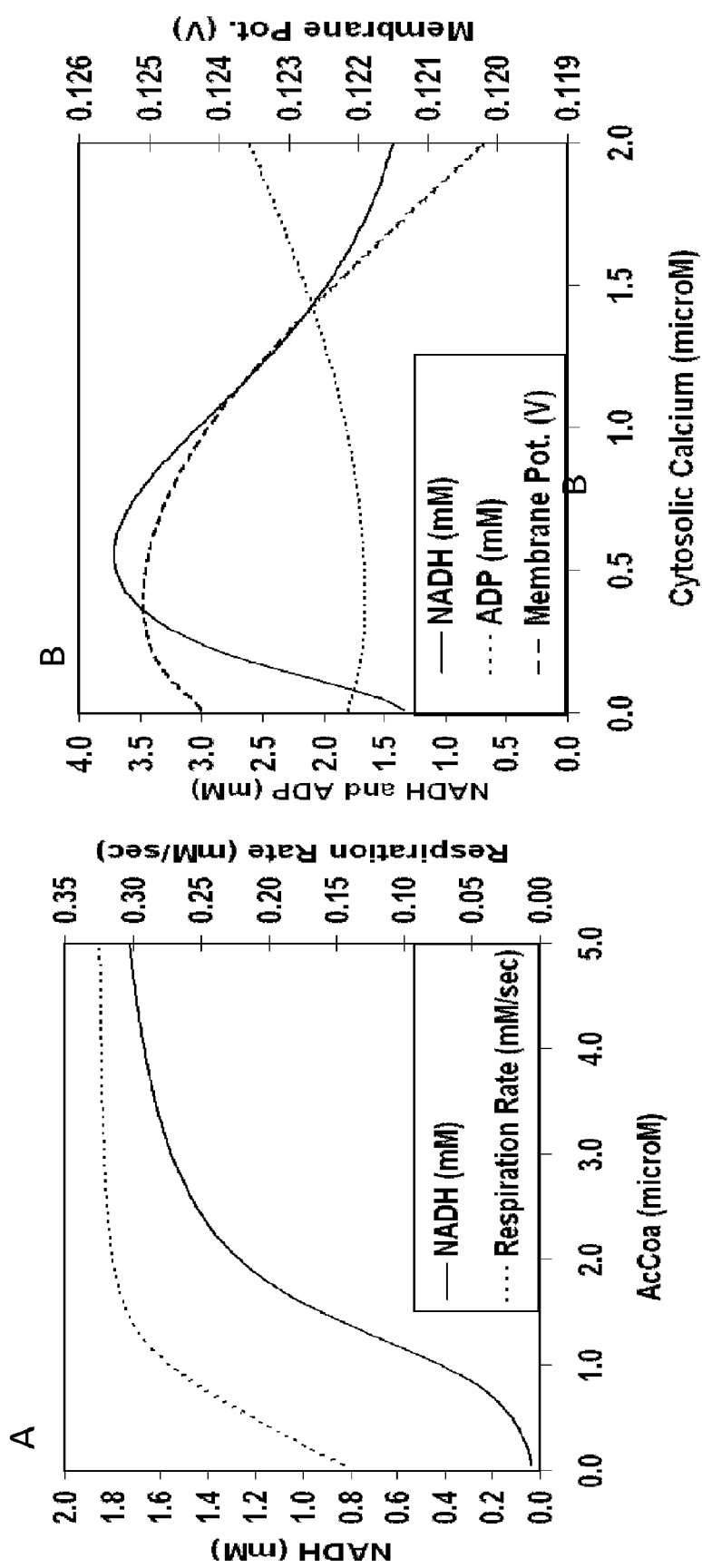
FIG. 11 is (FIG. 11A) Dependence of the mitochondrial model on the concentration of AcCoA, and (FIG. 11B) cytosolic calcium.
Figure 12:
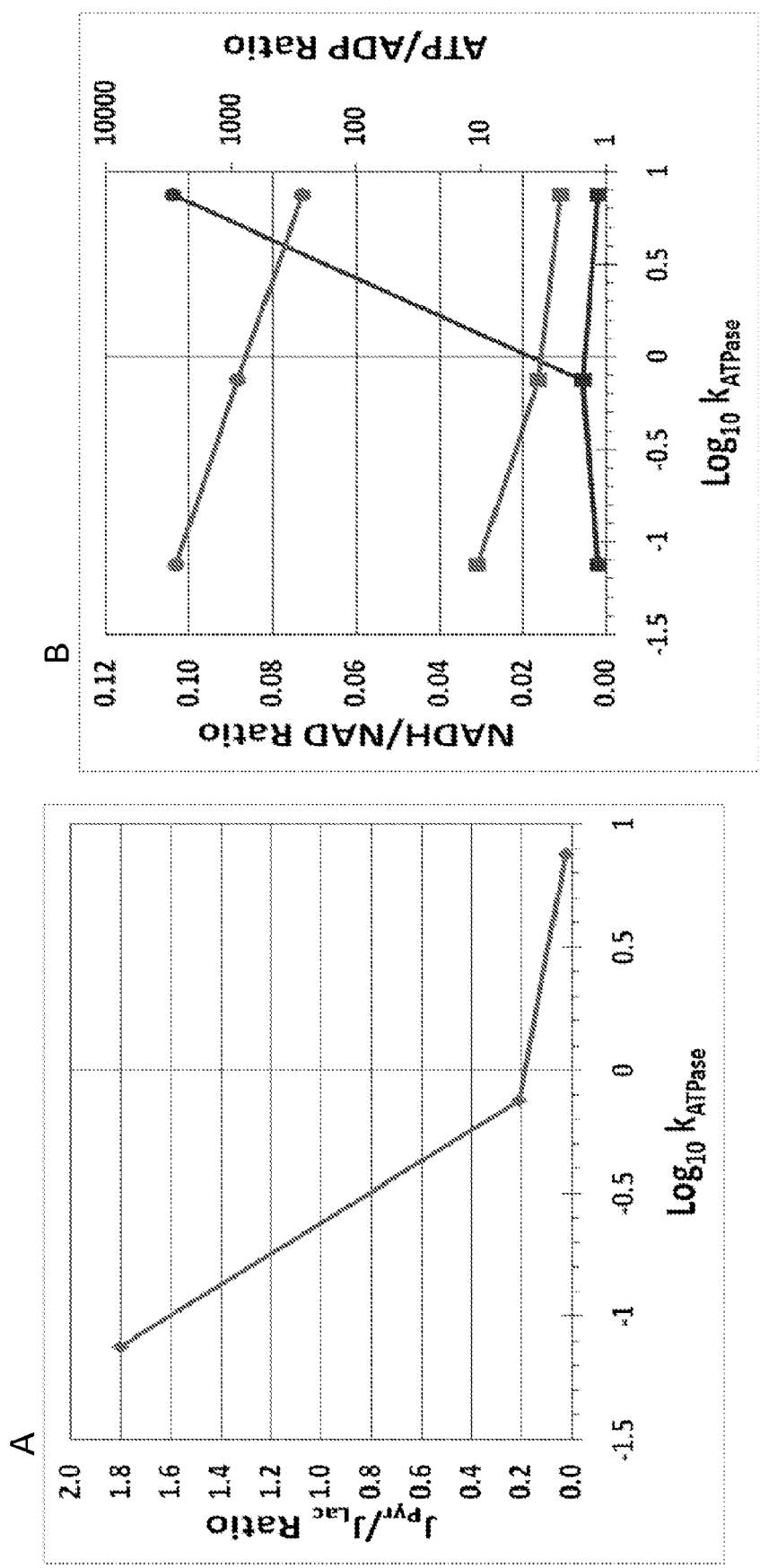
FIG. 12 is data indicating that increased ATP consumption causes the cell to (FIG. 12A) favor lactate dehydrogenase flux over pyruvate dehydrogenase flux.

The results for concentration changes of glucose/2DG (exemplary dataset is shown in FIG. 10), lactate and ATP over time were used to calibrate of the Boolean-metabolic model hybrid. The activity-parameters of the cellular glycogenolysis $S_{Gly}$ and the mitochondrial metabolism $S_{Mit}$ were fitted until the simulated glucose consumption, simulated extracellular lactate concentrations and the simulated intracellular ATP concentration matched the experimental results. The full metabolic model has been examined under increased nutrient, cytosolic Ca2+ (FIG. 11), and ATP load (FIG. 12). Increased ATP consumption has been widely recognized to induce stimulation of respiration. It lowers ATP/ADP ratio in the cell (FIG. 11A), which could (a) stimulate ATP synthase (FIG. 11B), such that mitochondrial membrane potential ($\Delta\psi_m$) decreases and respiration increases, (b) stimulate citric acid cycle dehydrogenases or (c) stimulate glycolysis (FIG. 12A), and thus increase substrate for respiration [36]. As ATP consumption increases, the metabolic model favors flux through lactate dehydrogenase over flux through pyruvate dehydrogenase (FIGS. 12A & B).

Selecting Boolean/Glass Dynamics for Signaling Cascades

Figure 13:
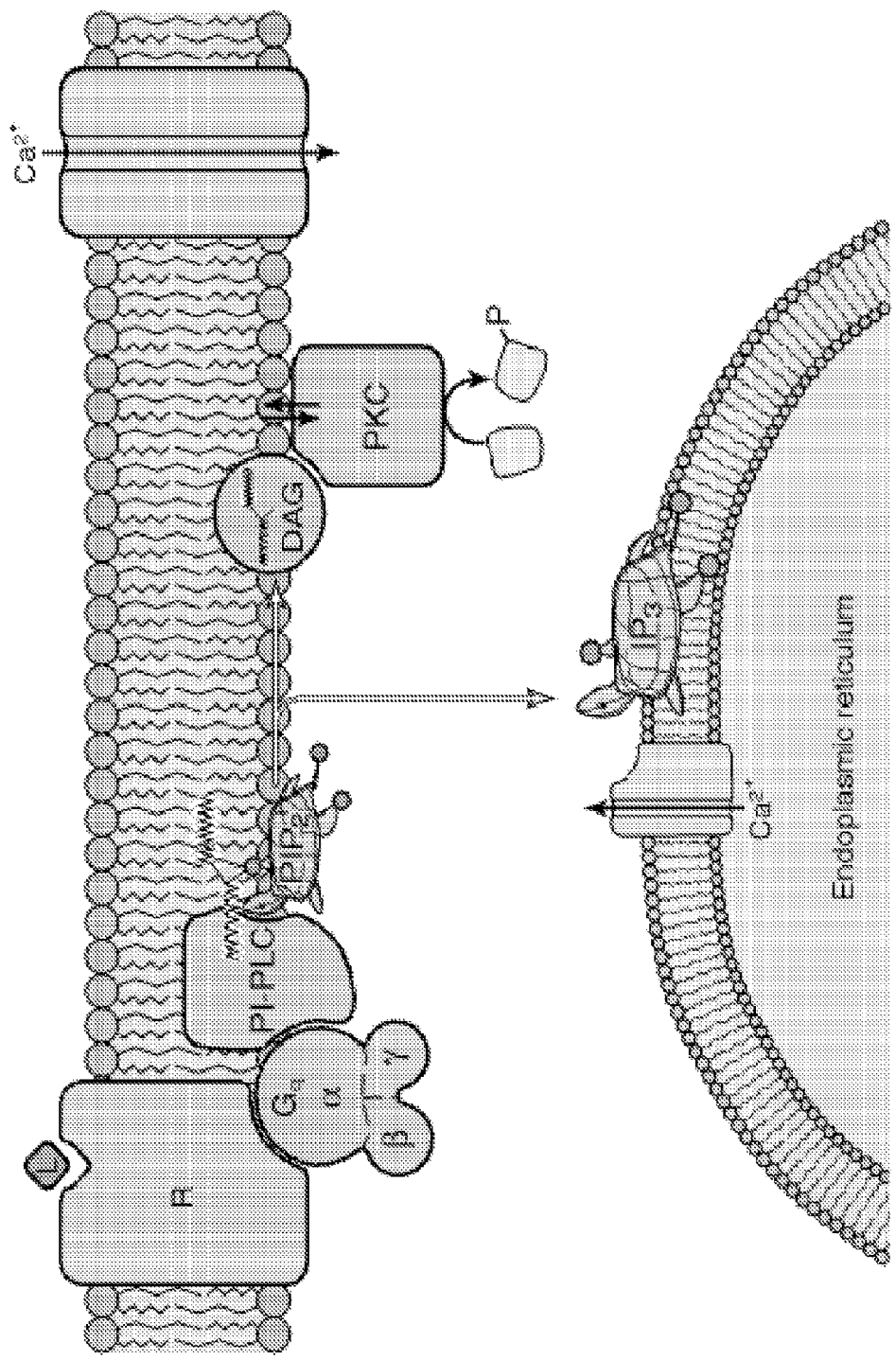
FIG. 13 is an Illustration of PLC conversion of PIP2 to IP3 and DAG. IP3 binds the IP3R calcium channel on the endoplasmic reticulum, through which endoplasmic reticulum calcium is released into the cytosol [62].

The activation/inhibition of the general plasma membrane receptor, i.e., serotonergic receptors (5-HT$_2$), adrenergic receptors ($\alpha_1$), calcitonin receptor, histamine receptor (H$_1$) or muscarinic receptors (M$_1$, M$_3$, M$_5$), was coupled with the activation of phospholipase C (PLC), which converts phosphatidylinositol 4,5-bisphosphate (PIP$_2$) to inositol 1,4,5-triphosphate (IP$_3$) and diacylglycerol (DAG) (FIG. 13). The rate equation for the hydrolysis of PIP$_2$ to IP$_3$ and DAG by PLC was implemented using Michaelis-Menten kinetics and multiplied by its Boolean value. Therefore, when the Boolean value is zero, the reaction rate is zero, and when the Boolean value is one, the reaction rate is, $$v = V_{max} * \left( \frac{[PIP_2]}{K_m + [PIP_2]} \right) \quad \text{(Eq. 7)}$$

Figure 3:
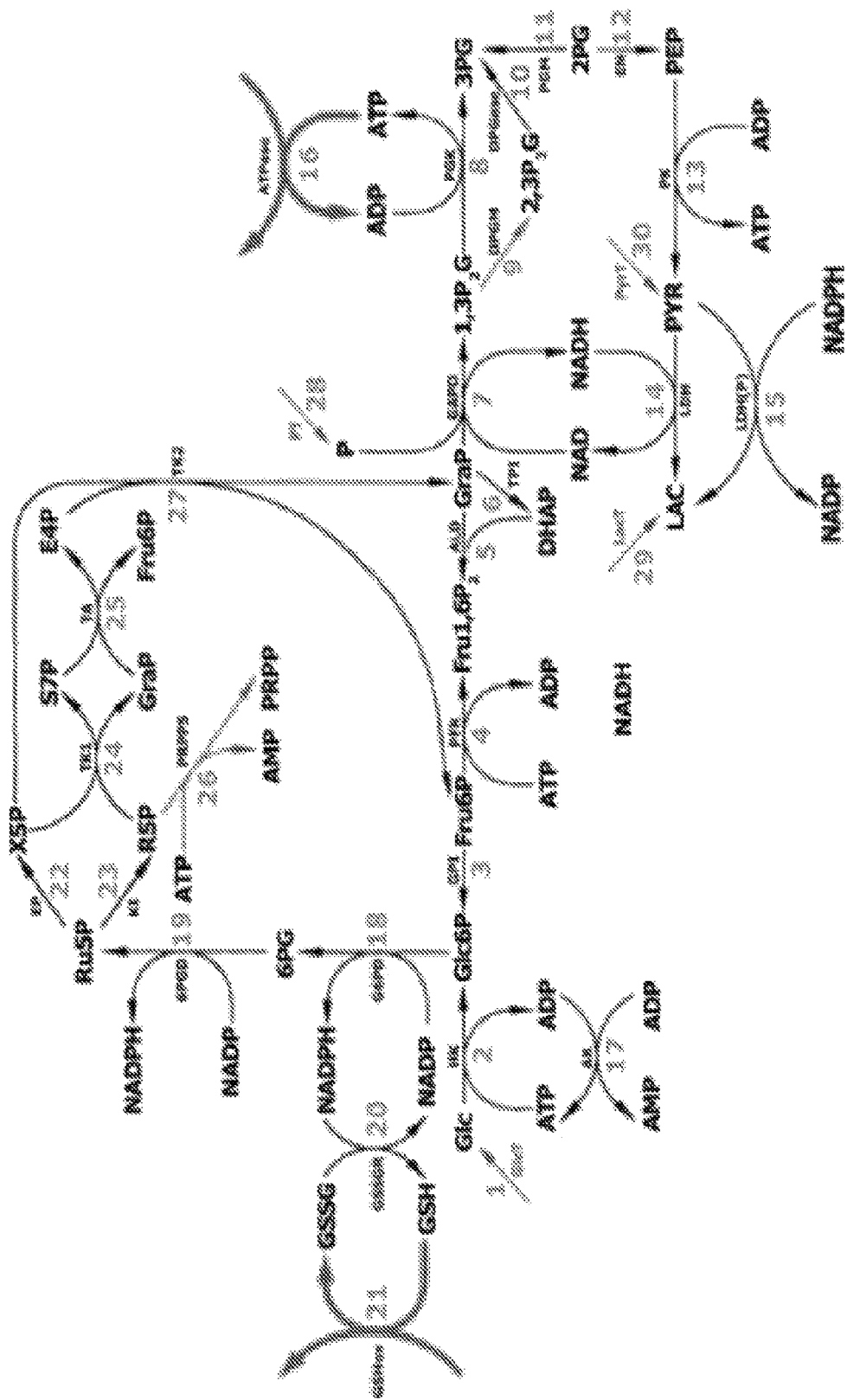
FIG. 3 is a Glycolysis model [33] used in the development of a whole cell model. The glycolysis model consists of thirty reactions, involving 29 reactants.
Figure 4:
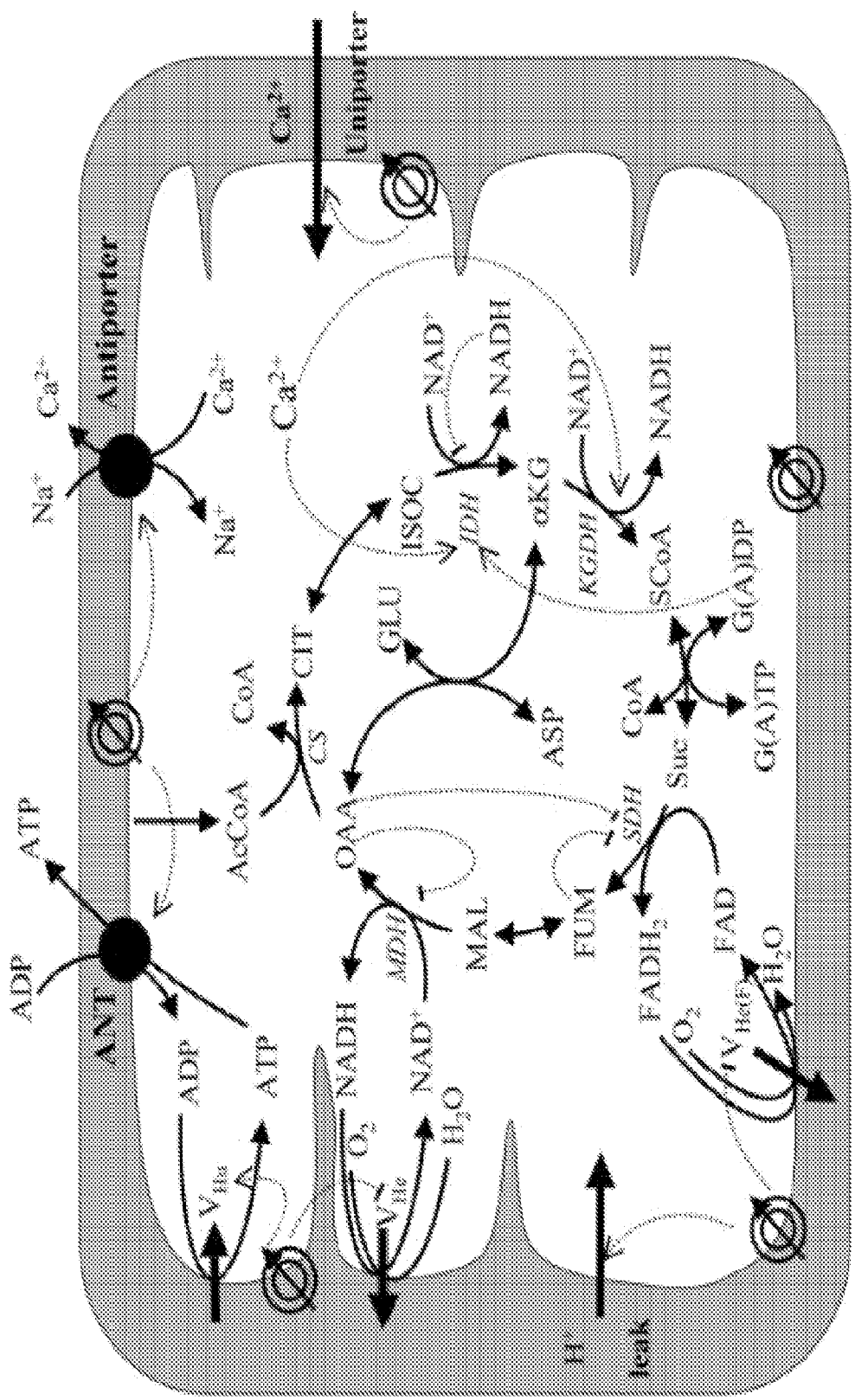
FIG. 4 is a model of mitochondrial metabolism [34] used in the development of a neuronal whole cell model.

This example also includes the implementation of a simple rate equation for IP$_3$ and DAG consumption, which used mass action kinetics. IP$_3$, then, activates IP$_3$R calcium channels on the endoplasmic reticulum membrane, through which endoplasmic reticulum calcium is released into the cytosol (FIG. 3). A primary ion involved in both the control of membrane potential and the mediation of neuronal signaling is calcium. While the flux of calcium to and from the mitochondria has been addressed by the implementation of the mitochondrial metabolism model [34], we have addressed the endoplasmic reticulum calcium flux by implementing reactions from Marhl et al. [58]. We modified the reaction rate of the IP$_3$R calcium channel from Chen et al. [59] to include a dependence on IP$_3$, which was absent from the channel reaction rate from Marhl et al. Calcium dynamics are important in the development of the neuronal whole cell model, as the action of many toxins includes prolonged increases in cytosolic calcium.

Classification of Action Potentials

The shape of recorded and simulated APs is characterized by eight characteristic values: the initial membrane voltage, the maximum amplitude, the AP width at half-max, the voltage at four distinct time points in steps of 25 ms after the stimulation as well as the tail potential. A classification of recorded action potentials is performed by a closest-match search in the database, given the eight characteristic AP values.

Generating the Action-Potential Database

Figure 14:
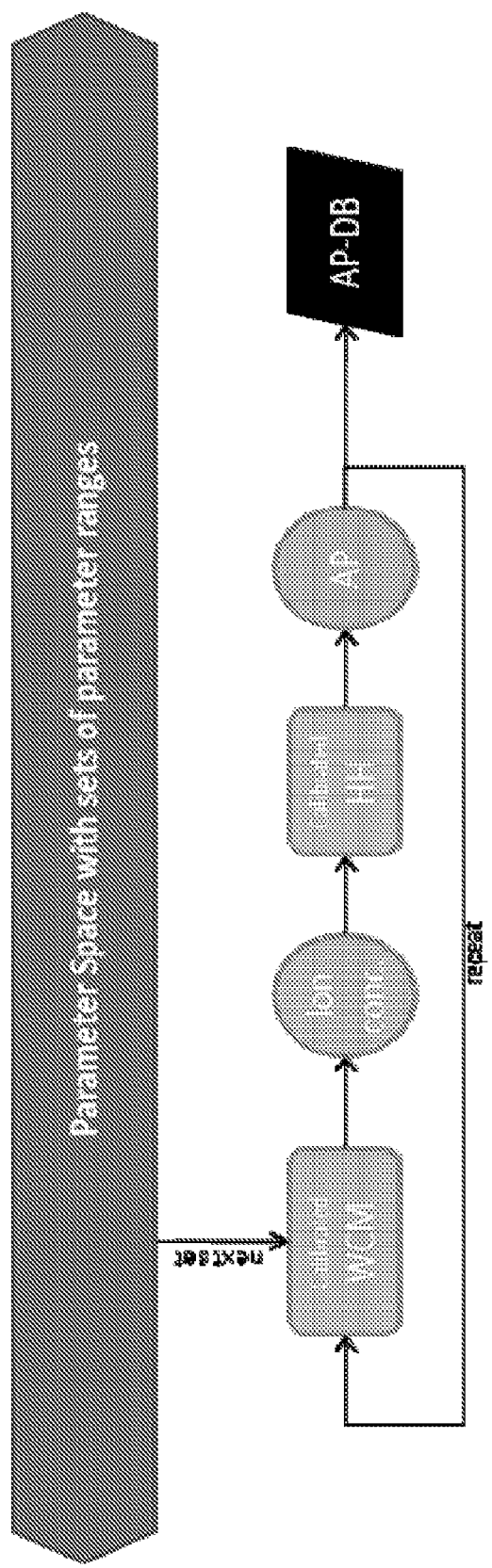
FIG. 14 is a schematic illustration of the database generation: Ranges of variable parameters (e.g. intracellular $Na^+$, $K^+$, $Ca^{2+}$, but also source of carbon, energy levels [ATP] or [NADH], and so forth) were used to run the whole cell model. The resulting ion concentrations were used as inputs for the HH model to generated action potentials. The action potential shape was saved in the AP-DB along with all parameters that were set to generate it. Subsequently, a new set of parameters was used to run the hybrid whole-cell model again. (The AP-DB needs to be regenerated whenever the whole cell or the HH model are changed.)

The calibrated and adjusted submodels were used in concert to create action potentials based on simulated intracellular ion and ATP concentrations (FIG. 14). A 9-dimensional parameter space was selected with ranges as listed in Table 1. The simulated APs were evaluated for their 8 characteristic values and added to the database including all parameters used to create the output.

TABLE 1

Exemplary parameter space for database generation. Simulation outputs were generated for every possible combination.

| variable | minimum | maximum | step size |
|---|---|---|---|
| $S_{Mit}$ | 0.80 | 1.20 | 0.05 |
| $S_{Gly}$ | 0.20 | 1.60 | 0.20 |
| $S_E$ | 0 | 1 | 1 |
| $C_M$ | 10 pF | 50 pF | 5 pF |
| $g_l$ | 0.01 mS | 0.10 mS | 0.01 mS |
| $g_{Na}$ | 75 mS | 175 mS | 25 mS |
| $g_K$ | 10 mS | 50 mS | 10 mS |
| $g_{KATP}$ | 10 mS | 50 mS | 5 mS |
| $g_{Ca}$ | 5 mS | 50 mS | 5 mS |

Using the Database to Determine Cellular and Metabolic Parameters

Figure 15:
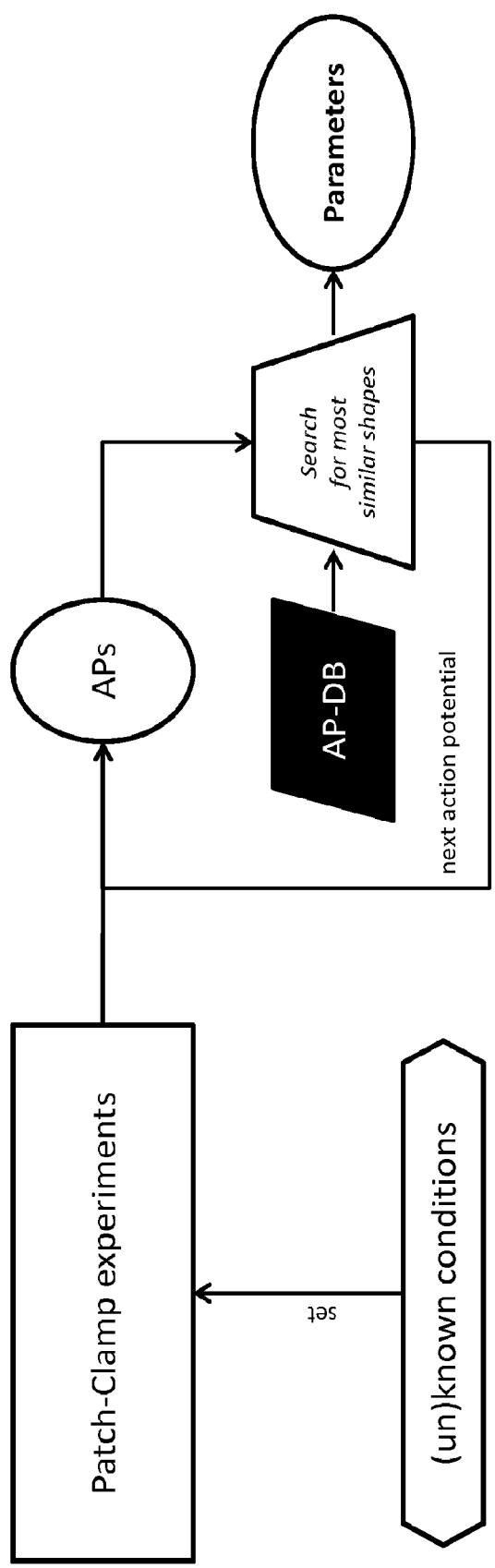
FIG. 15 is a schematic for AP database application in the quest for target-points of drugs or toxins: Measured action potentials are scanned for meaningful values, which are then compared with the meaningful values of previously generated action potentials in the AP-DB. The AP-DB also contains the model parameters that created the specific action-potential shape. Changes, in these parameters for continuously measured action potentials indicate the influence of unknown conditions and can also be verified by known conditions.
Figure 16:
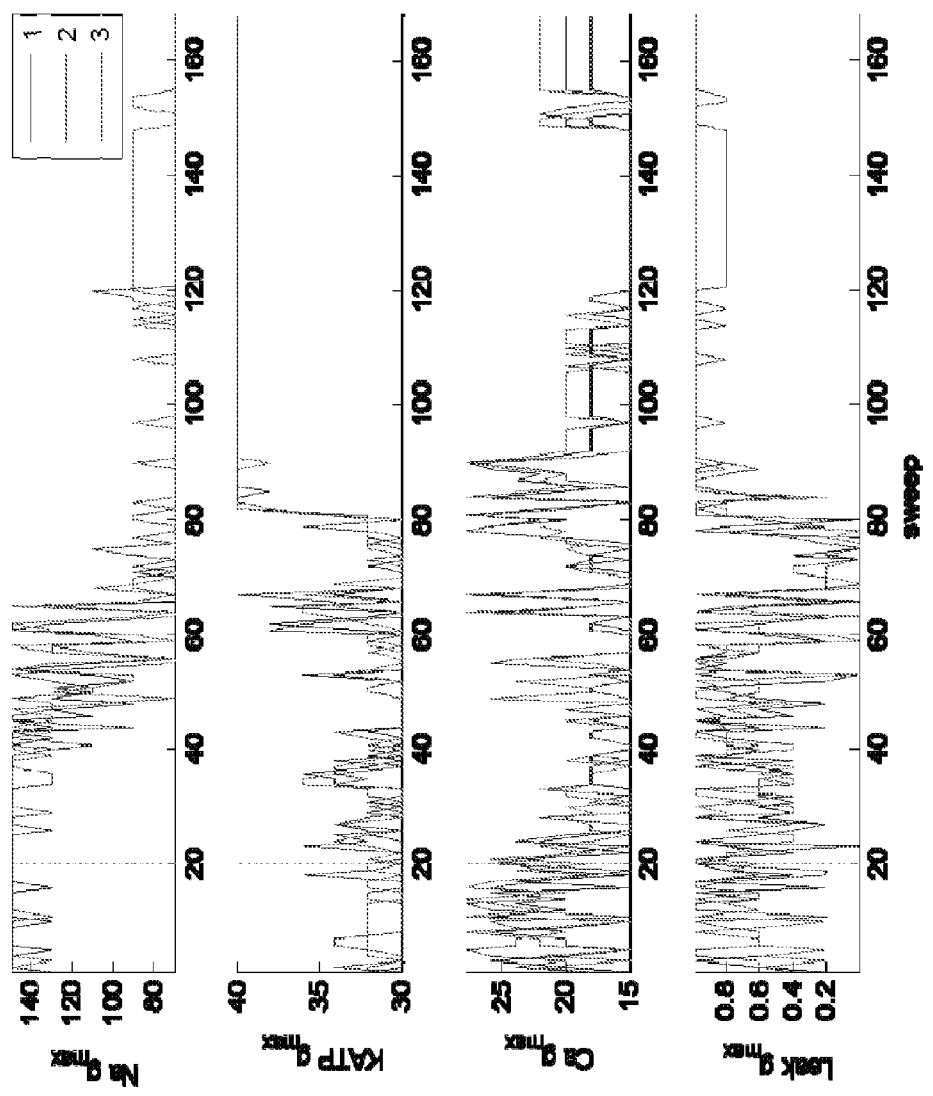
FIG. 16 shows results for APs recorded from an NG108-15 cell treated with cyanide.
Figure 17:
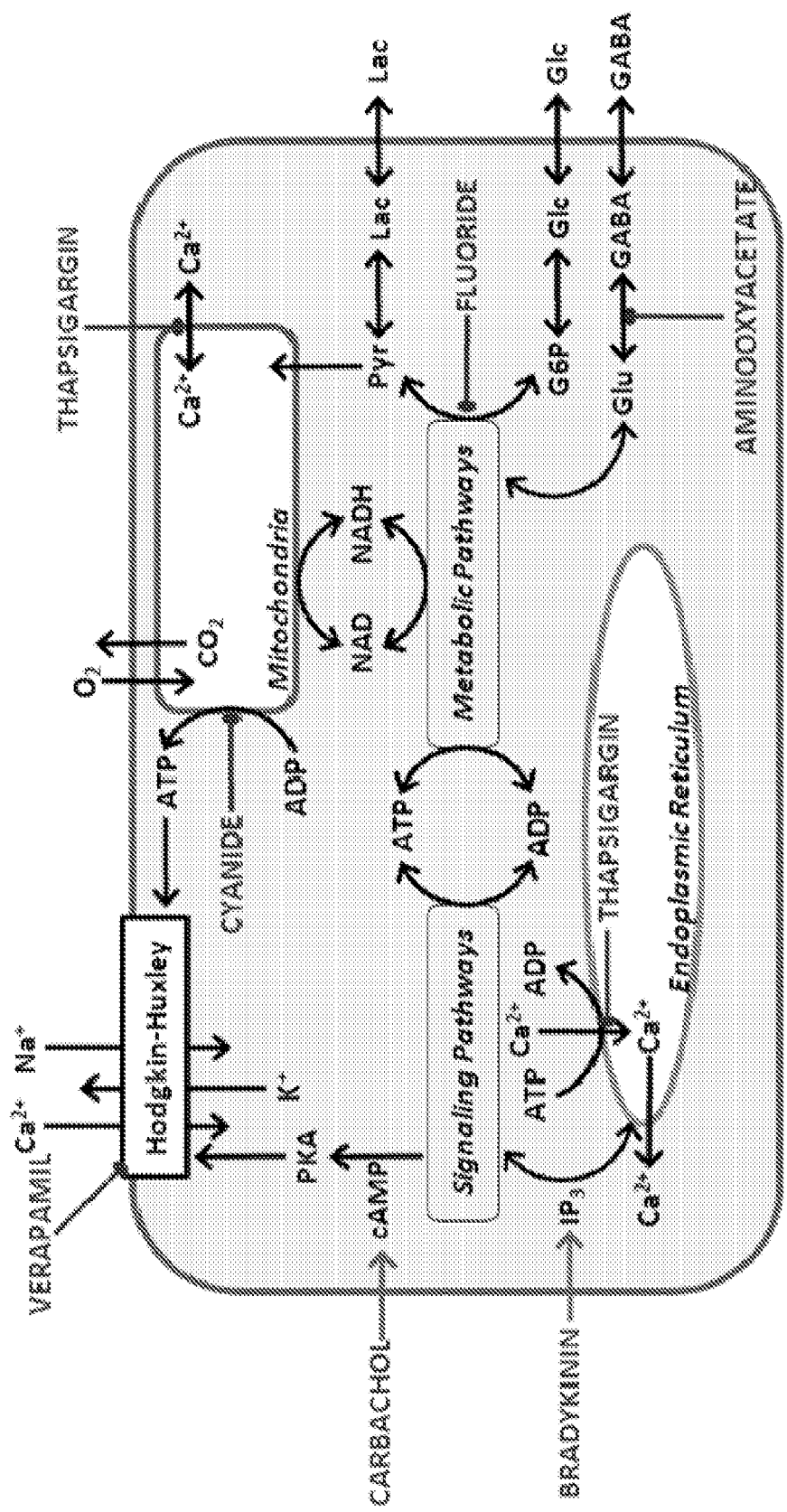
FIG. 17 is a schematic of relevant processes associated with exemplary compounds.

The culturing media of differentiated NG108-15 cells (after 4 DIV) was replaced by extracellular solution. APs were recorded before a toxin (cyanide) was applied. 164 consecutively recorded APs were evaluated by searching the database for three closest matches for each of the APs. FIG. 15 illustrates the extraction of parameters from the database. The changes for HH-parameters are depicted in FIG. 16. The parameters associated with the found matches describe a decrease in calcium currents, followed by a slow decrease in sodium currents, which lead to a steep increase in general leak and ATP-gated potassium currents. These results indicate cell death due to poisoning by a toxin. Other exemplary drugs and their points of action are depicted in FIG. 17.

With this disclosure in mind, wherein metabolic activity has been investigated by means of glucose uptake, lactate output and ATP production, we further envision that the presently disclosed invention will be applicable to cell modeling where the stimuli include but are not limited to NAD/NADH, pyruvate, phosphate and calcium metabolism, as well as to gene transcription and various signaling pathways.

The present invention has been described hereinabove with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical figures expressed herein are intended to be approximate and not an exact or critical figure unless expressly stated to the contrary.

Further, any publications, patent applications, patents, and other references mentioned herein are incorporated by reference in their entirety as if they were part of this specification. However, in case of conflict, the present specification, including any definitions, will control. In addition, as noted above, materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Therefore, in the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

Any element in a claim that does not explicitly state "means for" performing a specified function, or "step for" performing a specified function, is not to be interpreted as a "means" or "step" clause as specified in 35 U.S.C. §112, ¶ 6. In particular, the use of "step of" claims herein is not intended to invoke the provisions of 35 U.S.C. §112, ¶ 6.

BIBLIOGRAPHY

1. Bentleya, A and Atkinsona, A, *Whole cell biosensors electrochemical and optical approaches to ecotoxicity testing*. Toxicol. In Vitro, 2001. 15: p. 469-475.
2. Bousse, L, *Whole cell biosensors*. Sens. Actuators B: Chem., 1996. 34((1-3)): p. 270-275.
3. Offenhausser, A and Knoll, W, *Cell-transistor hybrid systems and their potential applications*. Trends Biotechnol, 2001. 19(2): p. 62-6.
4. Stett, A, Egert, U, Guenther, E, Hofmann, F, Meyer, T, Nisch, W, and Haemmerle, H, *Biological application of microelectrode arrays in drug discovery and basic research*. Anal Bioanal Chem, 2003. 377(3): p. 486-95.
5. Gross, G W and Harsch, A, *Odor, drug and toxin analysis with neuronal networks in vitro: extracellular array recording of network responses*. Biosens. Bioelectron., 1997. 12(5): p. 373-393.
6. Morefield, S I, Keefer, E W, Chapman, K D, and Gross, G W, *Drug evaluations using neuronal networks cultured on microelectrode arrays*. Biosens Bioelectron, 2000. 15(7-8): p. 383-96.
7. van Soest, P F and Kits, K S, *Conopressin affects excitability, firing, and action potential shape through stimulation of transient and persistent inward currents in mulluscan neurons*. J Neurophysiol, 1998. 79(4): p. 1619-32.
8. Spencer, C I, Yuill, K H, Borg, J J, Hancox, J C, and Kozlowski, R Z, *Actions of pyrethroid insecticides on sodium currents, action potentials, and contractile rhythm in isolated mammalian ventricular myocytes and perfused hearts*. J Pharmacol Exp Ther, 2001. 298(3): p. 1067-82.
9. Martin-Caraballo, M and Greer, J J, *Development of potassium conductances in perinatal rat phrenic motoneurons*. J Neurophysiol, 2000. 83(6): p. 3497-508.
10. Djouhri, L and Lawson, S N, *Changes in somatic action potential shape in guinea-pig nociceptive primary afferent neurones during inflammation in vivo*. J Physiol, 1999. 520 Pt 2: p. 565-76.
11. Muraki, K, Imaizumi, Y, and Watanabe, M, *Effects of noradrenaline on membrane currents and action potential shape in smooth muscle cells from guinea-pig ureter*. J Physiol, 1994. 481 (Pt 3): p. 617-27.
12. Stockwell, B R, *Exploring biology with small organic molecules*. Nature, 2004. 432(7019): p. 846-854.
13. Bender, A, Scheiber, J, Glick, M, Davies, J W, Azzaoui, K, Hamon, J, Urban, L, Whitebread, S, and Jenkins, J L, *Analysis of pharmacology data and the prediction of adverse drug reactions and off-target effects from chemical structure*. Chemmedchem, 2007. 2(6): p. 861-873.
14. Arnone, M I and Davidson, E H, *The hardwiring of development: organization and function of genomic regulatory systems*. Development, 1997. 124(10): p. 1851-64.
15. Armstrong, D L and Rossie, S, *Ion channel regulation. Introduction*. Adv Second Messenger Phosphoprotein Res, 1999. 33: p. ix-xx.
16. Orlov, S N and Hamet, P, *Intracellular monovalent ions as second messengers*. J Membr Biol, 2006. 210(3): p. 161-72.
17. Rosati, B and McKinnon, D, *Regulation of ion channel expression*. Circ Res, 2004. 94(7): p. 874-83.
18. Hsiao, C F, Wu, N, and Chandler, S H, *Voltage-dependent calcium currents in trigeminal motoneurons of early postnatal rats: modulation by 5-HT receptors*. J Neurophysiol, 2005. 94(3): p. 2063-72.
19. Selivanov, V A, Alekseev, A E, Hodgson, D M, Dzeja, P P, and Terzic, A, *Nucleotide-gated KATP channels integrated with creatine and adenylate kinases: amplification, tuning and sensing of energetic signals in the compartmentalized cellular environment*. Mol Cell Biochem, 2004. 256-257(1-2): p. 243-56.
20. Soundarapandian, M M, Zhong, X, Peng, L, Wu, D, and Lu, Y, *Role of K(ATP) channels in protection against neuronal excitatory insults*. J Neurochem, 2007. 103(5): p. 1721-9.
21. Mohan, D K, Molnar, P, and Hickman, J J, *Toxin detection based on action potential shape analysis using a realistic mathematical model of differentiated NG108-15 cells*. Biosensors & Bioelectronics, 2006. 21(9): p. 1804-1811.
22. Greenstein, J L and Winslow, R L, *An integrative model of the cardiac ventricular myocyte incorporating local control of Ca2+ release*. Biophys J, 2002. 83(6): p. 2918-45.
23. Slepchenko, B M, Schaff, J C, Macara, I, and Loew, L M, *Quantitative cell biology with the Virtual Cell*. Trends Cell Biol, 2003. 13(11): p. 570-6.
24. Winslow, R L, Cortassa, S, and Greenstein, J L, *Using models of the myocyte for functional interpretation of cardiac proteomic data*. J Physiol, 2005. 563(Pt 1): p. 73-81.
25. Thomas, R, *Boolean formalization of genetic control circuits*. J Theor Biol, 1973. 42(3): p. 563-85.

26. Li, S, Assmann, S, and Albert, R, *Predicting essential components of signal transduction networks: a dynamic model of guard cell abscisic acid signaling*. PLoS Biol, 2006. 4(10): p. e312.
27. Albert, R and Othmer, H, *The topology of the regulatory interactions predicts the expression pattern of the Drosophila segment polarity genes*. J. Theor. Biol., 2003. 223: p. 1-18.
28. Kauffman, S, Peterson, C, Samuelson, B, and Troein, C, *Random Boolean network models and the yeast transcription network*. Proc Natl Acad Sci USA, 2003. 100(25): p. 14796-14799.
29. Chaves, M, Albert, R, and Sontag, E D, *Robustness and fragility of Boolean models for genetic regulatory networks*. J Theor Biol, 2005. 235(3): p. 431-49.
30. Soni, A S, Jenkins, J W, and Sundaram, S S, *Determination of critical network interactions: an augmented Boolean pseudo-dynamics approach*. IET Syst Biol, 2008. 2(2): p. 55-63.
31. Glass, L, *Classification of biological networks by their qualitative dynamics*. J Theor Biol, 1975. 54(1): p. 85-107.
32. Glass, L and Kauffman, S A, *The logical analysis of continuous, non-linear biochemical control networks*. J Theor Biol, 1973. 39(1): p. 103-29.
33. Lambeth, M J and Kushmerick, M J, *A computational model for glycogenolysis in skeletal muscle*. Ann Biomed Eng, 2002. 30(6): p. 808-27.
34. Cortassa, S, Aon, M A, Marban, E, Winslow, R L, and O'Rourke, B, *An integrated model of cardiac mitochondrial energy metabolism and calcium dynamics*. Biophys J, 2003. 84(4): p. 2734-55.
35. Siegel, G J, Agranoff, B W, Albers, R W, Fisher, S K, and Uhler, M D, *Basic Neurochemistry*. 6th ed. 1999, Philadelphia, Pa.: Lippincott, Williams & Wilkins. 1200.
36. Ainscow, E K and Brand, M D, *Internal regulation of ATP turnover, glycolysis and oxidative phosphorylation in rat hepatocytes*. Eur J Biochem, 1999. 266(3): p. 737-49.
37. Hucka, M, Finney, A, Sauro, H M, Bolouri, H, Doyle, J C, et al., *The systems biology markup language (SBML): a medium for representation and exchange of biochemical network models*. Bioinformatics, 2003. 19(4): p. 524-31.
38. Zhou, L, Salem, J E, Saidel, G M, Stanley, W C, and Cabrera, M E, *Mechanistic model of cardiac energy metabolism predicts localization of glycolysis to cytosolic subdomain during ischemia*. Am J Physiol Heart Circ Physiol, 2005. 288(5): p. H2400-11.
39. Cakir, T, Alsan, S, Saybasili, H, Akin, A, and Ulgen, K O, *Reconstruction and flux analysis of coupling between metabolic pathways of astrocytes and neurons: application to cerebral hypoxia*. Theor Biol Med Model, 2007. 4: p. 48.
40. Bult, C J, White, O, Olsen, G J, Zhou, L, Fleischmann, R D, et al., *Complete Genome Sequence of the Methanogenic Archaeon, Methanococcus jannaschii*. Science, 1996. 273: p. 1058-73.
41. Riley, M, *Functions of gene products of Escherichia coli*. Microbiol. Rev., 1993. 57: p. 862-952.
42. Tomb, J-F, White, O, Kerlavage, A R, Clayton, R A, Sutton, G G, et al., *The complete genome sequence of the gastric pathogen Heliocobacter pylori*. Nature, 1997. 388(7): p. 539-547.
43. Bhalla, U S and Iyengar, R, *Emergent properties of networks of biological signaling pathways*. Science, 1999. 283(5400): p. 381-7.
44. Fink, C C, Slepchenko, B, and Loew, L M, *Determination of time-dependent inositol-1,4,5-trisphosphate concentrations during calcium release in a smooth muscle cell*. Biophys J, 1999. 77(1): p. 617-28.
45. Kauffman, S, *Gene regulation networks: a theory for their global structure and behaviors*. Curr Top Dev Biol, 1971. 6(6): p. 145-82.
46. Mehra, S, Hu, W, and Karypis, G, *A Boolean algorithm for reconstructing the structure of regulatory networks*. Metabolic Engineering, 2004. 6: p. 226-229.
47. Chaves, M, Albert, R, and Sontag, E D, *Methods of robustness analysis for Boolean models of gene control networks*. IEE Proceedings in Systems Biology, 2006. 153: p. 154-167.
48. Gupta, S, Bisht, S S, Kukreti, R, Jain, S, and Brahmachari, S K, *Boolean network analysis of a neurotransmitter signaling pathway*. J Theor Biol, 2007. 244(3): p. 463-9.
49. Chaves, M, Sontag, E D, and Albert, R, *Methods of robustness analysis for Boolean models of gene control networks*. Syst Biol (Stevenage), 2006. 153(4): p. 154-67.
50. Holleran, A L, Briscoe, D A, Fiskum, G, and Kelleher, J K, *Glutamine metabolism in AS-30D hepatoma cells. Evidence for its conversion into lipids via reductive carboxylation*. Molecular and Cellular Biochemistry, 1995. 152(2): p. 95-101.
51. Figenschou, A, Hu, G Y, and Storm, J F, *Cholinergic modulation of the action potential in rat hippocampal neurons*. European journal of neuroscience, 1996. 8(1): p. 211-9.
52. Klein, C, Sunahara, R K, Hudson, T Y, Heyduk, T, and Howlett, A C, *Zinc Inhibition of cAMP Signaling*. The Journal of Biological Chemistry, 2002. 227(14): p. 11859-11865
53. Ma, W, Pancrazio, J J, Coulombe, M, Dumm, J, Sathanoori, R S, Barker, J L, Kowtha, V C, Stenger, D A, and Hickman, J J, *Neuronal and glial epitopes and transmitter-synthesizing enzymes appear in parallel with membrane excitability during neuroblastoma×glioma hybrid differentiation*. Developmental Brain Research, 1998. 106 (1-2): p. 155-163.
54. Schaffner, A E, Barker, J L, Stenger, D A, and Hickman, J J, *Investigation of the factors necessary for growth of hippocampal neurons in a defined system*. J Neurosci Methods, 1995. 62(1-2): p. 111-9.
55. Mohan, D K, Molnar, P, and Hickman, J J, *Toxin detection based on action potential shape analysis using a realistic mathematical model of differentiated NG108-15 cells*. Biosensors & Bioelectronics, 2006. 21: p. 1804-1811.
56. Abbanat, D, Macielag, M, and Bush, K, *Novel antibacterial agents for the treatment of serious Gram-positive infections*. Expert Opinion of Investigational Drugs, 2003. 12: p. 379-399.
57. Haas, H L and Selbach, O, *Functions of neuronal adenosine receptors*. Naunyn Schmiedebergs Arch. Pharmacol., 2000. 362: p. 375-381.
58. Marhl M, Haberichter T, Brumen M, Heinrich R: *Complex calcium oscillations and the role of mitochondria and cytosolic proteins*. Biosystems 2000, 57:75-86.
59. Chen X F, Li C X, Wang P Y, Li M, Wang W C: *Dynamic simulation of the effect of calcium-release activated calcium channel on cytoplasmic Ca2+ oscillation*. Biophys Chem 2008, 136:87-95.
60. Akanda N, Molnar P, Stancescu M and Hickman J J: *Analysis of Toxin-Induced Changes in Action Potential Shape for Drug Development*. Journal of Biomolecular Screening, 14(10):1228-1235.

61. Schuster R, Holzhutter H G: *Use of mathematical models for predicting the metabolic effect of large-scale enzyme activity alterations. Application to enzyme deficiencies of red blood cells*. Eur J Biochem 1995, 229:403-418.
62. Siegel G J, Agranoff B W, Albers R W, Fisher S K, Uhler M D: *Basic Neurochemistry*. Philadelphia, Pa.: Lippincott, Williams & Wilkins; 1999.
63. Nazaret C, Heiske M, Thurley K, Mazat J P: Mitochondrial energetic metabolism: a simplified model of TCA cycle with ATP production. J Theor Biol 2009, 258:455-464.

That which is claimed is:

1. A method of identifying a point of action of a stimulus applied to an electrically active cell, the method comprising:
generating action potentials and associated cellular parameters using a model comprising a first submodel based on Hodgkin-Huxley calculations, a second submodel operably linked thereto and based on reaction kinetics of cell metabolism, and a third submodel operably linked to the first and second submodels and based on Boolean dynamics representing signaling and associated cellular processes;
storing a library of the generated action potentials and associated cellular parameters;
applying the stimulus to the electrically active cell in vitro so that the electrically active cell generates an action potential; and
comparing the cell-generated action potential with the generated action potentials stored in the library, wherein a match is predictive of the point of action of the stimulus according to cellular parameters stored in the library for the matching generated action potential, wherein the first, second, and third submodels are operably linked such that the model quantifies changes in intracellular processes based on physiological changes responsive to reaction kinetics of cell metabolism and signaling and associated cellular processes.

2. The method of claim 1, wherein the stimulus is selected from a compound, composition, electricity and electromagnetic radiation and combinations thereof.

3. The method of claim 1, wherein the stimulus comprises a toxin.

4. The method of claim 1, wherein the electrically active cell comprises a mammalian neuronal cell.

5. The method of claim 1, wherein the associated cellular parameters comprise a plurality of parameters selected from Boolean model data of simulated cell signaling cascades, scaling factors of cell metabolic processes, ion and adenosine triphosphate (ATP) concentrations, data for ion channels included in the Hodgkin-Huxley calculations, and combinations thereof.

6. The method of claim 1, wherein the second submodel comprises a plurality of modeled physiological compartments, each physiological compartment having an associated compartment volume.

7. The method of claim 6, wherein the modeled physiological compartments comprise whole cell volume, mitochondrial volume, endoplasmic reticulum volume, nuclear volume and extracellular volume.

8. The method of claim 7, wherein mitochondrial volume, endoplasmic reticulum volume, nuclear volume are nested in the whole cell volume.

9. The method of claim 1, wherein the third submodel further comprises network topology and dynamic state for each pathway node to thereby assign relative importance to a pathway node with respect to overall response of a biological network.

10. The method of claim 1, wherein the third submodel further comprises Glass dynamics providing a continuous time course simulation.

11. The method of claim 1, wherein the library is a structured query language database programmed in a computer.

12. The method of claim 1, further comprising maintaining the electrically active cell in an extracellular solution for a predetermined period of time before applying the stimulus.

13. The method of claim 12, wherein the extracellular solution comprises 2-desoxy-glucose (2DG).

14. The method of claim 12, further comprising calibrating the model based on reaction kinetics of cell metabolism.

15. The method of claim 14, wherein calibrating the model further comprises measuring at least one of glucose, 2-desoxy-glucose (2DG), lactate, or adenosine triphosphate (ATP) concentrations of a plurality of electrically active cells maintained in the extracellular solution.

16. The method of claim 1, wherein the second submodel comprises a plurality of modeled physiological compartments.

17. The method of claim 16, wherein the modeled physiological compartments represent at least one of a mitochondria, an endoplasmic reticulum, a nucleus, or an extracellular space.

* * * * *